United States Patent
Leadlay et al.

(10) Patent No.: US 7,807,418 B2
(45) Date of Patent: *Oct. 5, 2010

(54) METHOD FOR PRODUCING HYBRID POLYKETIDE SYNTHASES

(75) Inventors: Peter Francis Leadlay, Cambridge (GB); James Staunton, Cambridge (GB); Jesus Cortes, Cambridge (GB)

(73) Assignee: Biotica Technology Limited, Cambridge (GB)

( * ) Notice: Subject to any disclaimer, the term of this patent is extended or adjusted under 35 U.S.C. 154(b) by 888 days.

This patent is subject to a terminal disclaimer.

(21) Appl. No.: 10/889,519

(22) Filed: Jul. 12, 2004

(65) Prior Publication Data

US 2005/0089982 A1    Apr. 28, 2005

Related U.S. Application Data

(63) Continuation of application No. 09/214,453, filed as application No. PCT/GB97/01819 on Jul. 4, 1997, now Pat. No. 6,960,453.

(60) Provisional application No. 60/024,188, filed on Aug. 19, 1996.

(30) Foreign Application Priority Data

Jul. 5, 1996   (GB) .................................. 9614189.0
May 28, 1997   (GB) .................................. 9710962.3

(51) Int. Cl.
C12P 19/34    (2006.01)
C12P 21/04    (2006.01)
C12P 1/20     (2006.01)
C07H 21/02    (2006.01)

(52) U.S. Cl. .................. 435/91.1; 435/70.1; 435/252.1; 536/23.1

(58) Field of Classification Search ........................ None
See application file for complete search history.

(56) References Cited

U.S. PATENT DOCUMENTS

| | | |
|---|---|---|
| 5,141,926 A | 8/1992 | Weber et al. |
| 5,190,871 A | 3/1993 | Cox et al. |
| 5,672,491 A | 9/1997 | Khosla et al. |
| 5,712,146 A | 1/1998 | Khosla et al. |
| 5,824,513 A | 10/1998 | Katz et al. |
| 5,830,750 A | 11/1998 | Khosla et al. |
| 5,843,718 A | 12/1998 | Khosla et al. |
| 5,962,290 A | 10/1999 | Khosla et al. |
| 6,004,787 A | 12/1999 | Katz et al. |
| 6,022,731 A | 2/2000 | Khosla et al. |
| 6,060,234 A | 5/2000 | Katz et al. |
| 6,063,561 A | 5/2000 | Katz et al. |
| 6,066,721 A | 5/2000 | Khosla et al. |
| 6,271,255 B1 | 8/2001 | Leadlay et al. |
| 6,437,151 B2 | 8/2002 | Leadlay et al. |

FOREIGN PATENT DOCUMENTS

| | | |
|---|---|---|
| EP | 238892 | 3/1987 |
| WO | WO 93/13663 | 7/1993 |
| WO | WO 95/08548 | 3/1995 |
| WO | WO 96/40968 | 12/1996 |

OTHER PUBLICATIONS

Kao, et al., "Engineered biosynthesis of a complete macrolactone in a heterologous host," Science, 265:509-512, (1994).
Donadio, S., et al., "An erythromycin analog produced by reprogramming of polyketide synthesis," PNAS USA, 90:7119-7123, (1993).
Cortes, J., et al., "Repositioning of a domain in a modular polyketide synthase to promote specific chain cleavage," Science, 268:1487-1489, (1995).
Khosla, C., et al., "Genetic construction and functional analysis of hybrid polyketide synthases containing heterologous . . . ," Journal of Bacteriology, 175:2197-2204, (1993).
Fernandez-Moreno, M., et al., "Nucleotide sequence and deduced functions of a set of cotranscribed genes . . . ," Journal of Biological Chemistry, 267:19278-19290, (1992).
Kuhstoss, S., et al., "Production of a novel polyketide through the construction of a hybrid polyketide synthase," Gene, 183:231-236, (1996).
McDaniel, R., et al., "Construction of a . . . ," American Chemical Society, 205th ACS National Meeting, Denver, CO, Mar. 28-Apr. 2, 1993, Abstr. Pap. Am. Chem. Soc. 205 (1-2) (1993).
Pfeifer, et al., "Biosynthesis of complex polyketides in a metabolically engineered . . . ," Science, 291:1790-1792, (2001).
J.B. Brown et al., J. Chem. Soc., Chem. Commun., XP 002044729, 1517-1518 (1995).
G. Luo, et al Bioorg. Med. Chem. (1996), 4(7), 995-999.
R. Pieper, et al., Nature(London) (1995), 378(6554), 263-6.
R. Pieper, et al., J. Am. Chem. Soc. (1995), 117(45), 11373-4.
K. Wiesermann, et al., Chem. Biol. (1995), 2(9), 583-9.
C. Kao, et al., J. Am. Chem. Soc. (1994), 116(25), 11612-13.
R. Chen, et al., J. Liq. Chromatogr. (1988), 11(1), 191-201.
L. Katz and S. Donadio, Annu. Rev. Microbiol. (1993), 47 875-912.
S. Donadio and L. Katz, Gene (1992), 111(1), 51-60.
S. Donadio, et al., Gene (1992), 115(1-2), 97-103.
S. Donadio, et al., Science (1991), 252(5006), 675-9.
J. Tuan, et al., Gene (1990), 90(1), 21-9.
D. MacNeil, et al., Gene (1992), 115(1-2), 119-25.
D. MacNeil, et al., Ann. N. Y. Acad. Sci. (1994), 721(Recombinant DNA Technology II), 123-32.
D. MacNeil, et al., Gene (1992), 111(1), 61-8.
S. Haydock, et al., FEBS Lett. (1995), 374(2), 246-8.
S. Gaisser, et al., Mol. Gen. Genet. (1997), 256(3), 239-251.
K. Weissman, et al., Biochemistry (1997), 36(45), 13849-13855.

(Continued)

Primary Examiner—David J Steadman
Assistant Examiner—Alexander D Kim
(74) Attorney, Agent, or Firm—Dann, Dorfman, Herrell & Skillman; Robert C. Netter

(57) ABSTRACT

A hybrid type I polyketide synthase gene typically containing a starter module and a plurality of heterologous extender modules is used to synthesise novel polyketides. It is preferably under the control of type II polypolyketide synthase promoter e.g. act I or S. coelicolor.

17 Claims, 47 Drawing Sheets

OTHER PUBLICATIONS

T. Schwecke, et al., Proc. Natl. Acad. Sci. U.S.A. (1995), 92(17), 7839-43.
P. Leadlay, et al., Curr. Opin. Chem. Biol. (1997), 1(2), 162-168.
A. Konig, et al., Eur. J. Biochem. (1997), 247(2), 526-534.
S. Less, Tetrahedron Lett. (1996), 37(20), 3519-3520.
S. Less, Tetrahedron Lett. (1996), 37(20), 3511-3514.
J. Aparicio, et al., Gene (1996), 169(1), 9-16.
I. Molnar, et al., Gene (1996), 169(1), 1-7.
J. Staunton, et al., Nat. Struct. Biol. (1996), 3(2), 188-92.
J. Aparicio, et al., J. Biol. Chem. (1994), 269(11), 8524-8.
P. Leadlay, et al., Biochem. Soc. Trans. (1993), 21(1), 218-22.
J. McAlpine, et al., J. Antibiot. (1987), 40(8), 1115-22.
P.A.S. Lowden, et al., Angewandte Chemie Intl. Edn. (1996), (Engl.), 35, 2249-2251.
I.S. Galloway, et al., Faseb Journal, (1997), 11, 1680.
P.F. Leadlay, Faseb Journal (1997), 11, 2548.
H.D. Lewis, et al., Faseb Journal (1997), 11, 1022.
M. Oliynyk, et al., Faseb Journal (1997), 11, 2644.
J. Staunton, et al., (1997) Developments in Industrial Microbiology—GMBIM, edited by Baltz, R.H., Hegeman, G.D., and Skatrud, P.L., American Society for Microbiology, Washin.
I. Kibwage, et al., J. Antibiotics (1987), 15(1), 1-6.
Witkowski, et al., "Conversion of b-ketoacyl synthase to a malonyl decarboxylase . . . ," Biochemistry, 38:11643-11650, (1999).

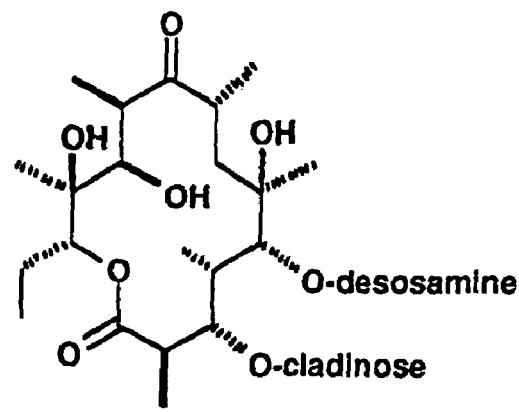
Erythromycin A
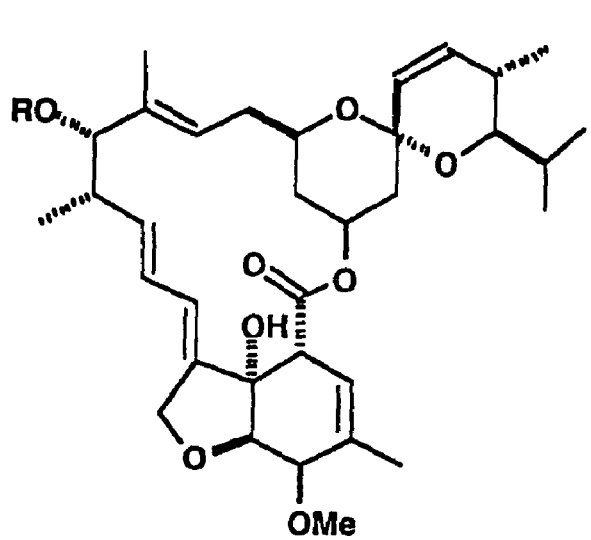
Avermectin A1b
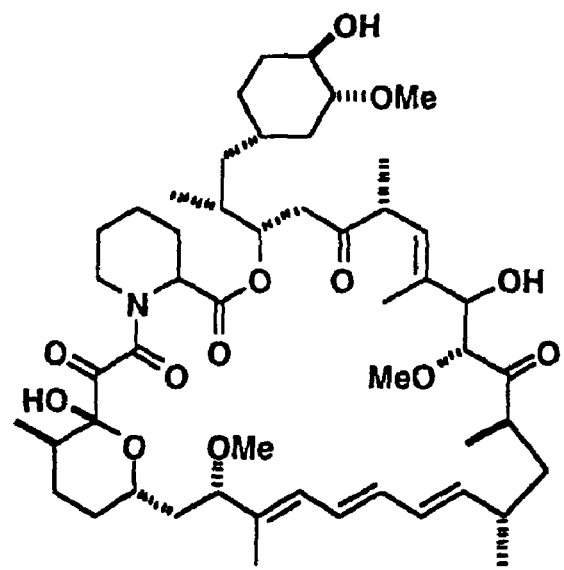
Rapamycin
Figure 1

Figure 5. Construction of pJC3

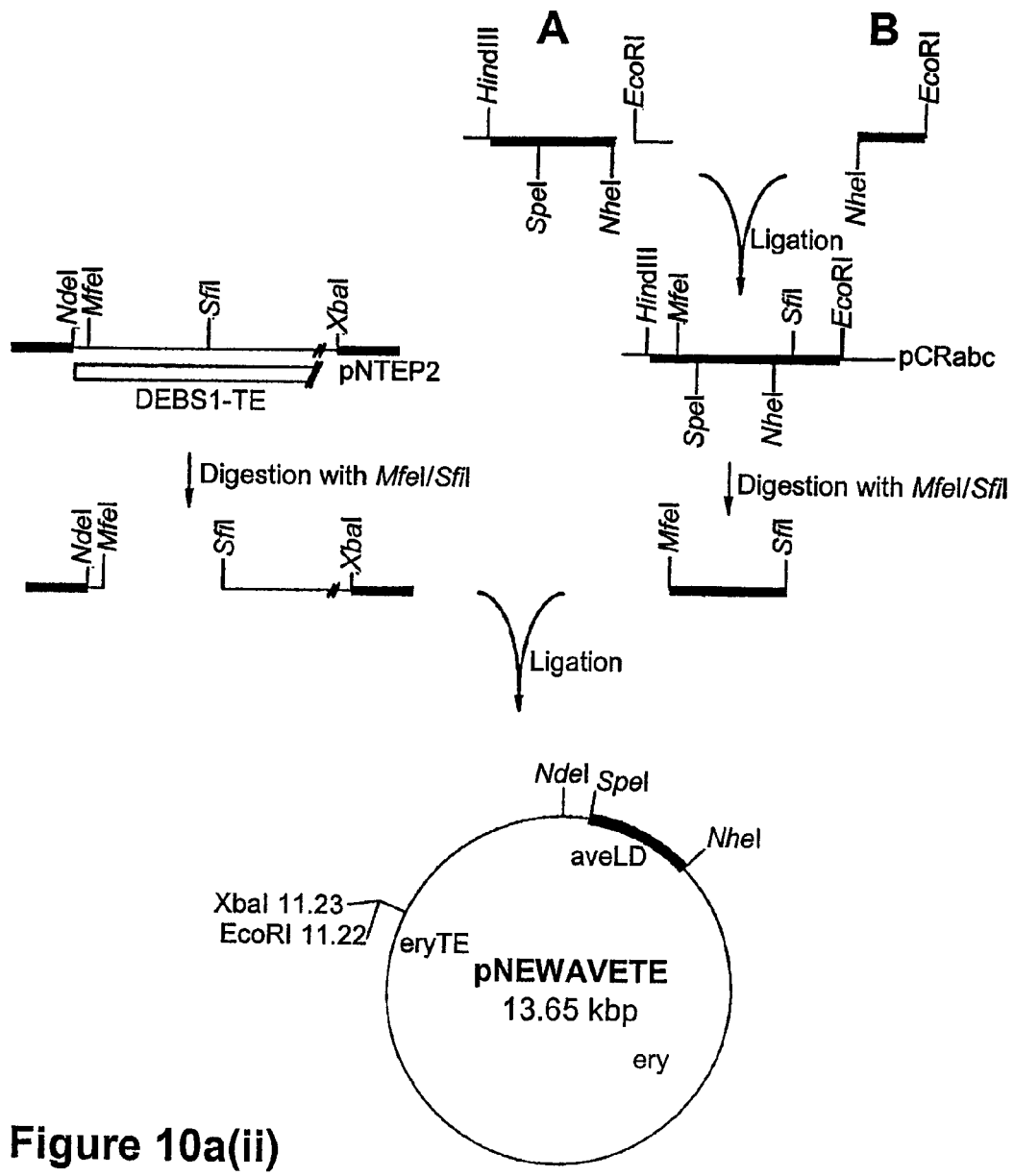
Figure 10a(ii)

Construction of DKS

Construction of a Diketide Synthase With Different Reductive Loops

Fig 23. Construction of plasmid pKETO

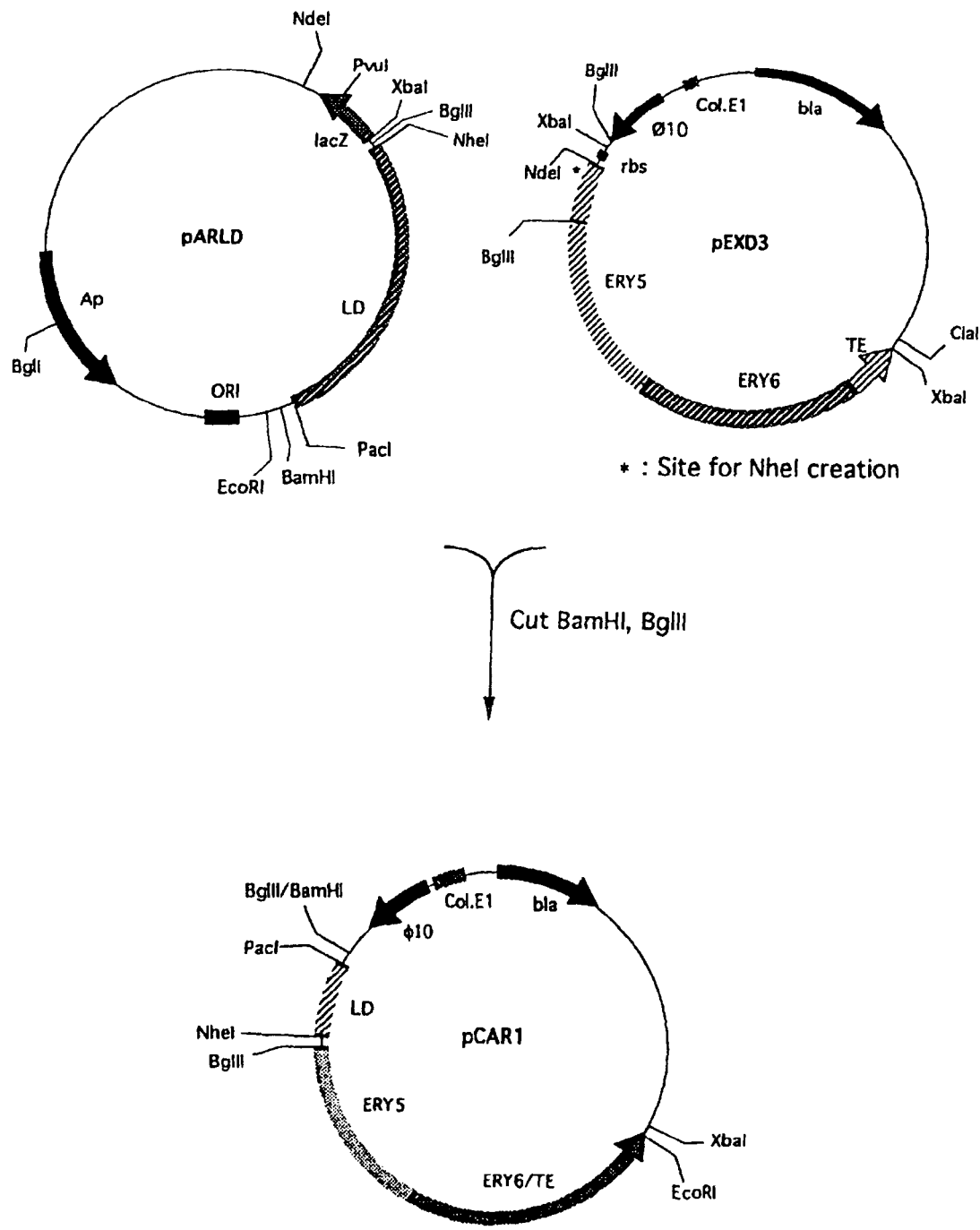
Figure 29a: Construction of pCART11

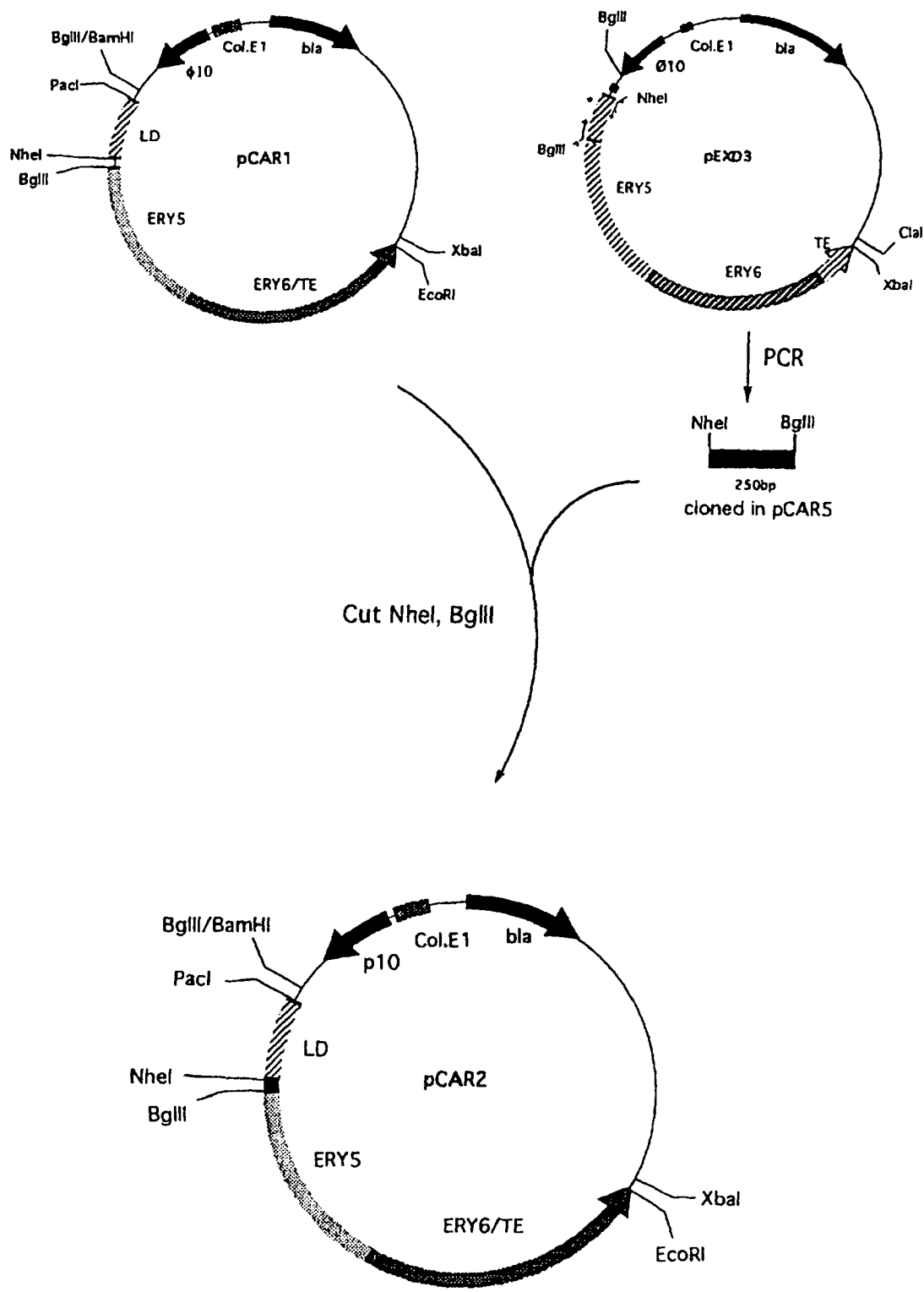
Figure 29b: Construction of pCART11

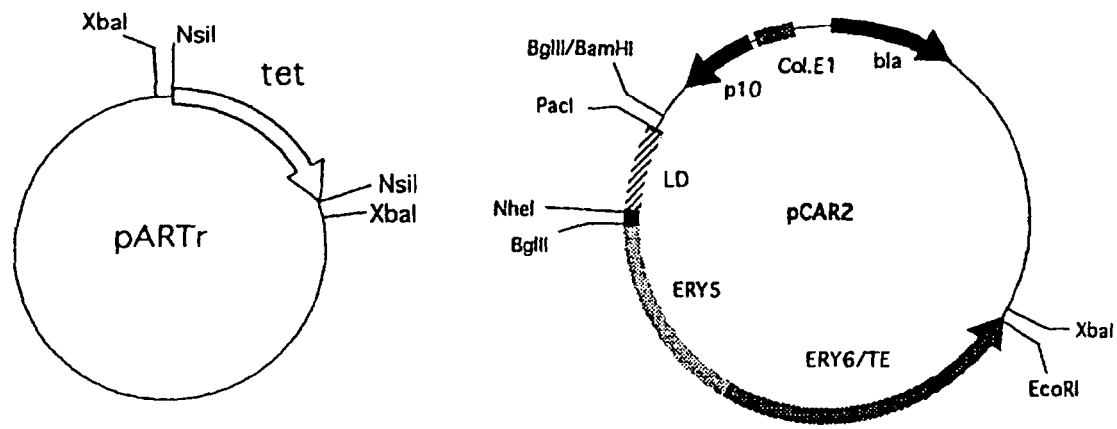
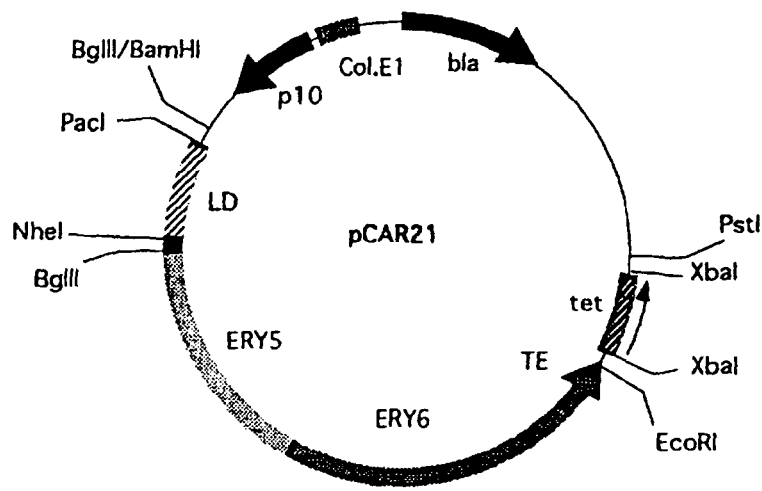
Figure 29c: Construction of pCART11

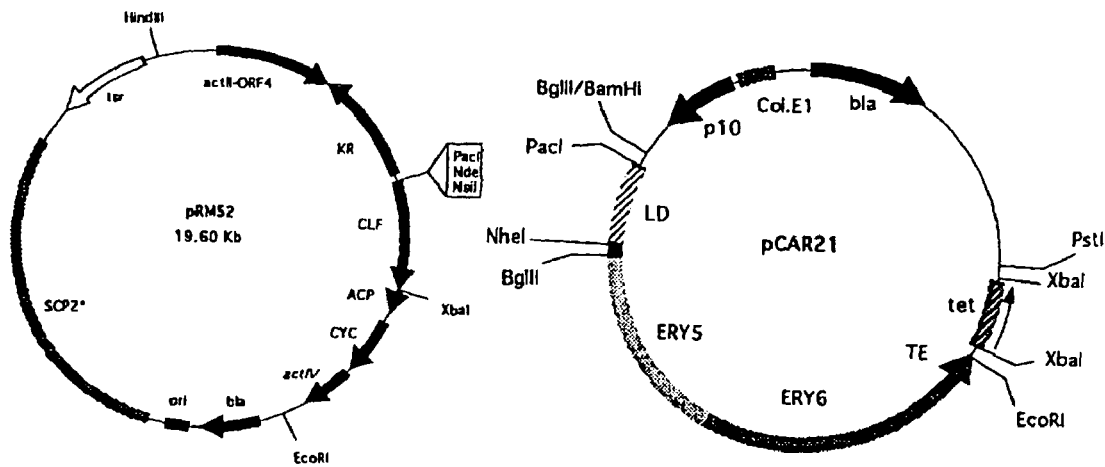
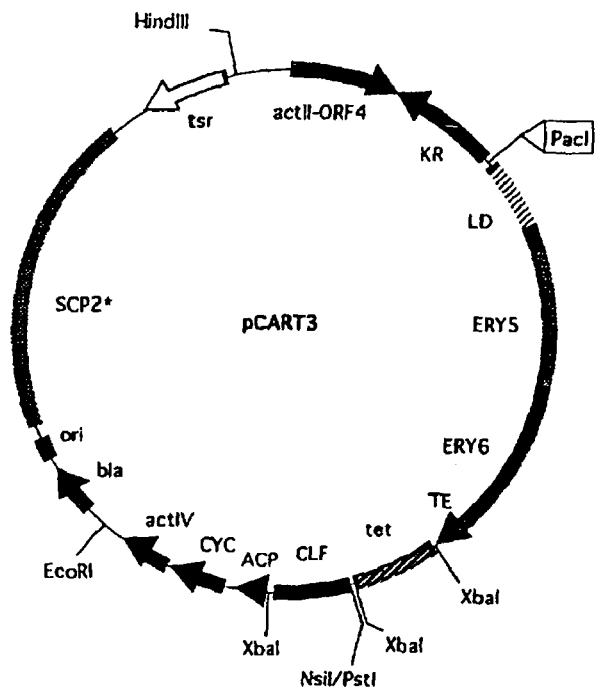
Figure 29d: Construction of pCART11

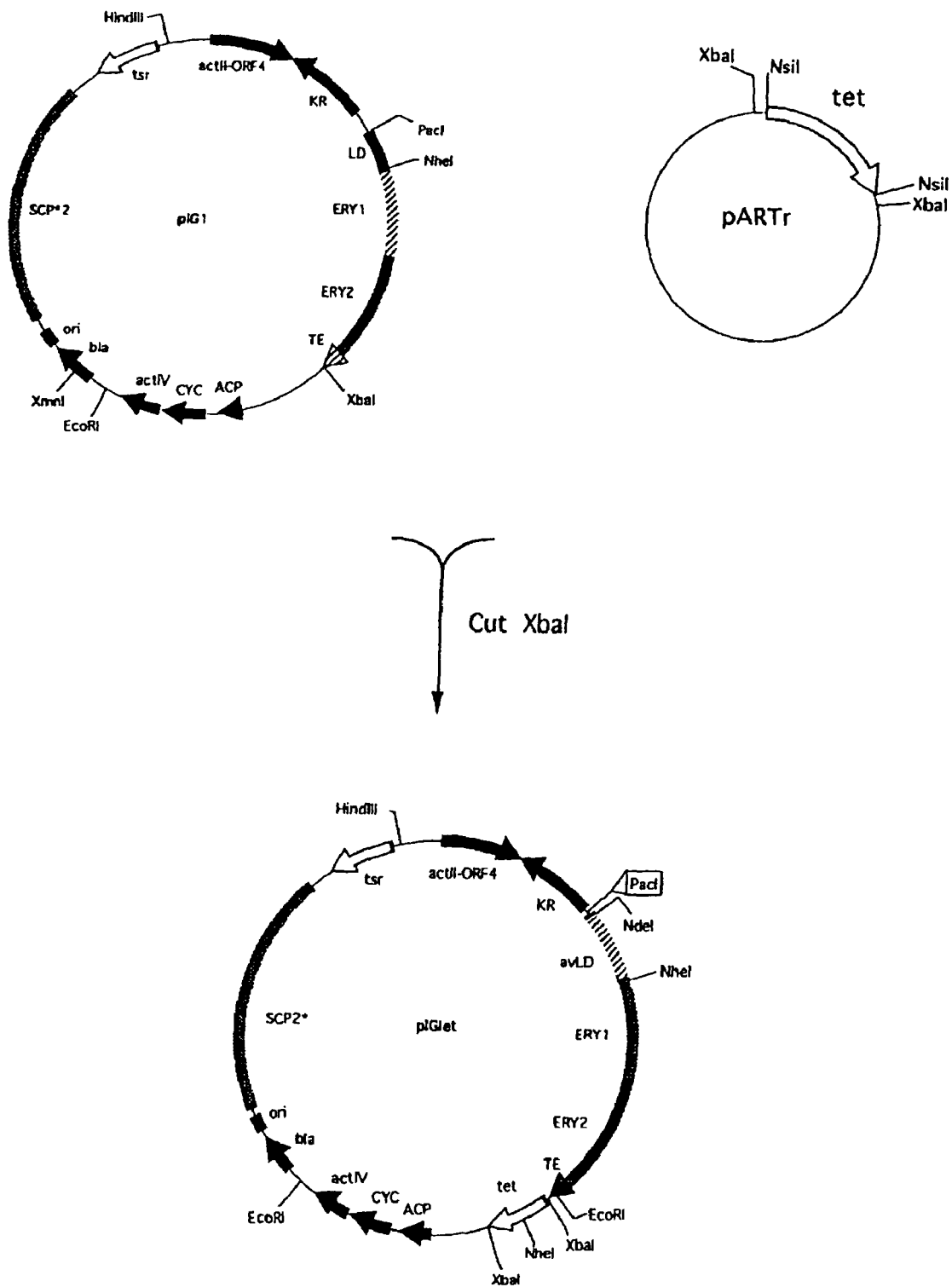
Figure 29e: Construction of pCART11

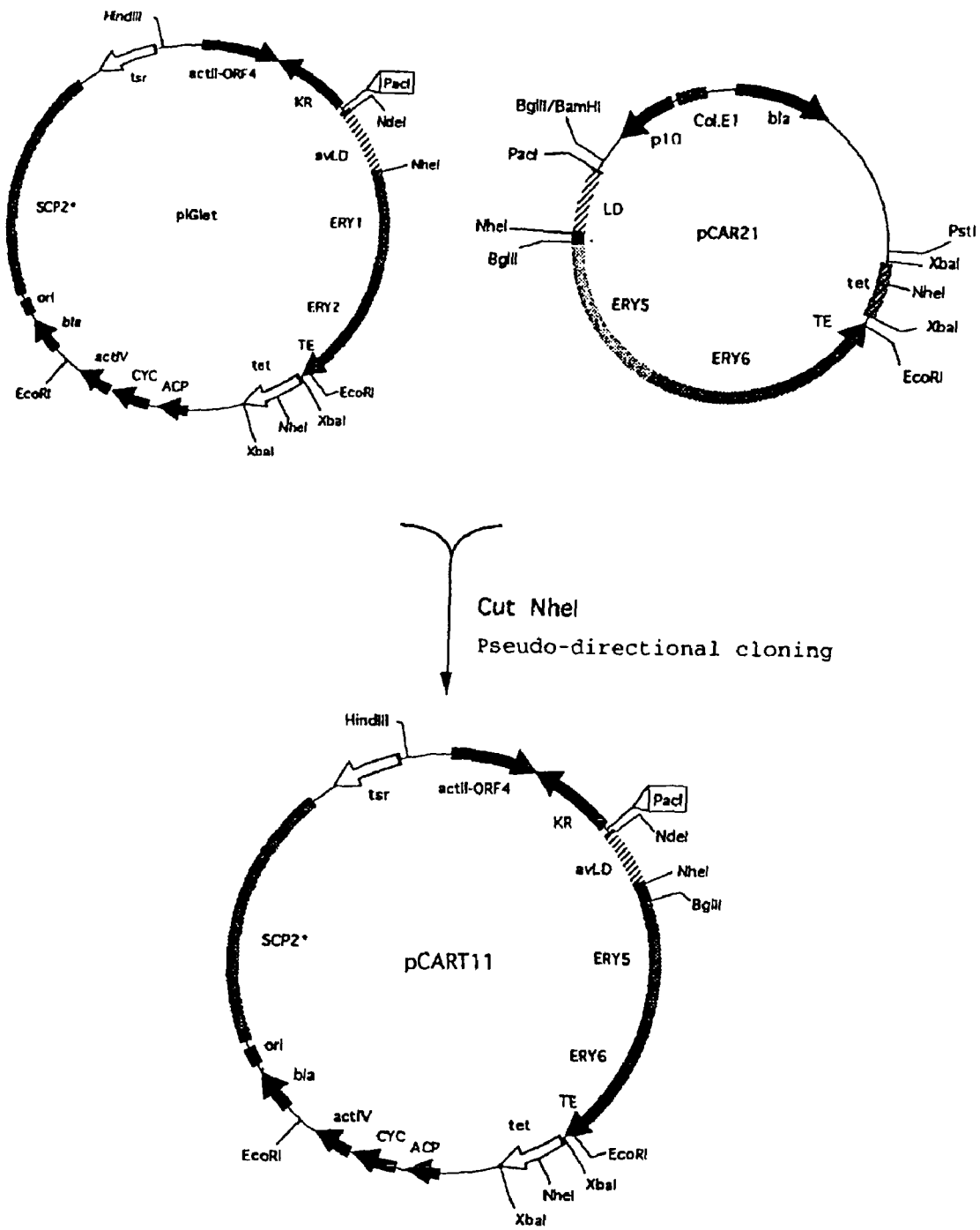
Figure 29f: Construction of pCART11

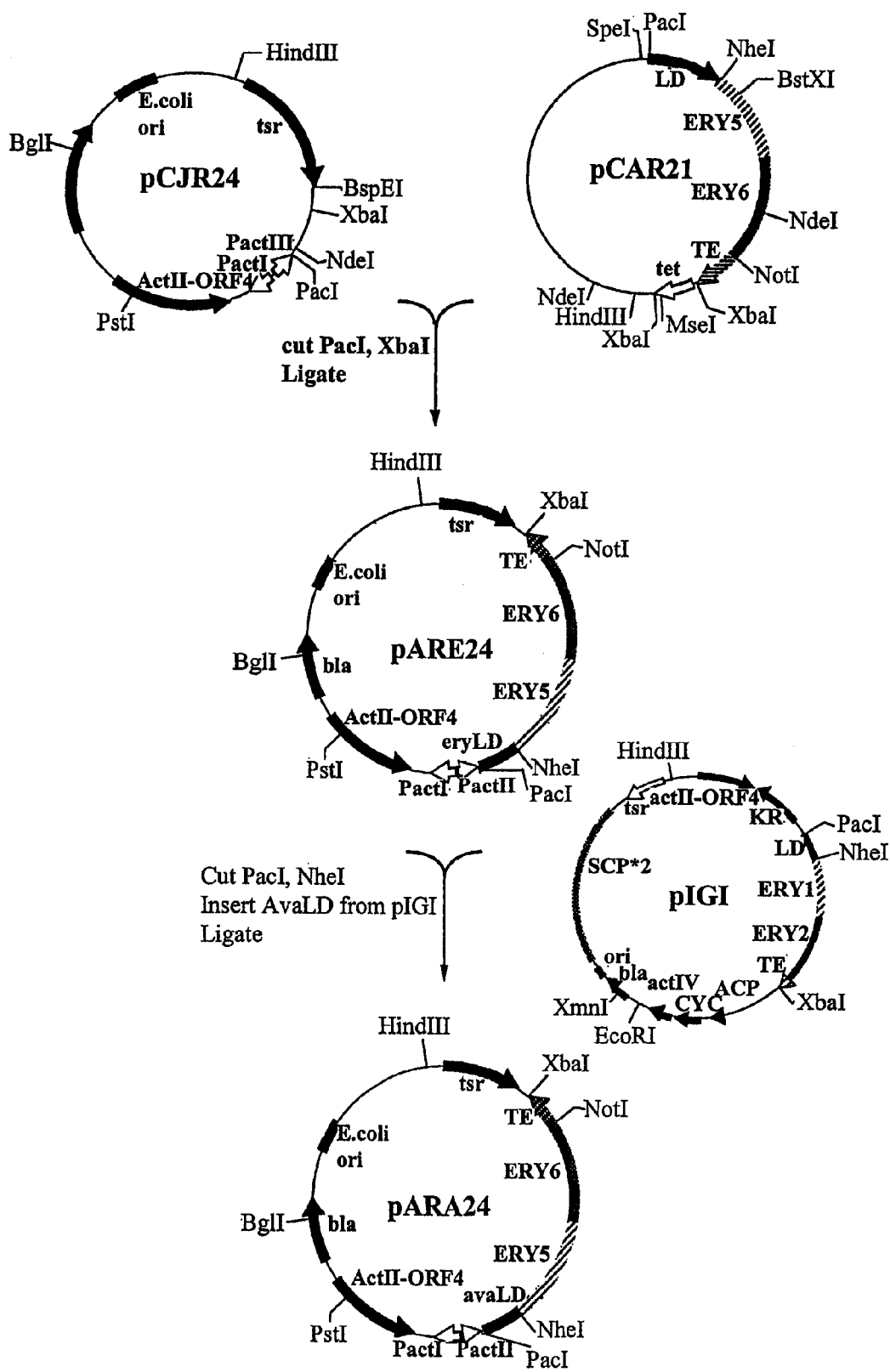
Figure 30: Construction of plasmids pARE24 and pARA24

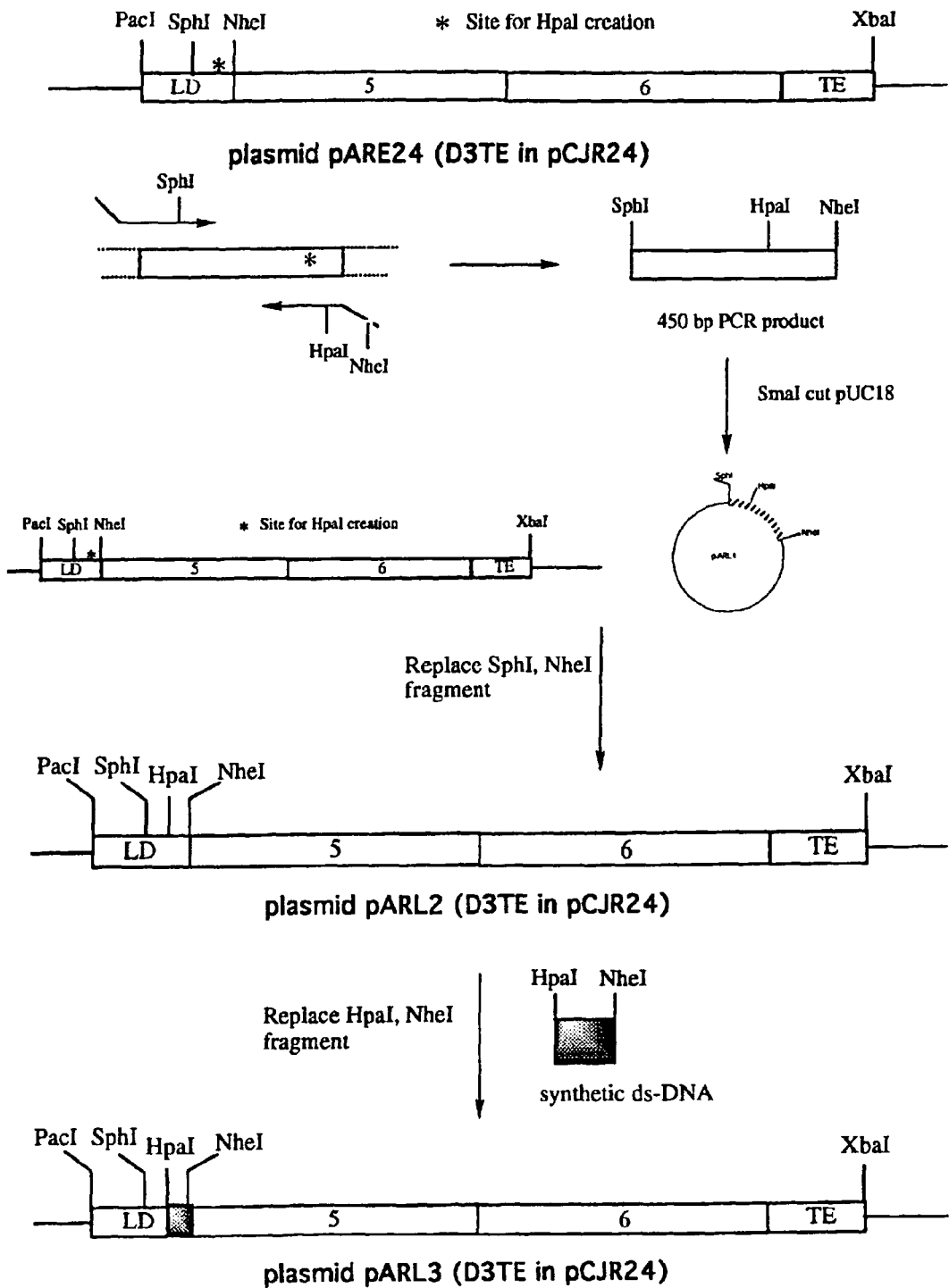
Figure 31 : Construction of plasmid pARL3

Synthesis of Ketolides by ΔKR6

ESMS : MH⁺ = 558.4

C₂₉H₅₂O₉N requires 558.36418; found 558.36427

METHOD FOR PRODUCING HYBRID POLYKETIDE SYNTHASES

This application is a continuation application of U.S. patent application Ser. No. 09/214,453 filed Oct. 25, 1999, now U.S. Pat. No. 6,960,453, which is the U.S. National Stage of PCT/GB97/01819, filed Jul. 4, 1997, and which claims the benefit of U.S. Provisional No. 60/024,188, filed Aug. 19, 1996, as well as the following Applications: Great Britain No. GB9614189.0, filed Jul. 5, 1996 and Great Britain No. 9710962.3, filed May 28, 1997. The entire disclosure of each of the foregoing applications is incorporated by reference herein.

The present invention relates to novel polyketides and methods and means for preparing them by recombinant synthesis. Polyketide biosynthetic genes or portions of them, which may be derived from different polyketide biosynthetic gene clusters are manipulated to allow the production of specific novel hybrid polyketides of predicted structure. The invention also relates to novel host-vector systems allowing increased levels of production of both natural and non-natural polyketides, both in vivo and in vitro.

Polyketides are a large and structurally diverse class of natural products that includes many compounds possessing antibiotic or other pharmacological properties, such as erythromycin, tetracyclines, rapamycin, avermectin and FK506. In particular, polyketides are abundantly produced by *Streptomyces* and related actinomycete bacteria. They are synthesised by the repeated stepwise condensation of acylthioesters in a manner analogous to that of fatty acid biosynthesis. The greater structural diversity found among natural polyketides arises from the selection of (usually) acetate or propionate as "starter" or "extender" units; and from the differing degree of processing of the □β-keto group observed after each condensation. Examples of processing steps include reduction to □β-hydroxyacyl-, reduction followed by dehydration to 2-enoyl-, and complete reduction to the saturated acylthioester. The stereochemical outcome of these processing steps is also specified for each cycle of chain extension.

The biosynthesis of polyketides is initiated by a group of chain-forming enzymes known as polyketide synthases. Two classes of polyketide synthase (PKS) have been described in actinomycetes. One class, named Type I PKSs, represented by the PKSs for the macrolides erythromycin, avermectin and rapamycin (FIG. 1), consists of a different set or "module" of enzymes for each cycle of polyketide chain extension (FIG. 2)(Cortes, J. et al. Nature (1990) 348:176-178; Donadio, S. et al. Science (1991) 252:675-679; MacNeil, D. J. et al. Gene (1992), 115:119-125; Schwecke, T. et al. Proc. Natl. Acad. Sci. USA (1995) 92:7839-7843). Note: the term "natural module" as used herein refers to the set of contiguous domains, from a β-ketoacyl-ACP synthase ("KS") gene to the next acyl carrier protein ("ACP") gene, which accomplishes one cycle of polyketide chain extension. The term "combinatorial module" is used to refer to any group of contiguous domains (and domain parts), extending from a first point in a first natural module, to a second equivalent point in a second natural module. The first and second points will generally be in core domains which are present in all modules, ie both at equivalent points of respective KS, AT (acyl transferase) or ACP domains. The length of polyketide formed has been altered, in the case of erythromycin biosynthesis, by specific relocation using genetic engineering of the enzymatic domain of the erythromycin-producing PKS that contains the chain-releasing thioesterase/cyclase activity (Cortes, J. et al. Science (1995) 268:1487-1489; Kao, C. M. et al. J. Am. Chem. Soc. (1995) 117:9105-9106)

In-frame deletion of the DNA encoding part of the ketoreductase domain in module 5 of the erythromycin-producing PKS, (also known as 6-deoxyerythronolide B synthase, DEBS) has been shown to lead to the formation of erythromycin analogues 5,6-dideoxy-3-α-mycarosyl-5-oxoerythronolide B, 5,6-dideoxy-5-oxoerythronolide B and 5,6-dideoxy-6,6□-epoxy-5-oxoerythronolide B (Donadio, S. et al. Science, (1991) 252:675-679). Likewise, alteration of active site residues in the enoylreductase domain of module 4 in DEBS, by genetic engineering of the corresponding PKS-encoding DNA and its introduction into *Saccharopolyspora erythraea*, led to the production of 6,7-anhydroerythromycin C (Donadio S. et al. Proc. Natl. Acad. Sci. USA (1993) 90:7119-7123).

International Patent Application number WO 93/13663 describes additional types of genetic manipulation of the DEBS genes that are capable of producing altered polyketides. However, many such attempts are reported to have been unproductive (Hutchinson C. R. and Fujii, I. Annu. Rev. Microbiol. (1995) 49:201-238, at p.231), and no further examples of altered polyketides have been reported. The complete DNA sequence of the genes from *Streptomyces hygroscopicus* that encode the modular Type 1 PKS governing the biosynthesis of the macrocyclic immunosuppressant polyketide rapamycin has been disclosed (Schwecke, T. et al. (1995) Proc. Natl. Acad. Sci. USA 92:7839-7843)(FIG. 3). The DNA sequence is deposited in the EMBL/Genbank Database under the accession number X86780.

The second class of PKS, named Type II PKSs, is represented by the synthases for aromatic compounds. Type II PKSs contain only a single set of enzymatic activities for chain extension and these are re-used as appropriate in successive cycles (Bibb, M. J. et al. EMBO J. (1989) 8:2727-2736; Sherman, D. H. et al. EMBO J. (1989) 8:2717-2725; Fernandez-Moreno, M. A. et al. J. Biol. Chem. (1992) 267: 19278-19290). The "extender" units for the Type II PKSs are usually acetate units, and the presence of specific cyclases dictates the preferred pathway for cyclisation of the completed chain into an aromatic product (Hutchinson, C. R. and Fujii, I. Annu. Rev. Microbiol. (1995) 49:201-238). Hybrid polyketides have been obtained by the introduction of cloned Type II PKS gene-containing DNA into another strain containing a different Type II PKS gene cluster, for example by introduction of DNA derived from the gene cluster for actinorhodin, a blue-pigmented polyketide from *Streptomyces coelicolor*, into an anthraquinone polyketide-producing strain of *Streptomyces galileus* (Bartel, P. L. et al. J. Bacteriol. (1990) 172:4816-4826).

International Patent Application Number WO 95/08548 describes the replacement of actinorhodin PKS genes by heterologous DNA from other Type II PKS clusters, to obtain hybrid polyketides. The same International Patent Application WO 95/08548 describes the construction of a strain of *Streptomyces coelicolor* which substantially lacks the native gene cluster for actinorhodin, and the use in that strain of a plasmid vector pRM5 derived from the low-copy number plasmid vector SCP2* isolated from *Streptomyces coelicolor* (Bibb, M. J. and Hopwood, D. A. J. Gen. Microbiol. (1981) 126:427) and in which heterologous PKS-containing DNA may be expressed under the control of the divergent act I/act III promoter region of the actinorhodin gene cluster (Fernandez-Moreno, M. A. et al. J. Biol. Chem. (1992) 267:19278-19290) The plasmid pRM5 also contains DNA from the actinorhodin biosynthetic gene cluster encoding the gene for a specific activator protein, Act II-orf4. The Act II-orf4 protein is required for transcription of the genes placed under the control of the act I/act III bidirectional promoter and activates expression during the transition from growth to stationary phase in the vegetative mycelium (Hallam, S. E. et. al. Gene (1988) 74:305-320).

Type II PKS clusters in *Streptomyces* are known to be activated by pathway-specific activator genes (Narva, K. E. and Feitelson, J. S. J. Bacteriol. (1990) 172:326-333; Stutzman-Engwall, K. J. et al. J. Bacteriol (1992) 174:144-154; Fernandez-Moreno, M. et al. Cell (1991) 66:769-780; Takano, E. et al. Mol. Microbiol. (1992) 7:837-845; Takano, E. et al. Mol. Microbiol. (1992) 6:2797-2804) whose gene product is required for transcription from specific promoters. The gene product of the activator genes is speculated to act by binding to specific DNA sequences in promoters of the PKS gene cluster in which the activator gene is located (Stutzman-Engwall, K. J. et al. J. Bacteriol (1992) 174:144-154; Takano, E. et al. Mol. Microbiol. (1992) 7:837-845). The DnrI gene product complements a mutation in the actII-orf4 gene of *S. coelicolor*, implying that DnrI and ActII-orf4 proteins act on similar targets. A gene (srmR) has been described (EP 0 524 832 A2) that is located near the Type I PKS gene cluster for the macrolide polyketide spiramycin, this gene specifically activates the production of the macrolide polyketide spiramycin, but no other examples have been found of such a gene. Also, no homologues of the ActII-orf4/DnrI/RedD family of activators have been described that act on Type I PKS genes.

Although large numbers of therapeutically important polyketides have been identified, there remains a need to obtain novel polyketides that have enhanced properties or possess completely novel bioactivity. The complex polyketides produced by modular Type I PKSs are particularly valuable, in that they include compounds with known utility as antihelminthics, insecticides, immunosuppressants, antifungal or antibacterial agents. Because of their structural complexity, such novel polyketides are not readily obtainable by total chemical synthesis, or by chemical modifications of known polyketides.

There is a need to develop reliable and specific ways of deploying individual modules in practice so that all, or a large fraction, of hybrid PKS genes that are constructed, are viable and produce the desired polyketide product. This is particularly true if it is desired to create large numbers of individual PKS gene sets using Type I modular PKS genes in a combinatorial fashion, where it will not be feasible to analyse all members of the set. Such libraries of polyketides offer a highly attractive alternative to the random screening of soil samples for the discovery of novel polyketides with valuable bioactive properties.

Similarly, although specific host-vector combinations have been reported that allow the controlled expression of heterologous genes in certain *Streptomyces* as for example using induction by added thiostrepton as described for *Streptomyces lividans* 66 and *Streptomyces coelicolor* (Takano, E. et al. Gene (1995) 166:133-137) and by utilising nutritional signals at the onset of differentiation, as for *Streptomyces coelicolor* in International Patent Application number WO 95/08548, there remains an important need for the development of general methods of controlling and even enhancing the expression of a structural gene, or of a set of structural genes, that governs the biosynthesis of a potentially valuable secondary metabolite such as one of the complex polyketides, in an engineered strain of *Streptomyces or* of a related filamentous bacterium.

One aspect of the invention arises from our appreciation that a PKS gene assembly (particularly of type I) encodes a loading module which is followed by extension modules. Thus FIG. 2 shows the organisation of the DEBS genes. The first open reading frame encodes the first multi-enzyme or cassette (DEBS1) which consists of three modules: the loading module (ery-load) and two extension modules (modules 1 and 2). The loading module comprises an acyl transferase and an acyl carrier protein. This may be contrasted with FIG. 1 of WO93/13663 (referred to above). This shows ORF1 to consist of only two modules, the first of which is in fact both the loading module and the first extension module.

In one aspect the invention concerns the production of a hybrid PKS gene assembly comprising a loading module and at least one, and preferably a plurality, of extension modules by assembling together a first nucleic acid portion or portions encoding at least one domain of a first type I PKS with a second nucleic acid portion or portions encoding at least one type I PKS domain which is heterologous to said first PKS. Generally the nucleic acids are DNA. The first and second portions may each encode domain(s) of respective different PKS's.

Preferably the hybrid PKS encodes a loading module and from 1 to 6 extension modules within any give cassette. More preferably there are at least 2 extension modules. NB: products resulting from many more than 6 modules can result from assemblies of synthases (c.f. rapamycin). The first portion may encode a loading module, while the second portion encodes one or more extension modules. Alternatively the first portion(s) may encode all or part of a loading module, the first two extension modules, and a chain terminating enzyme (generally a thioesterase), e.g. of erythromycin PKS, and the second portion(s) correspond to one or more domains and/or modules of a different PKS.

It is particularly useful to provide a hybrid PKS gene assembly in which the loading module is heterologous to the extension modules and is such as to lead to a polyketide having an altered starter unit. NB: This is a concept quite unknown to the prior art since this does not recognise the existence of loading modules. WO93/13663 refers to altering PKS genes by inactivating a single function (i.e. a single enzyme) or affecting "an entire module" by deletion, insertion or replacement thereof. But in their terms the loading assembly is not a module. If the loading module is one which accepts many different carboxylic acid units then the hybrid gene assembly can be used to produce many different polyketides. For example a hybrid gene assembly may employ nucleic acid encoding an avr loading module with erv extender modules. A loading module may accept unnatural acid units. Alternatively or additionally we may alter the end of a gene assembly. Thus the normal chain terminating enzyme of a PKS (usually thioesterase) may be replaced by an enzyme leading to a different type of product. Thus use may be made of the enzyme from the rapamycin system that connects the polyketide chain to an aminoacid chain. This can be used to synthesise polypeptide/polyketide combinations, e.g. for producing □β-lactam derivatives.

Of course one may make alterations within a product polyketide, particularly by replacing an extension module by one that gives a ketide unit at a different oxidation state and/or with a different stereochemistry. NB: It has generally been assumed that the stereochemistry of the methyl groups in the polyketide chain is determined by the acyltransferase. But it is in fact a feature of other domains of the PKS, and thus open to variation only by replacement of those domains, individually or by module replacement. Methyl and other substituents can be added or removed by acyltransferase domain replacement or total module replacement.

This aspect of the invention is largely concerned with treating PKS gene modules as building blocks that can be used to construct enzyme systems, and thus polyketide products, of desired types. This generally involves the cutting out and the assembly of modules and multi-module groupings. It might be assumed that the correct places for making and breaking intermodular connections would be in the linking regions between modules, where our previously-reported experiments using limited proteolysis have shown those linkers to be on the surface of the protein (Aparicio, J. F. et al. (1994) J. Biol. Chem. 269:8524-8528; Staunton, J. et al. (1996) Nature Structural Biol. 3:188-192). However we have found that it may be preferable to make cuts and joins actually within domains (i.e. the enzyme-coding portions), close to the edges thereof. The DNA is highly conserved here between all modular PKS's, and this may aid in the construction of hybrids that can be transcribed. It also assists in maintaining the spacing of the active sites of the encoded enzymes, which may be important. For example in producing a hybrid gene by replacing the ery loading module by an avr loading module, we removed the ery module together with a small amount of the following ketosynthase (KS) domain. The start of the KS domain (well spaced from the active site) is highly conserved and therefore provides an alternative splicing site to the obvious site in the linker region between loading module and KS domain. The excised ery module was then replaced by an avr loading module.

In fact when substituting a loading module, it may be desirable to replace not just the loading module domains (generally acyl transferase (AT) and acyl carrier protein (ACP)) but also the KS at the start of the following extension module. Typically the excised loading module would have provided a propionate starter, and the replacement is intended to provide one or more different starters. But propionate may feed in to the KS of the extension module from a propionate pool in the host cell, leading to dilution of the desired products. This can be largely prevented by substituting an extended loading module including all or most of the KS domain. (The splice site may be in the end region of the KS gene, or early in the following AT gene, or in the linker region between the KS and AT domains.)

When replacing "modules", we are not restricted to "natural" modules. For example a "combinatorial module" to be excised and/or replaced and/or inserted may extend from the corresponding domain of two natural-type modules, e.g. from the AT of one module to the AT of the next, or from KS to KS. The splice sites will be in corresponding conserved marginal regions, or in linker regions between domains near known sites for limited proteolysis. A combinatorial module can also be a 'double' or larger multiple, for adding 2 or more modules at a time. The invention further provides such gene assemblies, vectors containing such gene assemblies, and transformant organisms that can express them. Transformant organisms may harbour recombinant plasmids, or the plasmids may integrate. A plasmid with an int sequence will integrate into a specific attachment site (att) of a host's chromosome. Transformant organisms may be capable of modifying the initial products, e.g. by carrying out all or some of the biosynthetic modifications normal in the production of erythromycins (as shown in FIG. 2B) and/or other polyketides. Use may be made of mutant organisms such that some of the normal pathways are blocked, e.g. to produce products without one or more "natural" hydroxy-groups or sugar groups. The invention further provides novel polyketides as producible, directly or indirectly, by transformant organisms. (This includes polyketides which have undergone enzymic modification in the organisms and/or have been isolated and subjected to chemical modification.)

In a second aspect the invention provides a hybrid gene assembly comprising structural gene components operably linked to a promoter which is not naturally linked thereto and is of a type II PKS, preferably linked to its specific cognate activator gene. Particularly preferred is the use of the act I promoter and the Act II-orf4 activator gene from S.coelicolor, for expression in hosts other than S.coelicolor (usually other actinomycetes, particularly other streptomycetes). The structural gene components may be of a type I PKS gene system.

The invention in its second aspect further provides vectors containing such gene assemblies, and transformant organisms that can express them. It is possible to combine the two aspects of the invention, so that a hybrid type I gene is expressed under the control of a type II promoter.

In a further aspect the invention provides novel polyketides obtainable by means of the previous aspects. These include the following.

(i) An erythromycin analogue (being a macrolide compound with a 14-membered ring) in which C-13 bears a side-chain other than ethyl, generally an □-branched $C_2$-$C_5$ alkyl group, a $C_3$-$C_8$ cycloalkyl or cycloalkenyl group (optionally substituted e.g. with one or more hydroxy, $C_{1-4}$ alkyl or alkoxy groups or halogen atoms), or a 3-6 membered heterocycle containing O or S, saturated or fully or partially unsaturated, optionally substituted (as for cycloalkyl). Preferred candidates for the C-13 substituent R are the groups of carboxylate units R. C0.0-usable as substrates by an avr starter module, or rapamycin starter variants. Preferred substrates include isobutyrate (R=i-Pr) and 2-methylbutyrate (R=1-methylpropyl). Other possibilities include n-butyrate, cyclohexyl carboxylate, cycloheptanyl carboxylate, cyclohexenyl carboxylates, cycloheptenyl carboxylates, and ring-methylated variants of the cyclic carboxylates.

The erythromycin analogue may correspond to the initial product of a PKS (6-deoxyerythronolide) or the product after one or more of the normal biosynthetic steps. As shown in FIG. 2B these comprise: 6-hydroxylation; 3-0-glycosylation; 5-0-glycosylation; 12-hydroxylation; and specific sugar methylation.

Thus the analogues include ones corresponding to 6-deoxyerythronolide B, erythromycin A, and the various intermediates and alternatives shown in FIG. 2B.

Additionally or alternatively, there may be chemical modification. For example one or more hydroxy groups may be oxidised (e.g. to produce 3-keto derivatives) or eliminated (e.g. to produce 10-ene derivatives). Some examples of chemical modifications applicable to the present inventions are those that give rise to azithromycin, roxithromycin, clarithromycin and those disclosed in some French patents of Roussel Uclaf:2697523, 2697524 and 2702480.

(ii) erythromycin analogues differing from the corresponding 'natural' compound (FIG. 2a) in the oxidation state of one or more of the ketide units (i.e. selection of alternatives from the group: —CO—, —CH(OH)—, =CH—, and —CH$_2$—).

The stereochemistry of any —CH(OH)— is also independently selectable.

(iii) erythromycin analogues differing from the corresponding 'natural' compound in the absence of a 'natural' methyl side-chain. (This is achievable by use of a variant AT). Normal extension modules use either $C_2$ or $C_3$ units to provide unmethylated and methylated ketide units. We may provide unmethylated units where methylated units are natural (and vice versa, in systems where there are naturally unmethylated units) and also provide larger units, e.g. $C_4$ to provide ethyl substituents.

(iv) erythromycin analogues differing from the corresponding 'natural' compound in the stereochemistry of 'natural' methyl; and/or ring substituents other than methyl.

(v) erythromycin analogues having the features of two or more of sections (i) to (iv);
(vi) triketide lactone ("TKL") analogues:

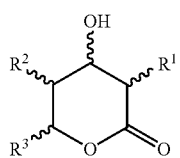
(I)

R$_3$ is the side-chain derived from the starter unit, and is subject to the variation described for the C-13 sidechain described above in (i).

R$_1$ and R$_2$ are "naturally" methyl but either or both may be replaced by hydrogen or ethyl (using extender units employing butyrate)

The natural stereochemistry is

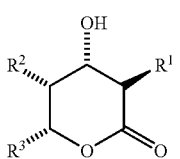
(II)

but any one or two or all of R$_1$, R$_2$, R$_3$ and OH may have the opposite stereochemistry. Generally TKL analogues can have variations as described for erythromycins in (i) to (v) above.
(vi) polyketides of types other than erythromyin, e.g. rapamycin or avermectin, having modifications corresponding to those described in sections (i) to (v).

For example, we have produced rapamycin variants using as added starter acids:

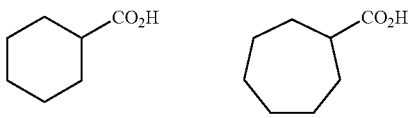

viii) truncated or extended versions of polyketide chains:
a) diketides R$^1$—CHOH—CHR$^2$—CO$_2$H
b) triketides R$^1$—CHOH—CHR$^2$—CHOH—CHR$^3$—CO$_2$H
c) tetraketides R$^1$—CHOH—CHR$^2$—CHOH—CHR$^3$—CHOH—CHR$^4$—CO$_2$H
d) penta-, hexa-, hepta- and larger ketide chains
The chains may have variants as described in (i) to (iv).
ix) ketide/non-ketide fusions.

Rapamycin is a natural example of a polyketide/peptide fusion. Means such as a peptide incorporating enzyme may be employed to create polyketides fused to one or more amino acids.
x) Polyketides (or fusions) cyclised by formation of lactones, hemiketals, ketals, lactams, or lactols.
xi) derivatives of any of the above which have undergone further processing by non-PKS enzymes, eg one or more of hydroxylation, epoxidation, glycosylation, and methylation.

The present invention provides a method of obtaining novel complex polyketides; and novel methods of increasing production of both new and known polyketides.

Thus in one type of embodiment of the invention, one or more segments of DNA encoding individual modules or domains within a natural Type I PKS (the "donor" PKS) have been used to replace the DNA encoding, respectively, individual modules or domains of another natural Type I PKS (the "acceptor" PKS). The total number of extension modules assembled in the hybrid PKS is not fixed, but the preferred number of such modules in any one multienzyme or cassette ranges between one, creating the smallest possible functional PKS, and six, which equals the largest number of consecutive nodules found to date to be housed in a single multienzyme of a natural Type I PKS, namely the rap PKS of *Streptomyces hygroscopicus*.

In a particularly preferred embodiment for the purposes of defining which hybrid PKS genes will be viable and productive, the acceptor PKS DNA consists of, or comprises of, the loading module, first two extension modules and chain-terminating thioesterase of the ery PKS, or other, preferably natural, type I PKS, housed in a suitable plasmid vector. Either one or more individual domains, or one or more individual modules, are specifically replaced by DNA encoding analogous domains or modules and derived from a different natural Type I PKS (the "donor" PKS).

The altered DNA sequence is introduced into a suitable microorganism and the genetically engineered microorganism is cultured under conditions suitable for polyketide production.

Surprisingly and unexpectedly, these genetically engineered microorganisms when cultured under suitable conditions have been found to produce non-natural analogues of the polyketide product(s) of the natural acceptor PKS, and where appropriate the products are found to undergo the same processing as the natural polyketide.

In this aspect of the invention, the plasmid vector may be any one drawn from a long list of plasmid vectors well known to be useful for cloning in *Streptomyces* and related Gram positive bacteria. It has been found particularly useful to select a low copy number plasmid vector with a broad host range based on the SCP2* plasmid of *Streptomyces coelicolor* M110. The construction is described herein of two SCP2*-derived plasmids particularly suitable for this purpose. A precursor plasmid in the construction of one of these two plasmids, lacking a streptomycete origin of replication but otherwise having the same features, is also particularly suitable. It is well known in the art that integration by homologous recombination can be achieved using such so-called suicide vectors, which only have an origin of replication active in *Escherichia coli*, in actinomycetes (Stimulation of erythromycin yield by integration of a chromosomal DNA fragment including the eryCI gene into the chromosome of *S. erythraea*, Hanel, F. et al. Biotechnology Letters (1993) 15:105-110; Insertion of plasmids into the chromosome of *Streptomyces griseofuscus*, Larson, J. L. and Hershberger, C. L. Plasmid (1990) 23:252-256; see also: Denaturation of circular or linear DNA facilitates integrative transformation of *Streptomyces coelicolor* A3(2): possible relevance to other organisms, Oh, S. H. and Chater, K. F. (1997) J. Bacteriol 179:122-127. )The triketide lactone synthase of the "acceptor" PKS may be composed of loading modules, extension modules and chain-terminating activities drawn from any natural or non-natural Type I PKS, but particularly suitable for this purpose are the components of Type I PKSs for the biosynthesis of erythromycin, rapamycin, avermectin, tetronasin, oleandomycin, monensin, amphotericin and rifamycin, for all of which the gene and modular organisation is known through gene sequence analysis, at least in part. Particularly favourable examples of the loading modules of the donor PKS are those loading modules showing a relaxed specificity, for example the loading module of the avermectin (avr)-producing PKS of *Streptomyces avermitilis;* or those loading modules possessing an unusual specificity, for example the loading modules of the rapamycin-, FK506- and ascomycin-producing PKSS, all of which naturally accept a shikimate-derived starter unit.

Genetically-engineered cells suitable for expression of hybrid Type I PKS genes may be drawn from any actinomycete capable of maintaining the vector in either autonomous or integrated form. Particularly effective hosts are *Saccharopolyspora erythraea, Streptomyces coelicolor, Streptomyces avermitilis, Streptomyces griseofuscus, Streptomyces cinnamonensis, Micromonospora griseorubida, Streptomyces hygroscopicus, Streptomyces fradiae, Streptomyces longisporoflavus, Streptomyces lasaliensis, Streptomyces tsukubaensis, Streptomyces griseus, Streptomyces venezuelae, Streptomyces antibioticus, Streptomyces lividans, Streptomyces rimosus* and *Streptomyces albus*. These include hosts in which SCP2*-derived plasmid vectors are known to replicate autonomously, as for example *S. coelicolor, S. avermitilis* and *S. griseofuscus;* and other hosts such as *Saccharopolyspora erythraea* in which SCP2*-derived plasmids become integrated into the chromosome through homologous recombination between sequences on the plasmid insert and on the chromosome; and all hosts which are integratively transformed by suicide plasmid vectors.

In a further aspect of the present invention, a plasmid containing "donor" PKS DNA is introduced into a host cell under conditions where the plasmid becomes integrated into an acceptor PKS genes on the bacterial chromosome by homologous recombination, to create a hybrid PKS. A preferred embodiment is when the donor PKS DNA includes a segment encoding a loading module, in such a way that this loading module becomes linked to the acceptor PKS genes on the chromosome. Such a hybrid PKS produces valuable and novel hybrid polyketide products when cultured under suitable conditions as described herein. Specifically, when the loading module of the acceptor PKS is replaced by the loading module of the avermectin-producing (avr) PKS, the hybrid polyketide products contain a starter unit typical of those used by the avr PKS. Thus when the loading module of the ery PKS is replaced by the avr loading module, *Saccharopolyspora erythraea* strains containing such hybrid PKS are found to produce 14-membered macrolides containing starter units typically used by the avr PKS.

It is very surprising and unexpected that the 14-membered macrolide polyketides produced by such recombinant cells of *S. erythraea* are found to include derivatives of erythromycin A, showing that the several processing steps required for the transformation of the products of the hybrid PKS into novel and therapeutically valuable erythromycin A derivatives are correctly carried out.

A further aspect of the present invention is the unexpected and surprising finding that transcription of any of the hybrid Type I PKS genes, whose construction is described herein, can be specifically increased when the hybrid genes are placed under the control of a promoter for a Type II PKS gene linked to a specific activator gene for that promoter. It is particularly remarkable that when a genetically engineered cell containing hybrid Type I genes under such control is cultured under conditions suitable for polyketide production, significantly enhanced levels of the hybrid polyketide are produced.

Such specific increases in yield of a valuable polyketide product are also seen for natural polyketides produced by a Type I PKS placed under the control of a Type II PKS promoter and activator gene. In a preferred embodiment, Type I PKS genes present on an SCP2*-derived plasmid or a precursor plasmid lacking only the streptomycete origin of replication, are placed under the control of the actI promoter derived from the actinorhodin biosynthetic gene cluster of *Streptomyces coelicolor*, and in which the vector also contains the structural gene encoding the specific activator protein Act II-orf 4. The recombinant plasmid is introduced into bacterial hosts other than *Streptomyces coelicolor* chosen from *Streptomyces* and related genera, under conditions where either the introduced PKS genes, or PKS genes already present in the host strain, are expressed under the control of the actI promoter.

The recombinant strains produce the desired specific polyketide product and the activator gene requires only the presence of the specific promoter in order to enhance transcriptional efficiency from the promoter. This is particularly surprising in that activators of the ActII-orf4 family do not belong to a recognised class of DNA-binding proteins. Therefore it would be expected that additional proteins or other control elements would be required for activation to occur in a heterologous host not known to produce actinorhodin or a related isochromanequinone pigment. It is also surprising and useful that the recombinant strains produce up to 10-fold more specific polyketide product than when the same PKS genes are under the control of the natural promoter, and the specific polyketide product is also produced precociously in growing culture, rather than only during the transition from growth to stationary phase. Such polyketides are useful as antibiotics, anti-cancer agents, immunosuppressants and for many other purposes in human and veterinary medicine.

When the genetically engineered cell is *Saccharopolyspora erythraea*, the activator and promoter are derived from the actinorhodin PKS gene cluster and the actI/actII-orf4-regulated ery PKS gene cluster is housed in the chromosome, following the site-specific integration of a plasmid vector, culturing of these cells under suitable conditions produces up to ten fold more total 14-membered macrolide product than in a comparable strain not under such heterologous control. When in such a genetically engineered cell of *S. erythraea* the PKS genes under this heterologous control are hybrid Type I PKS genes whose construction is described herein, then again up to ten-fold more hybrid polyketide product is obtained compared to the same hybrid Type I PKS genes not under such control. Specifically, when the hybrid Type I PKS genes are the ery PKS genes in which the loading module is replaced by the avr loading module, a ten-fold increase is found in the total amounts of novel 14-membered macrolides produced by the genetically engineered cells when cultured under suitable conditions as described herein. The ability of a modular polyketide synthase to function in a cell-free system has been disclosed, for the DEBS1-TE system of *Saccharopolyspora erythraea* (Leadlay, P. F. Lecture to 9th International Symposium on the Biology of Actinomycetes, Moscow, July 10-15 (1994) S7-2; Wiesmann, K. E. et al. Poster presentation P2-02, p 154, Abstracts of the 9th International Symposium on the Biology of Actinomycetes, Moscow, July 10-15 (1994); Wiesmann, K. E. et al. (1995) Chem. and Biol. 2:583-589) and for the production of 6-deoxyerythronolide B by DEBS1, DEBS2 and DEBS3 (Pieper et al. (1995) Nature 378:263-266.). Accordingly, the surprising and unexpected ability of the actII-orf4 gene to activate the actI promoter in *S. erythraea* and to do so more effectively than in its native host strain, naturally leads to a corresponding impressive and valuable increase in the amount of active DEBS enzymes produced by the recombinant *S. erythraea* strains as described herein.

The suitable and preferred means of growing the genetically engineered cells, and the preferred means of isolating both the natural and the hybrid polyketides are described more fully in the Examples.

Some embodiments of the invention will now be described with reference to the accompanying drawings in which:

FIG. 1 gives the chemical formulae of three known polyketides;

Figure 10A:
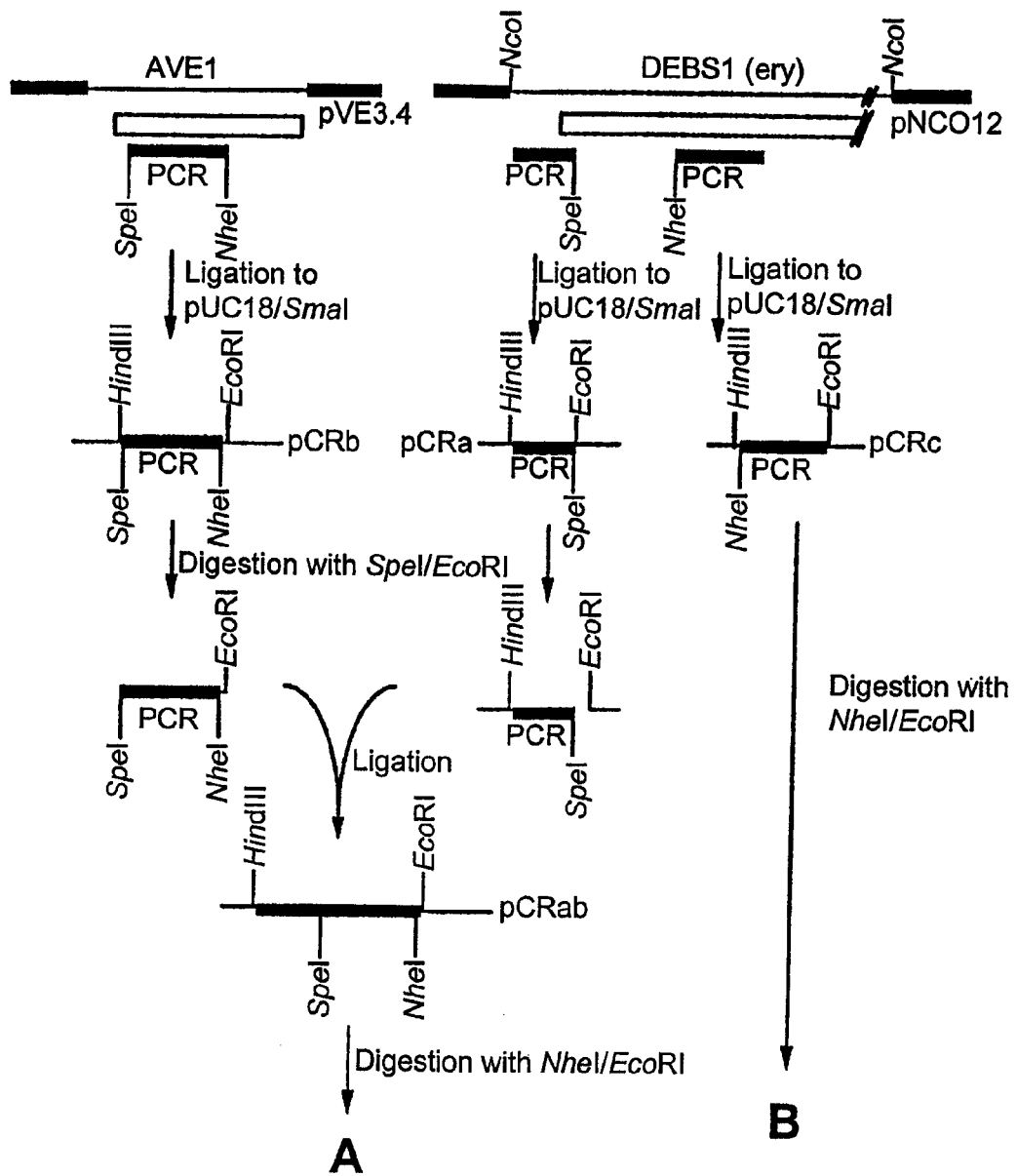
Figure 11:
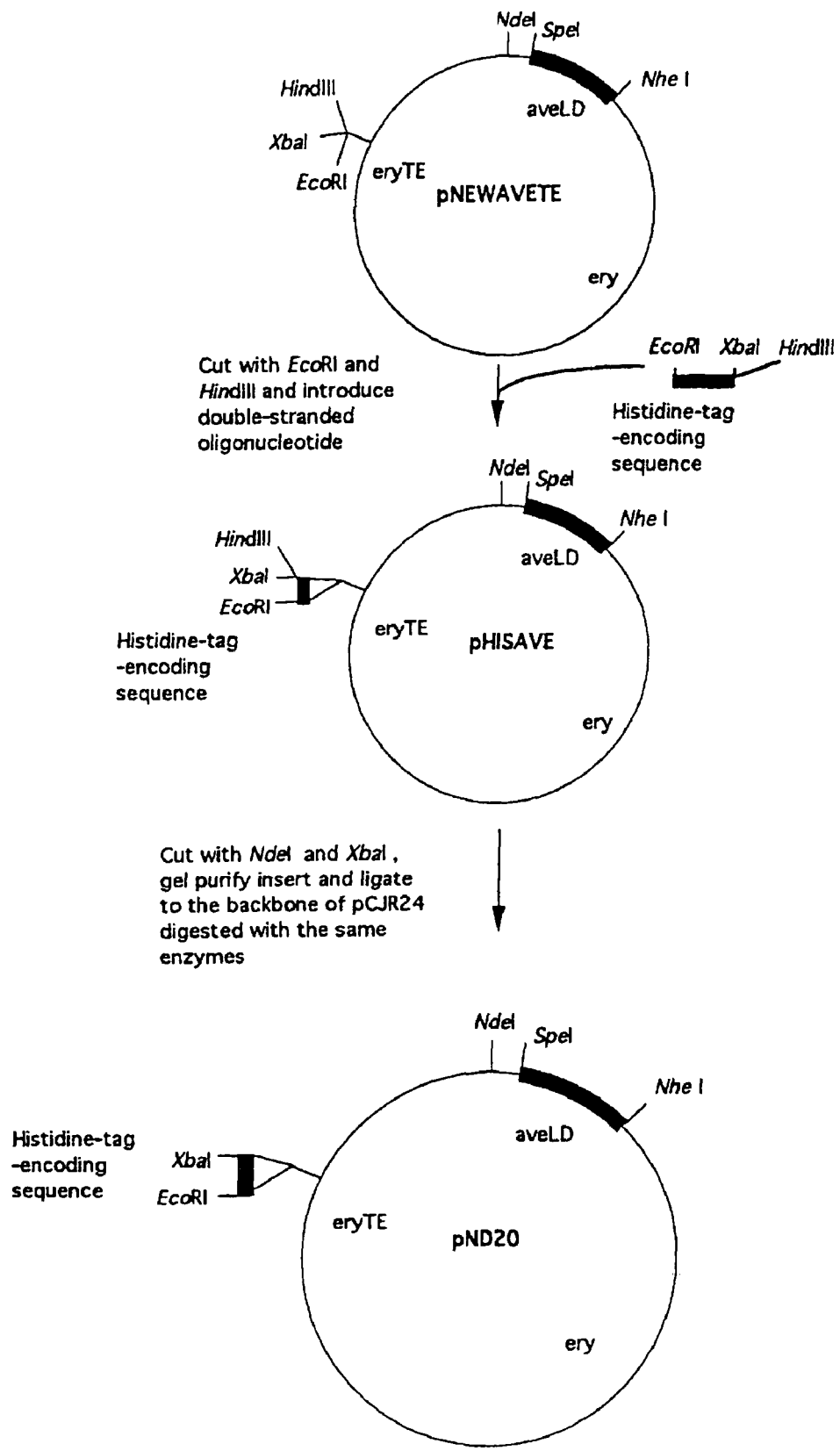
Figure 12:
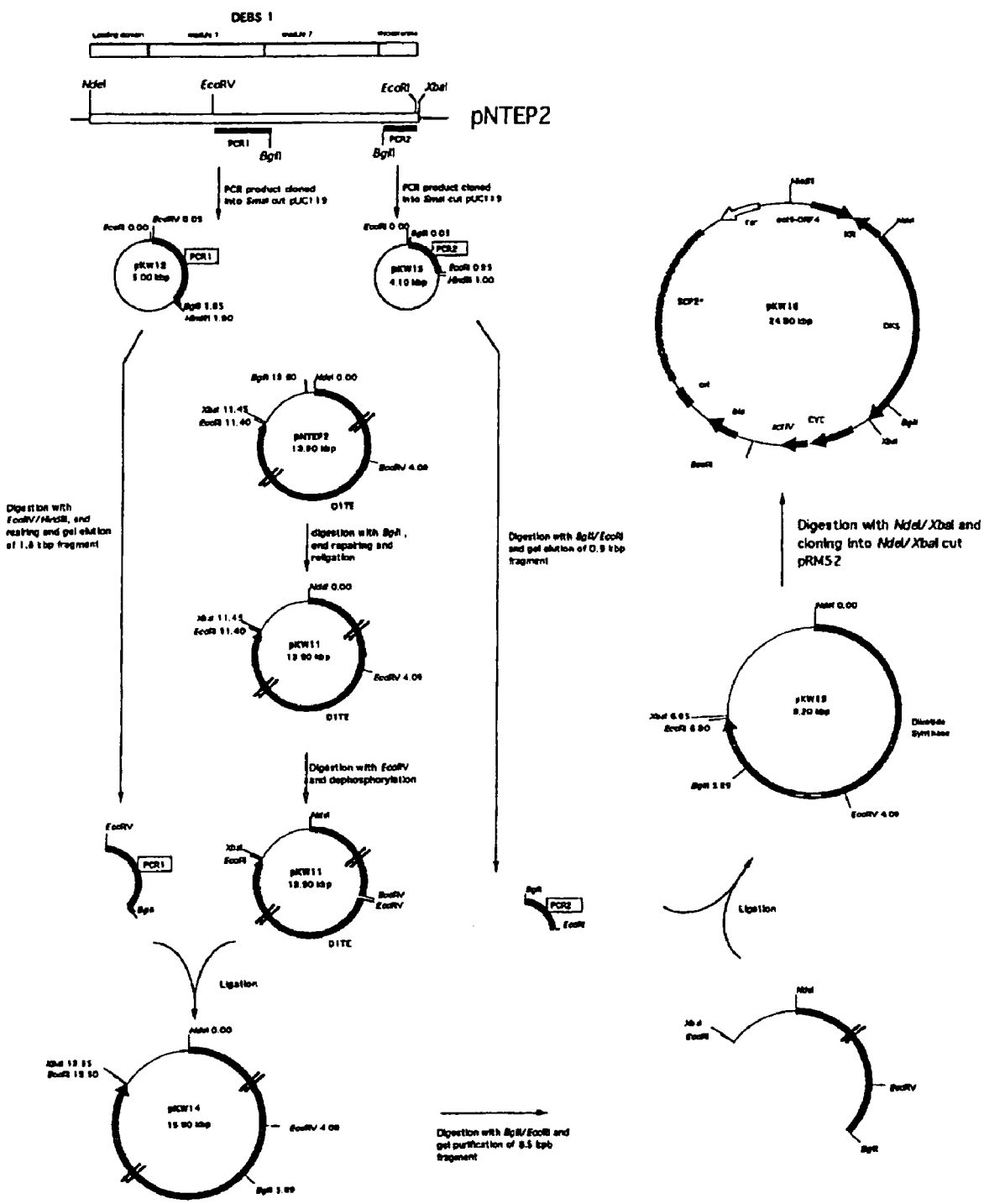
Figure 12A:
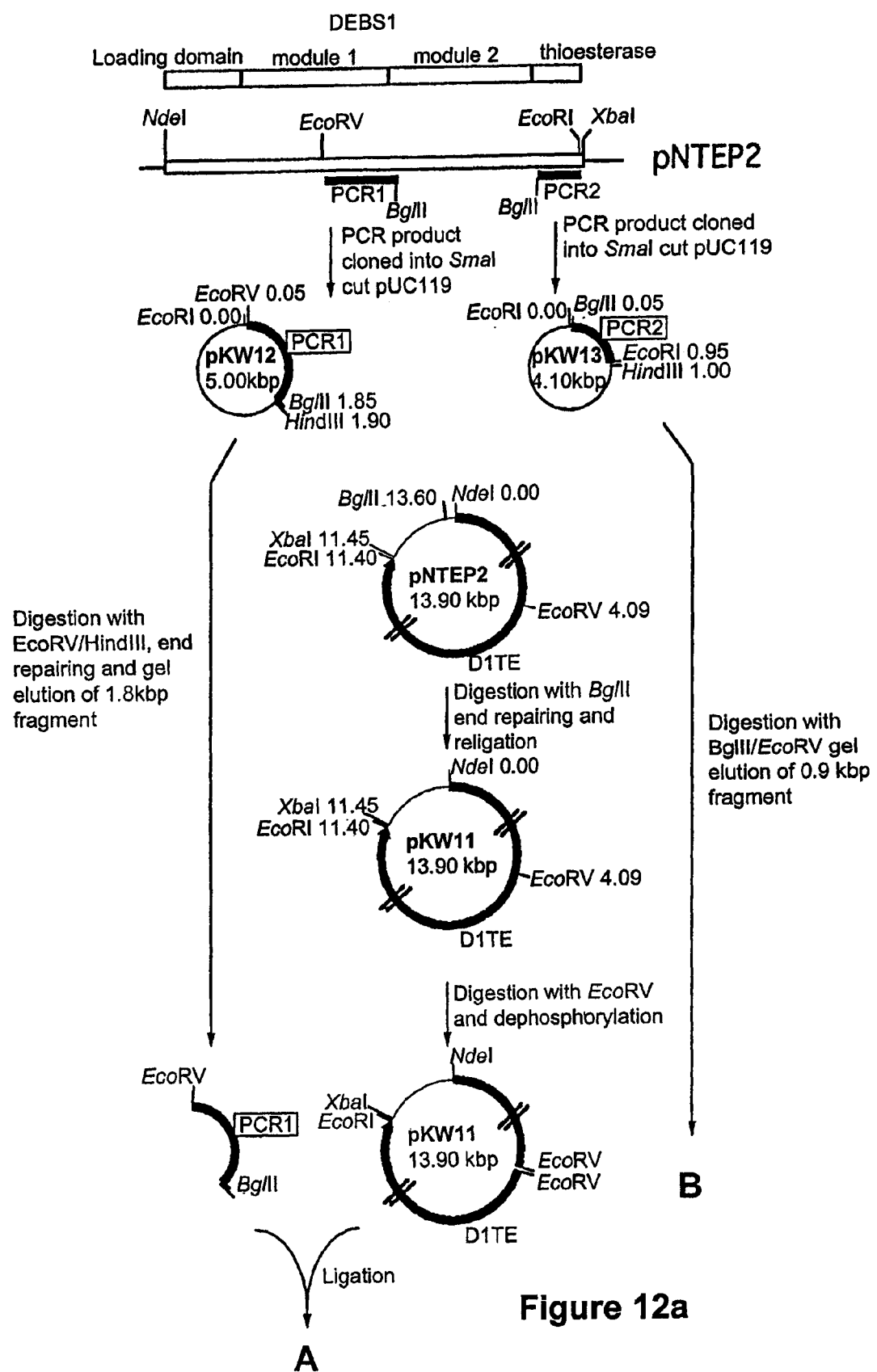
Figure 12B:
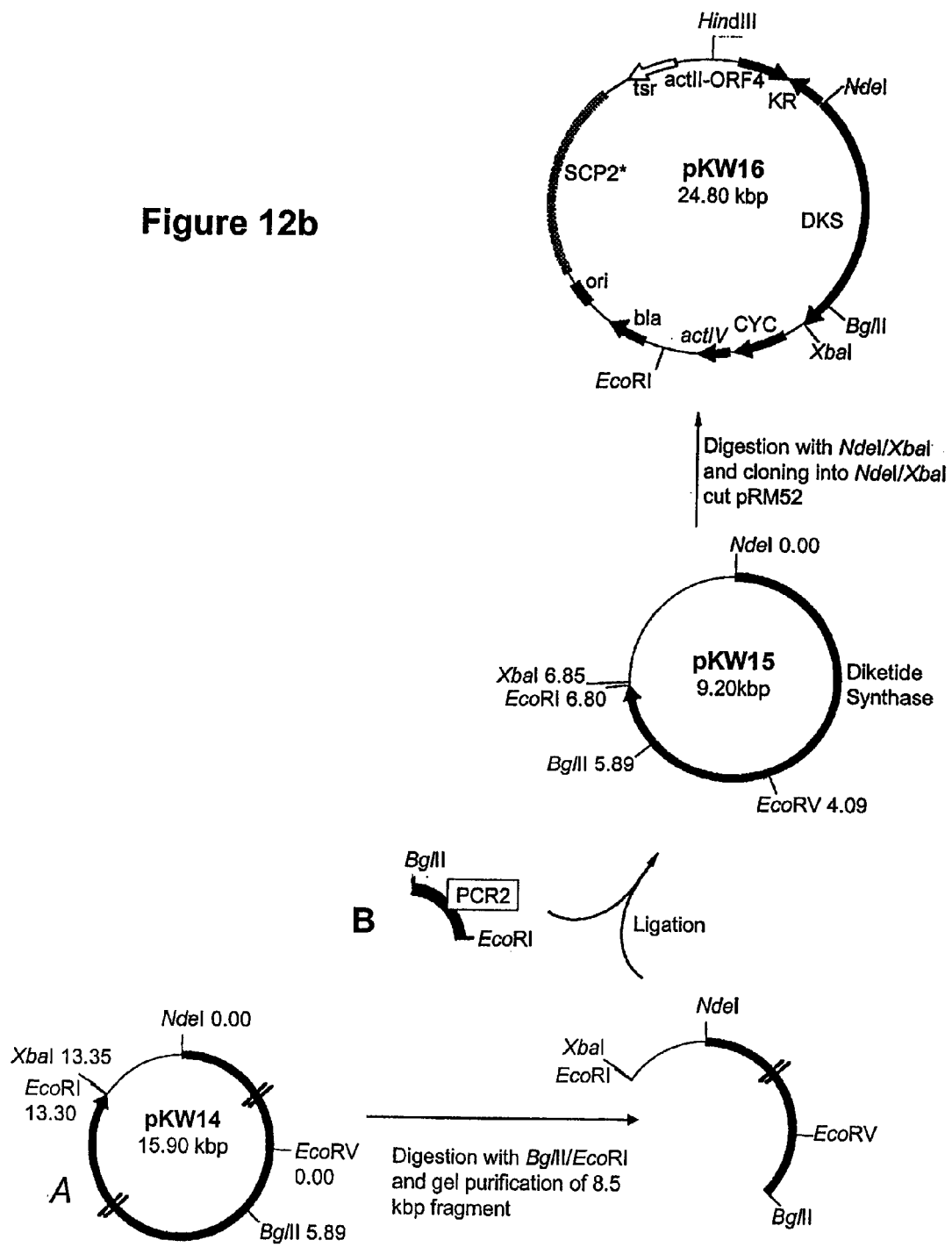
Figure 13:
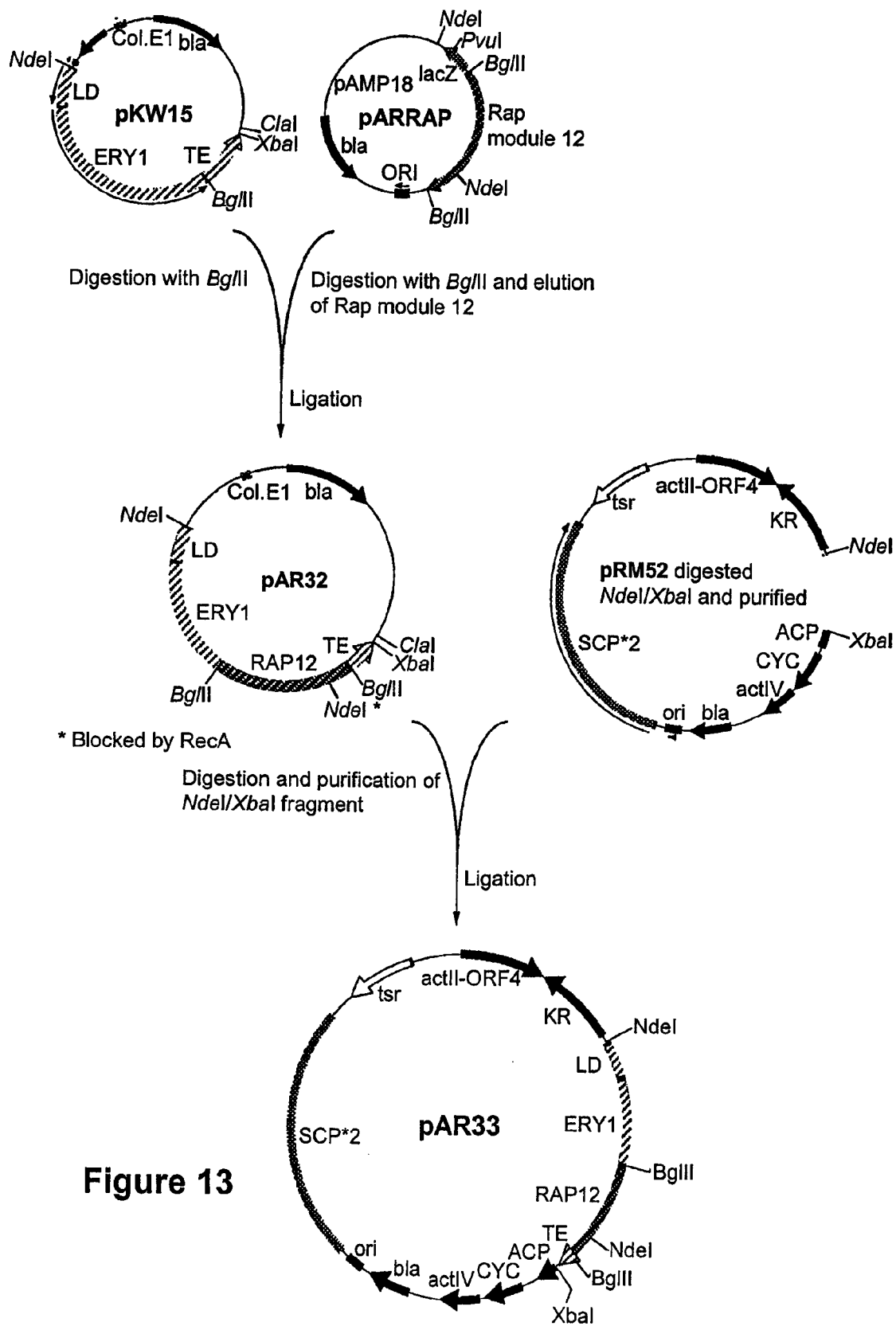
Figure 14A:
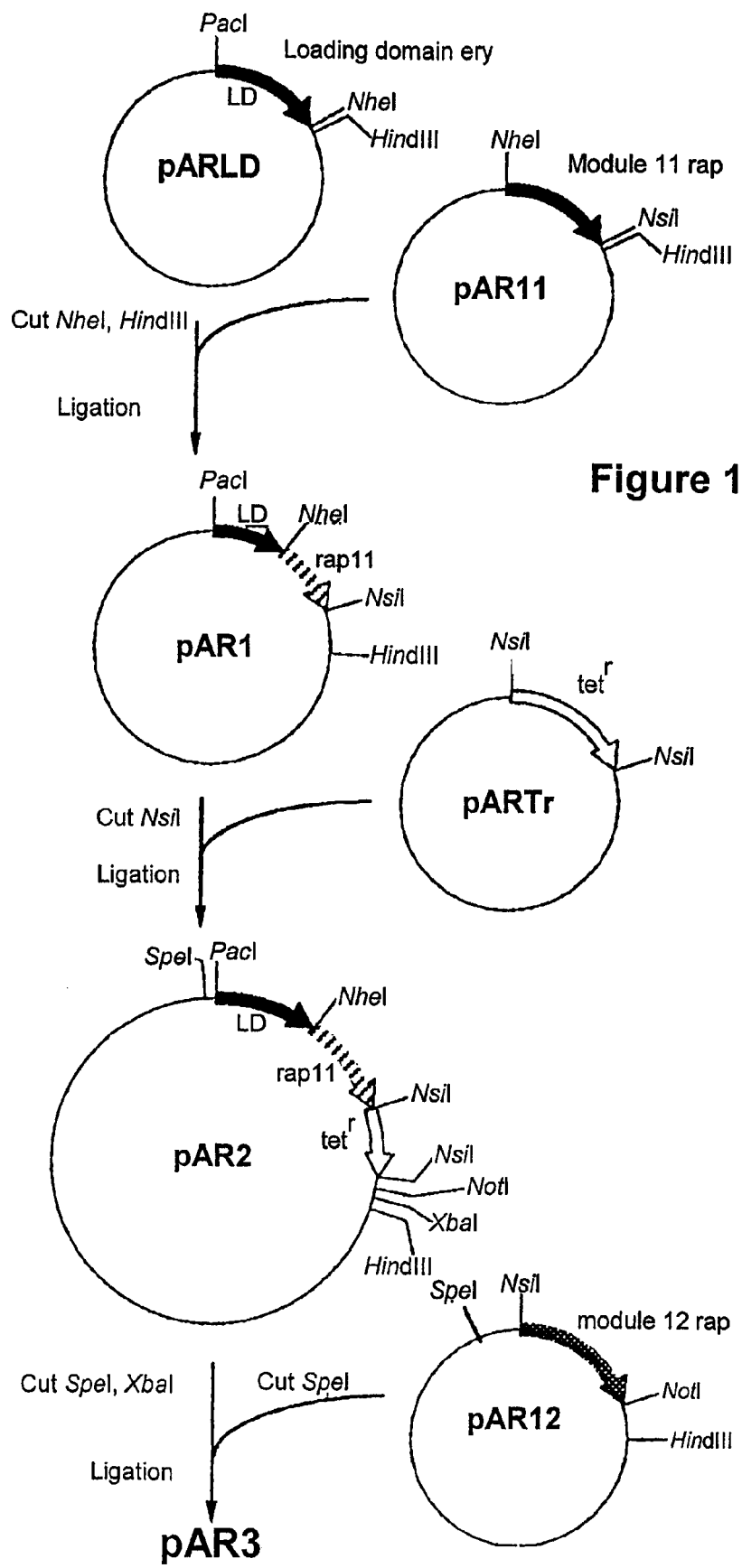
Figure 14B:
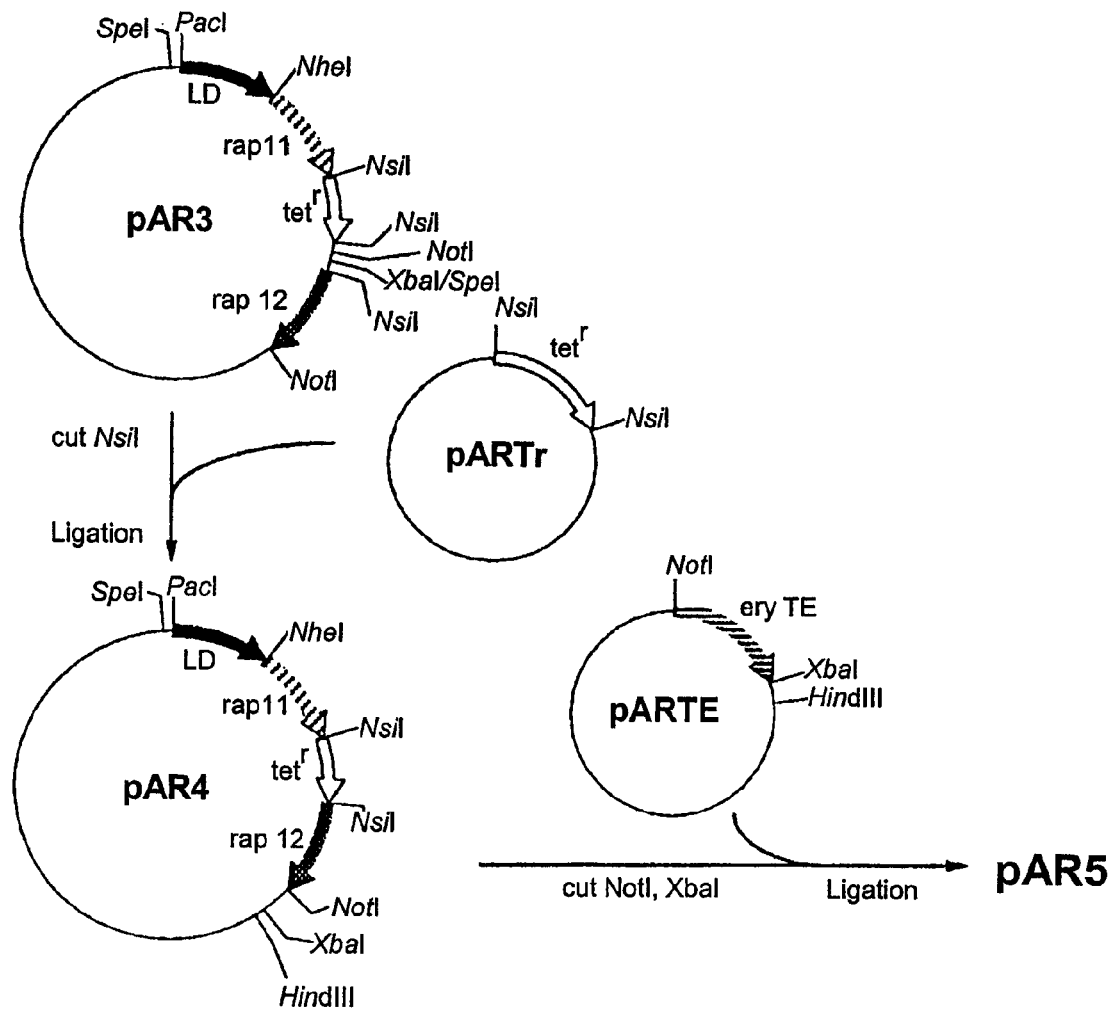
Figure 14C:
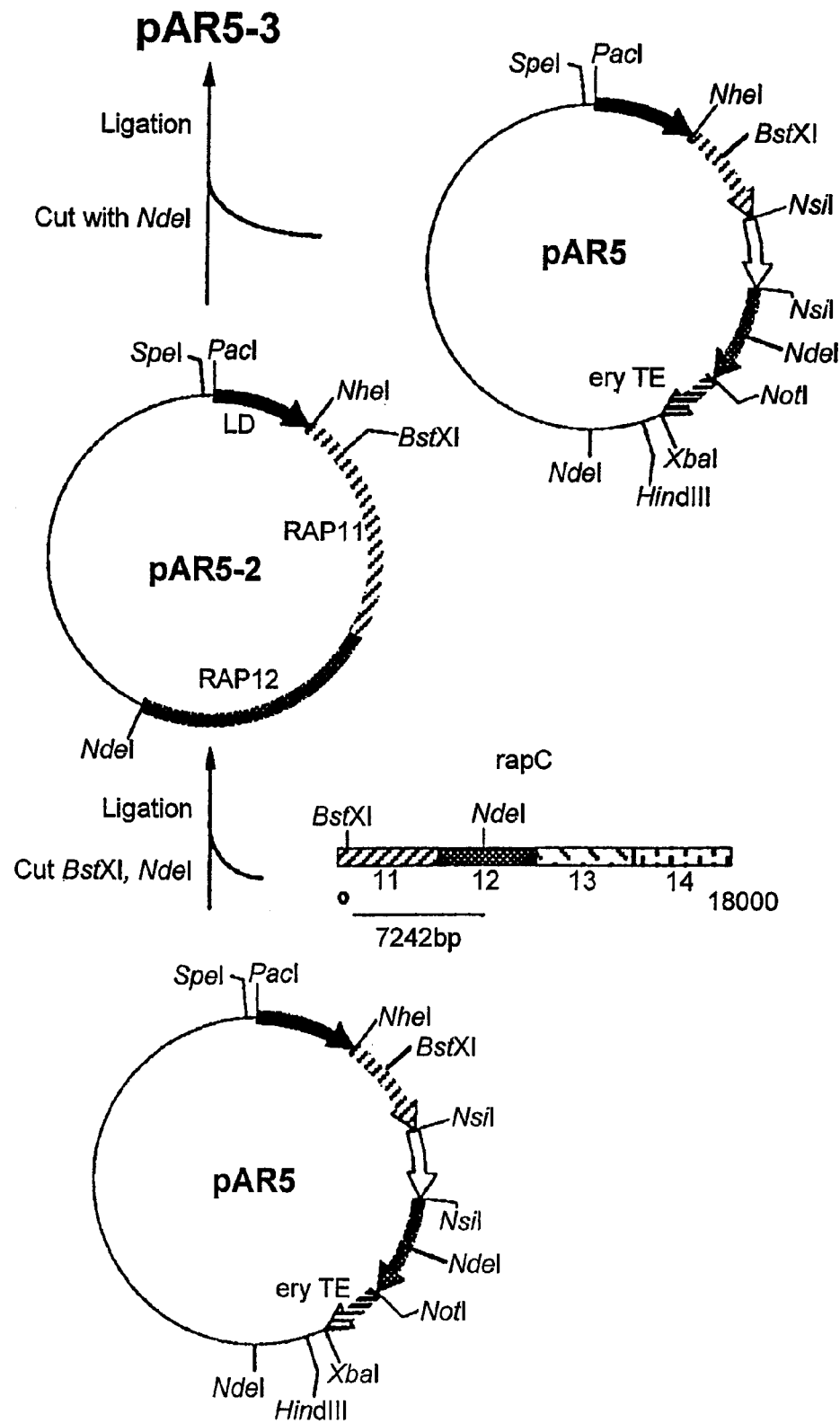
Figure 14D:
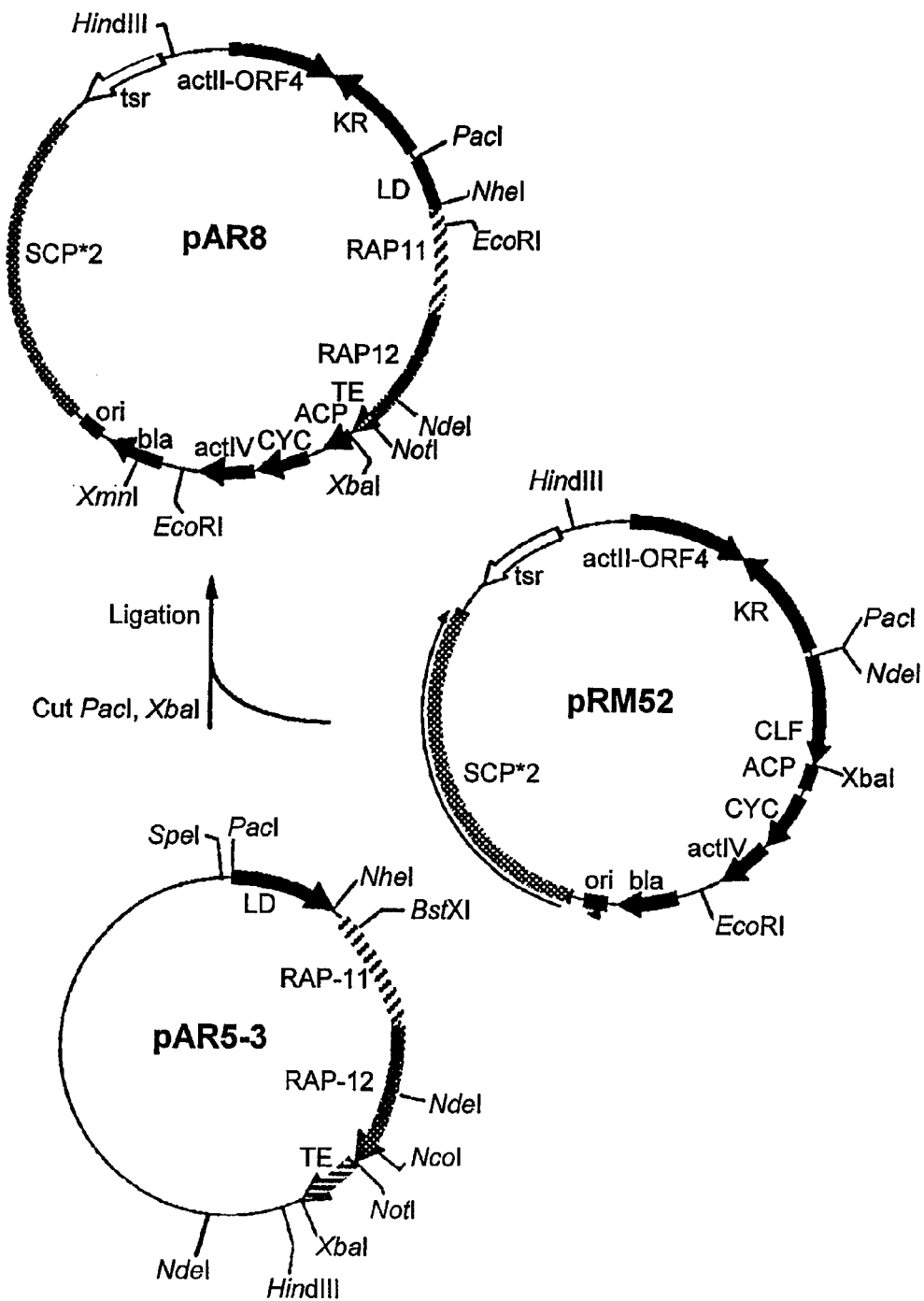
Figure 15:
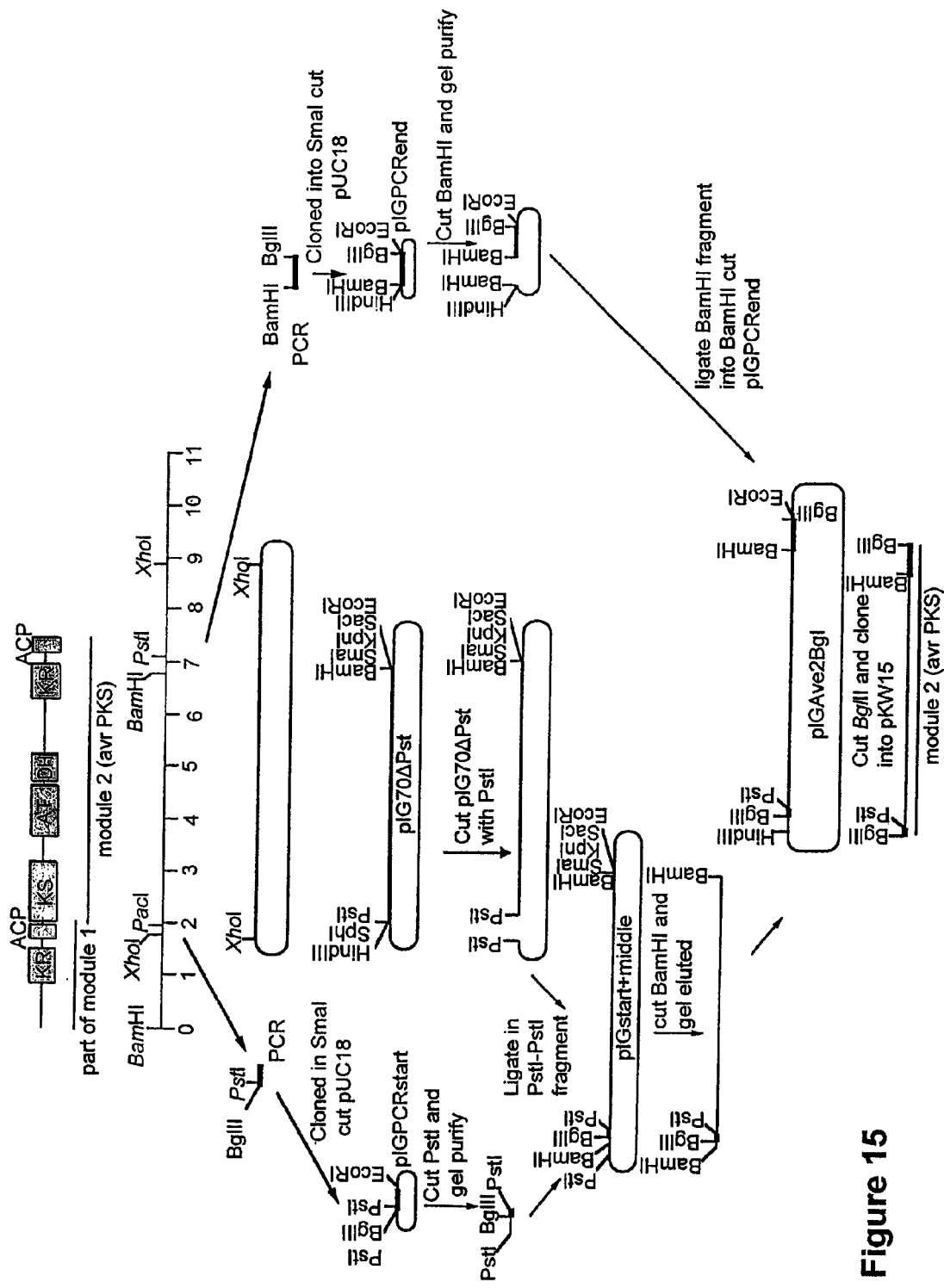
Figure 16:
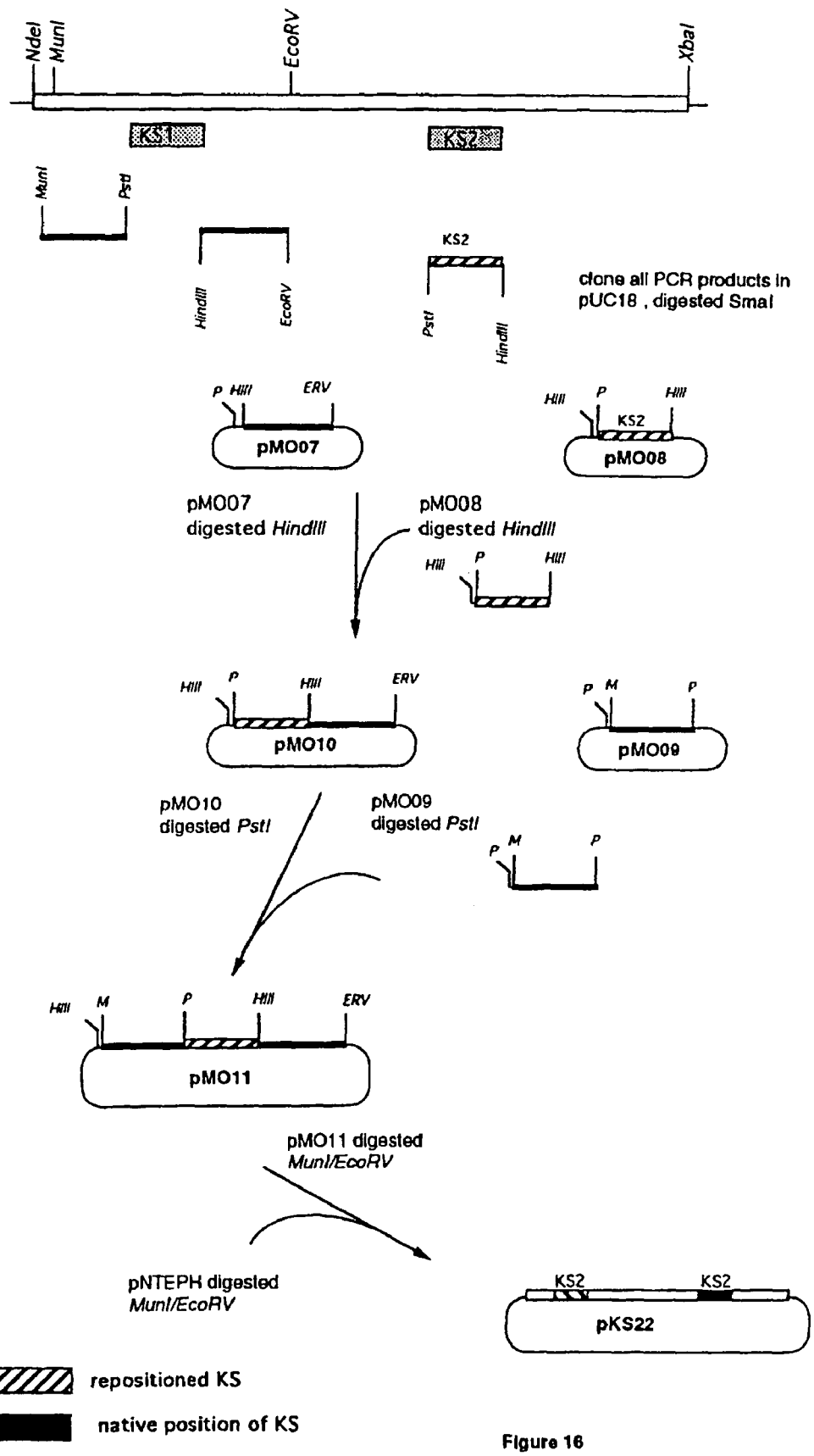
Figure 17A:
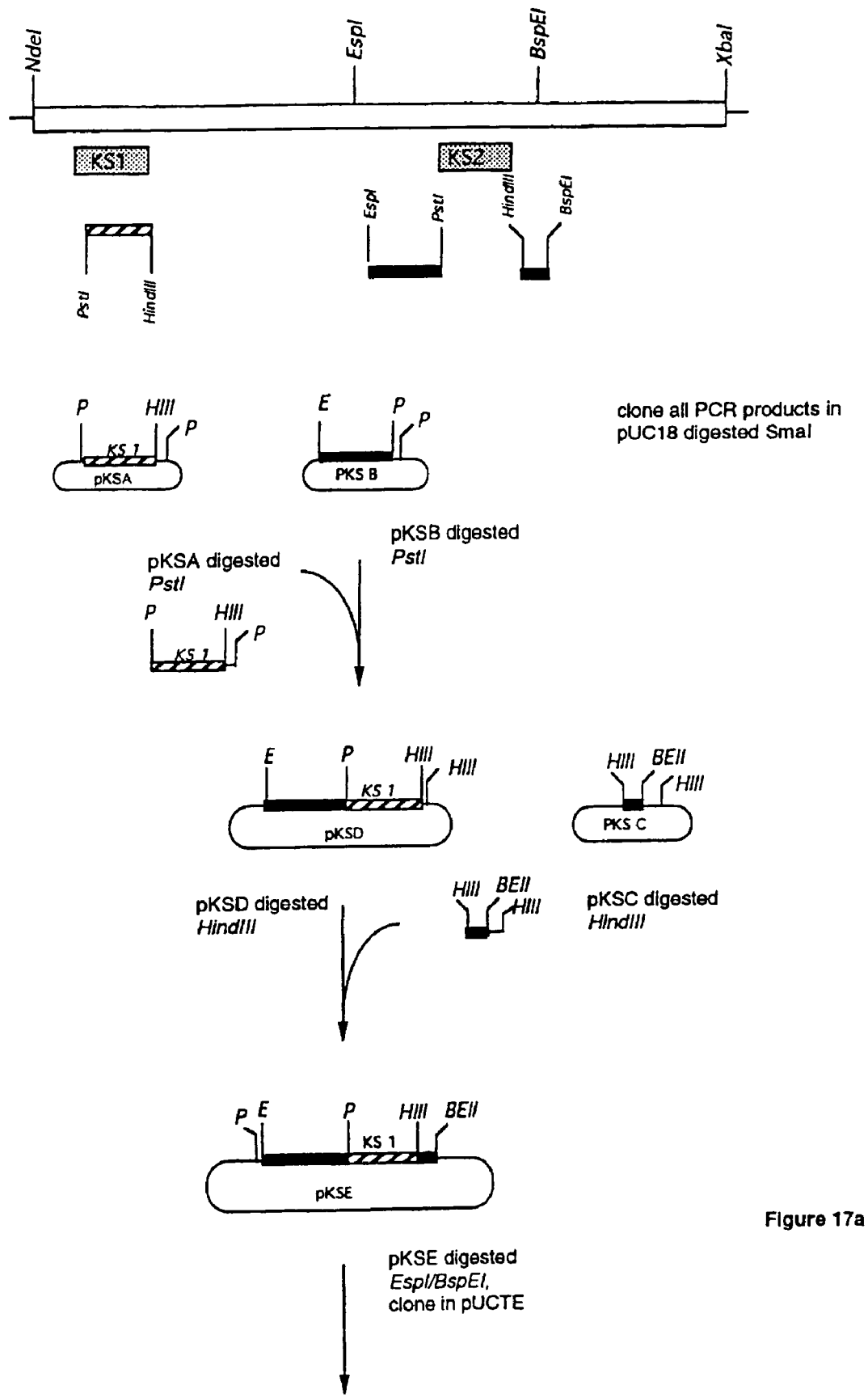
Figure 17B:
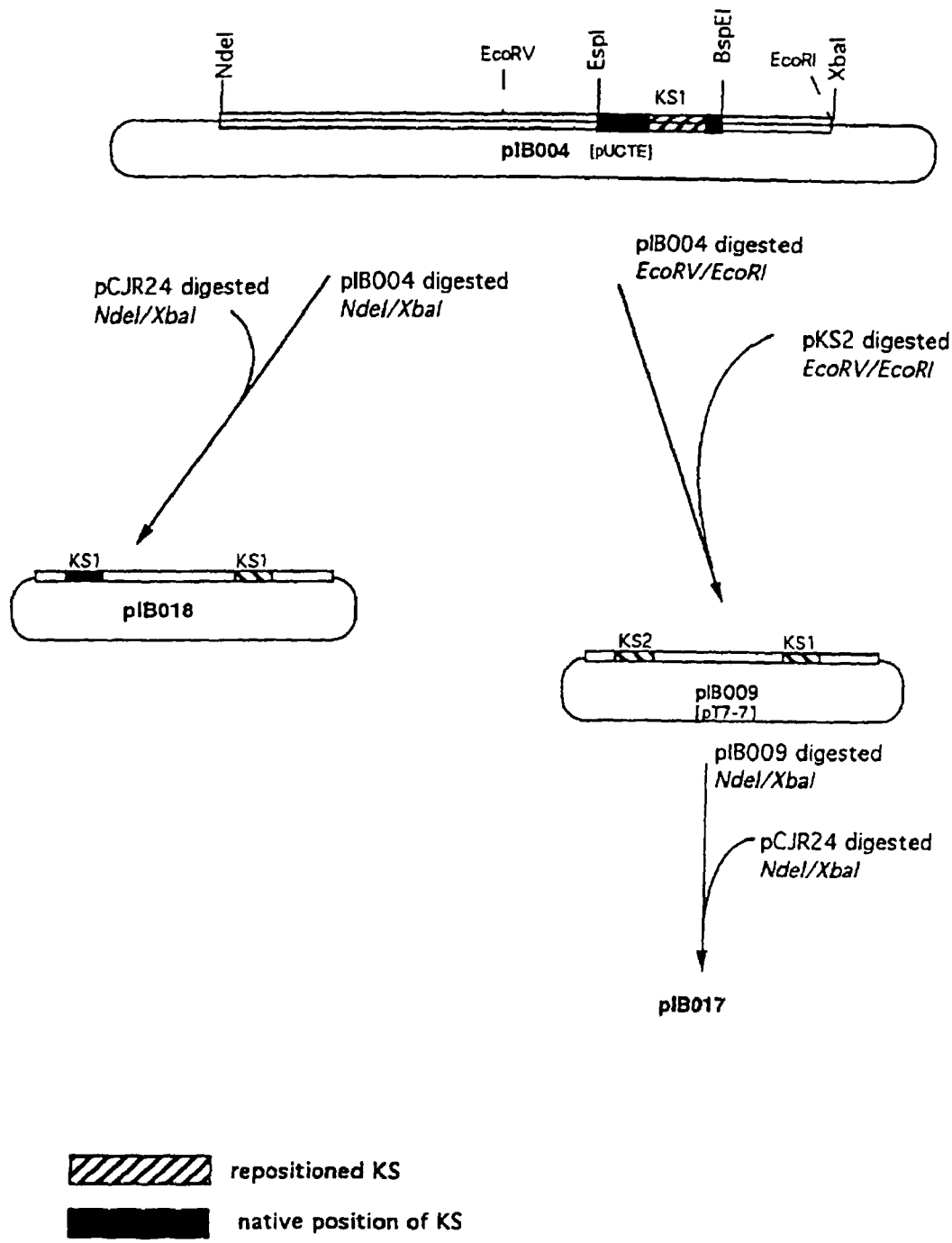
Figure 18:
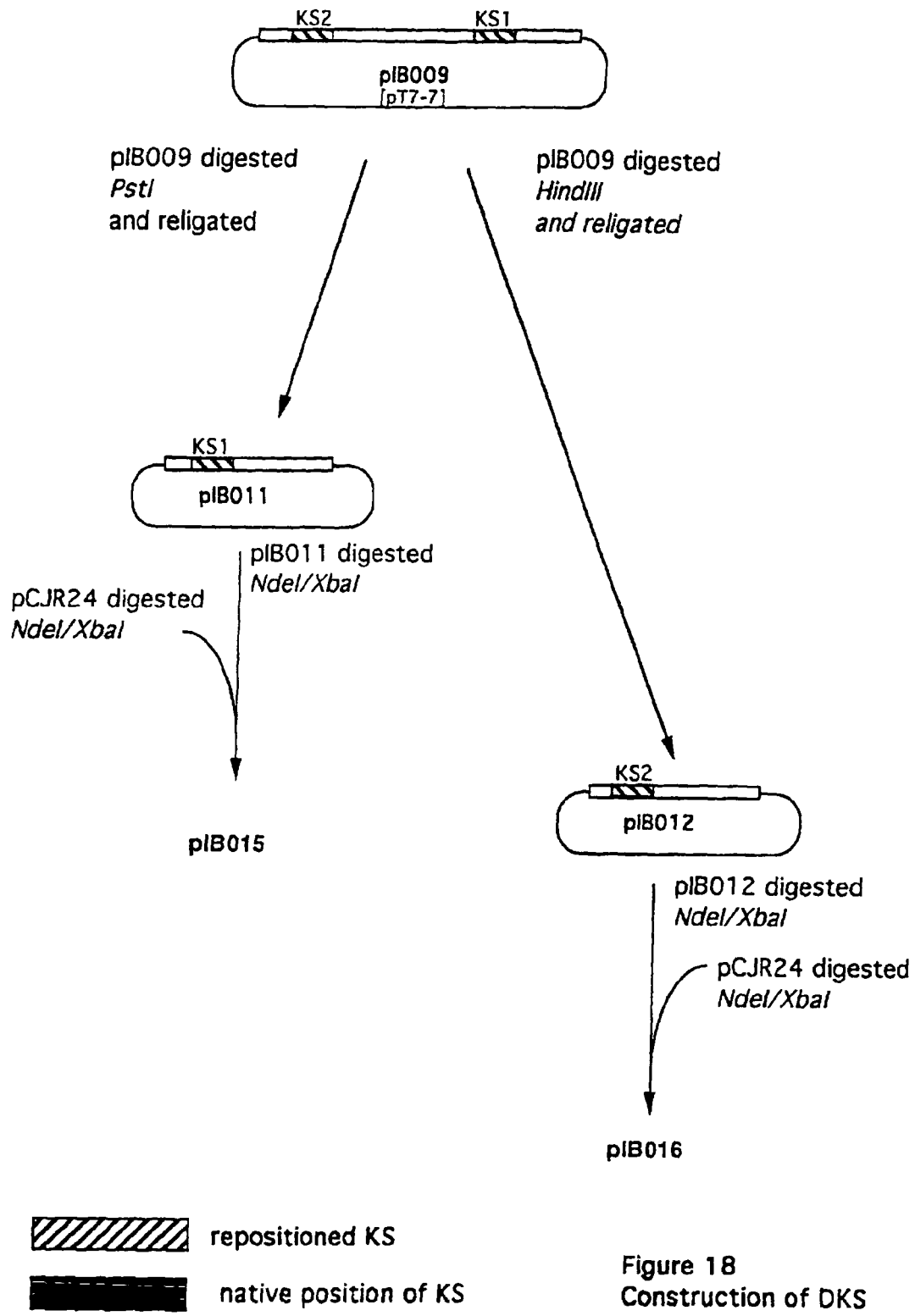
Figure 19:
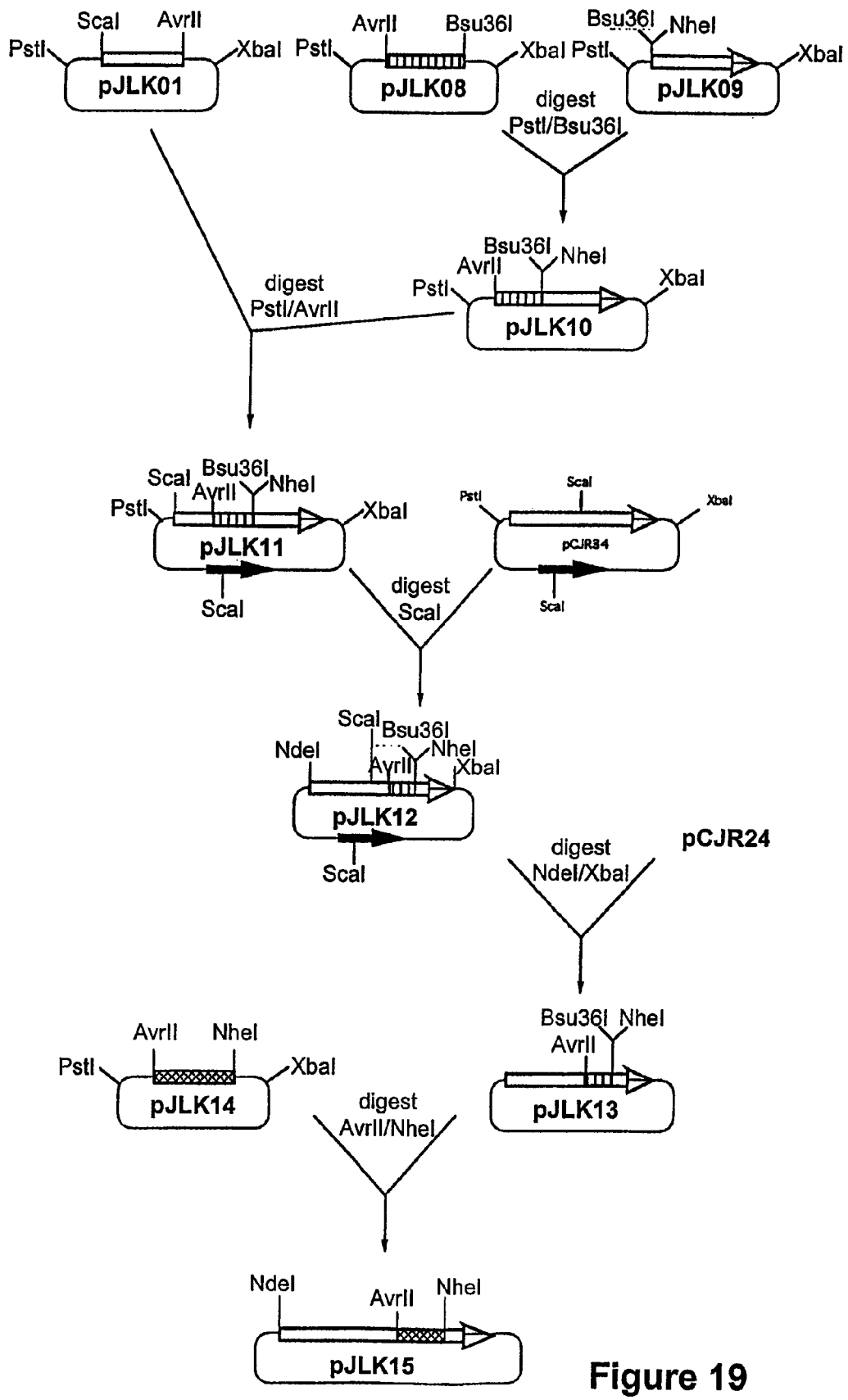
Figure 20:
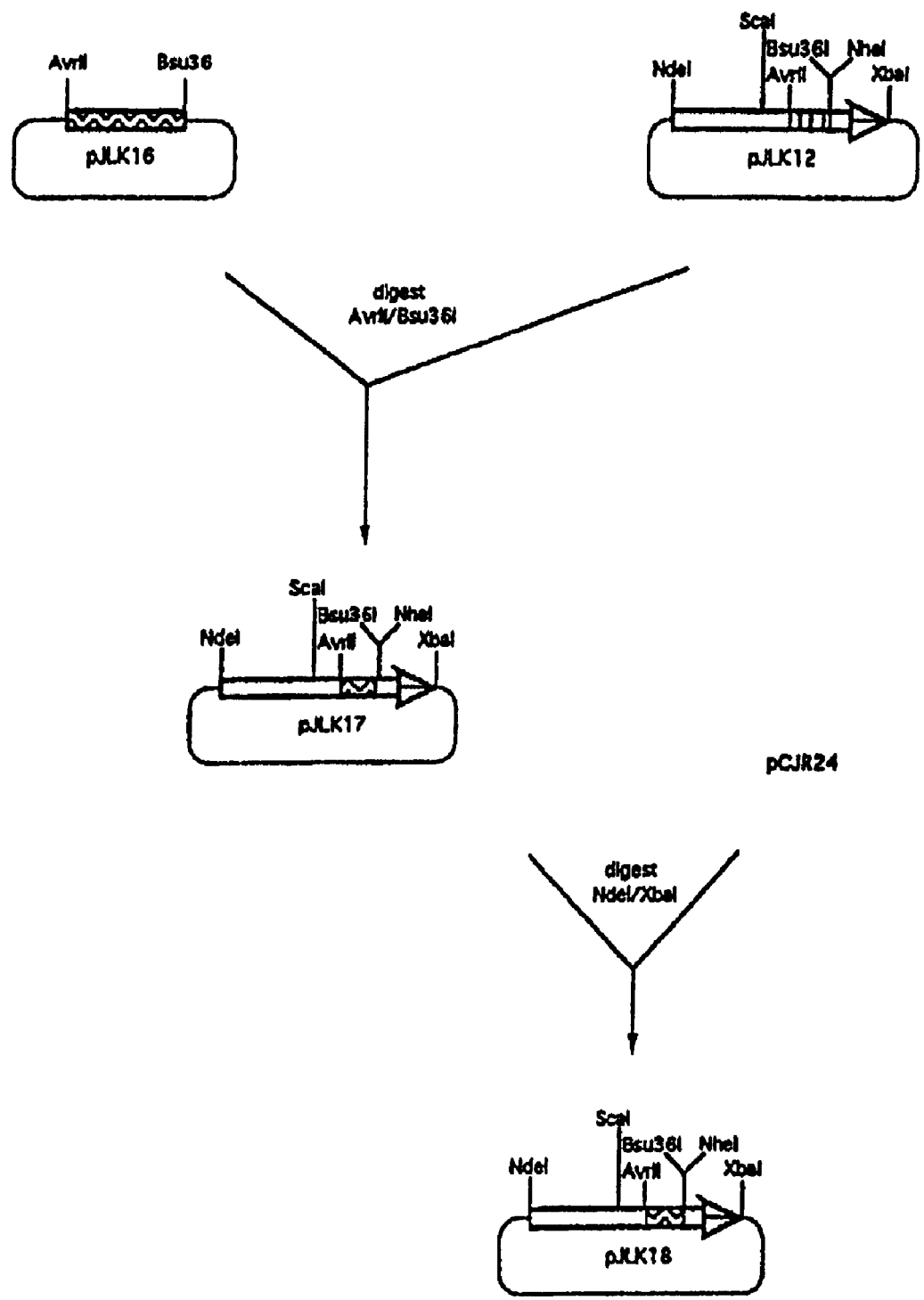
Figure 21:
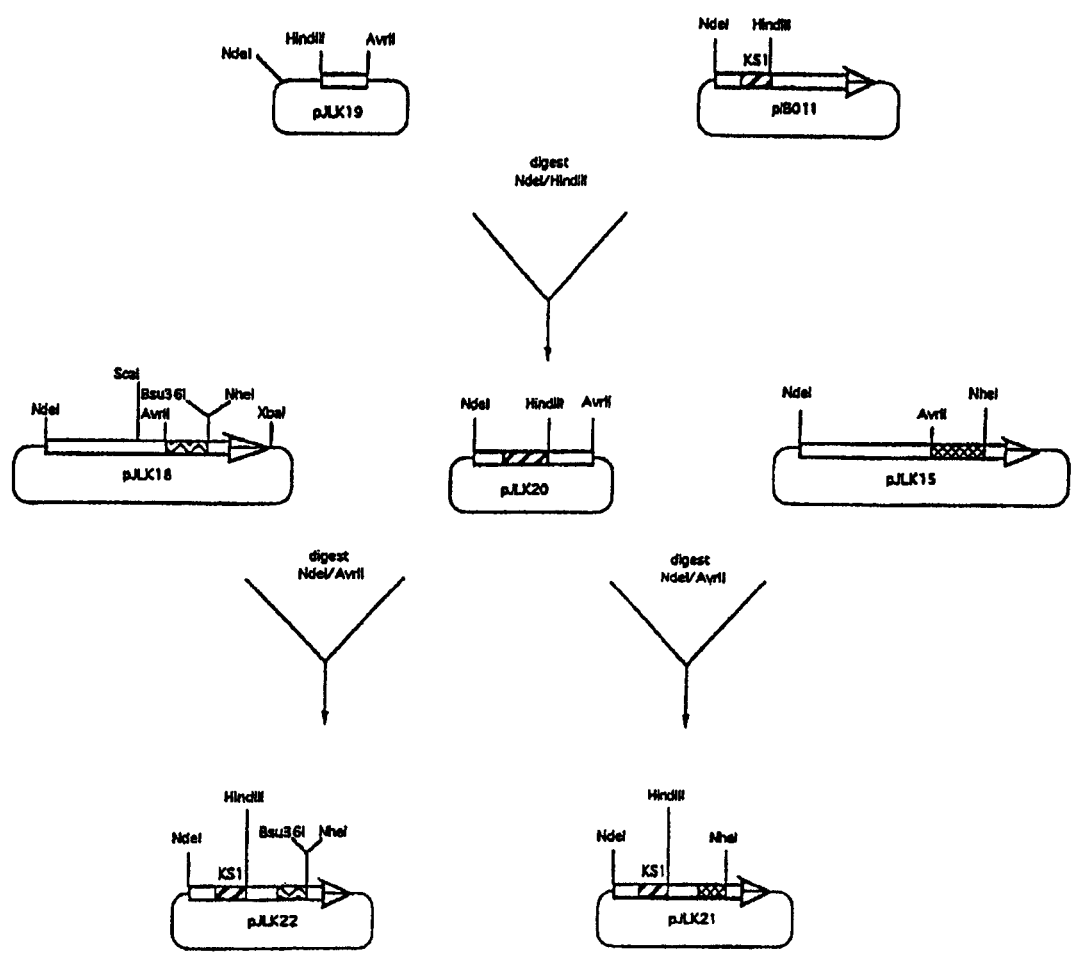
Figure 22:
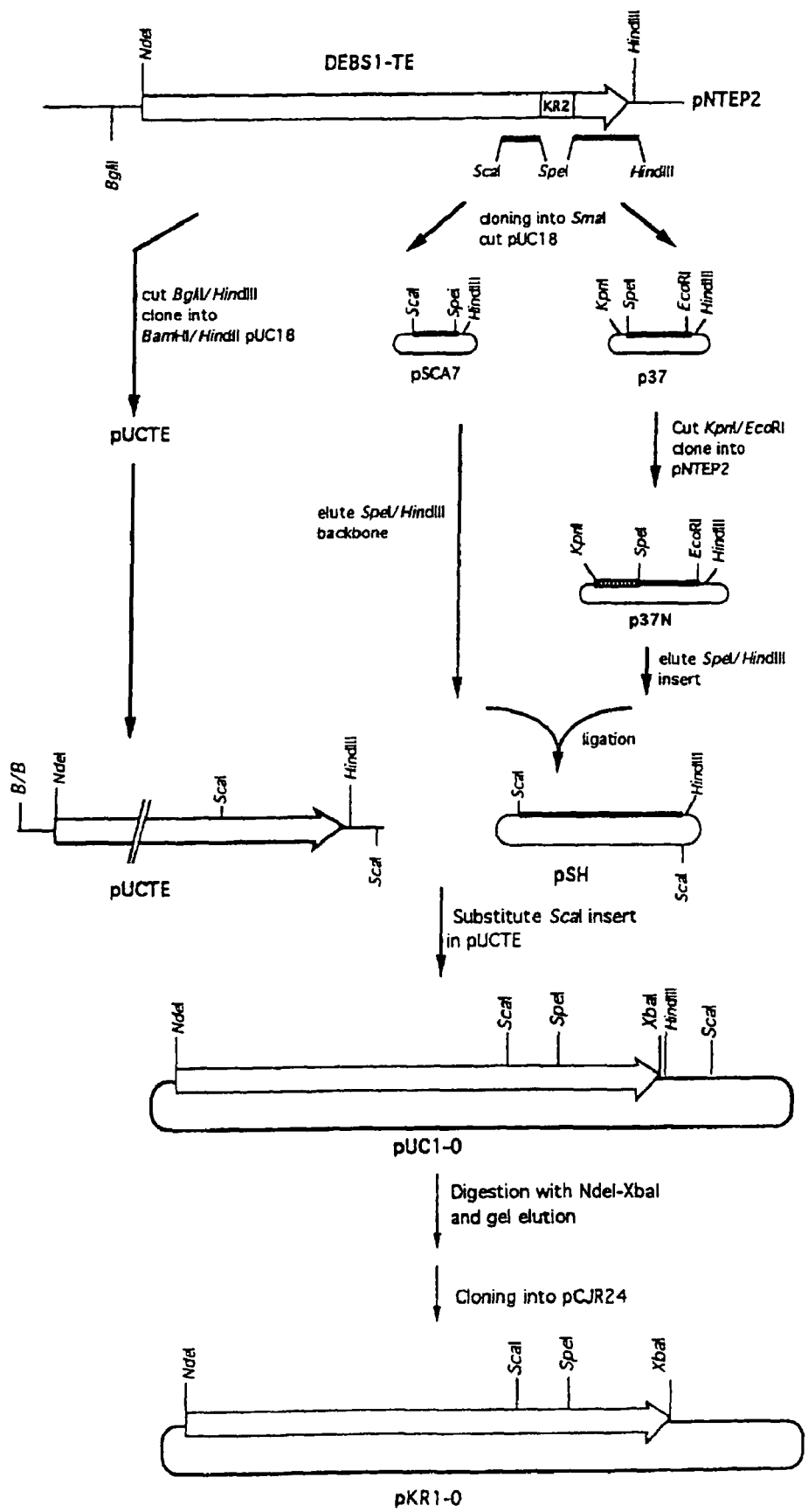
Figure 23:
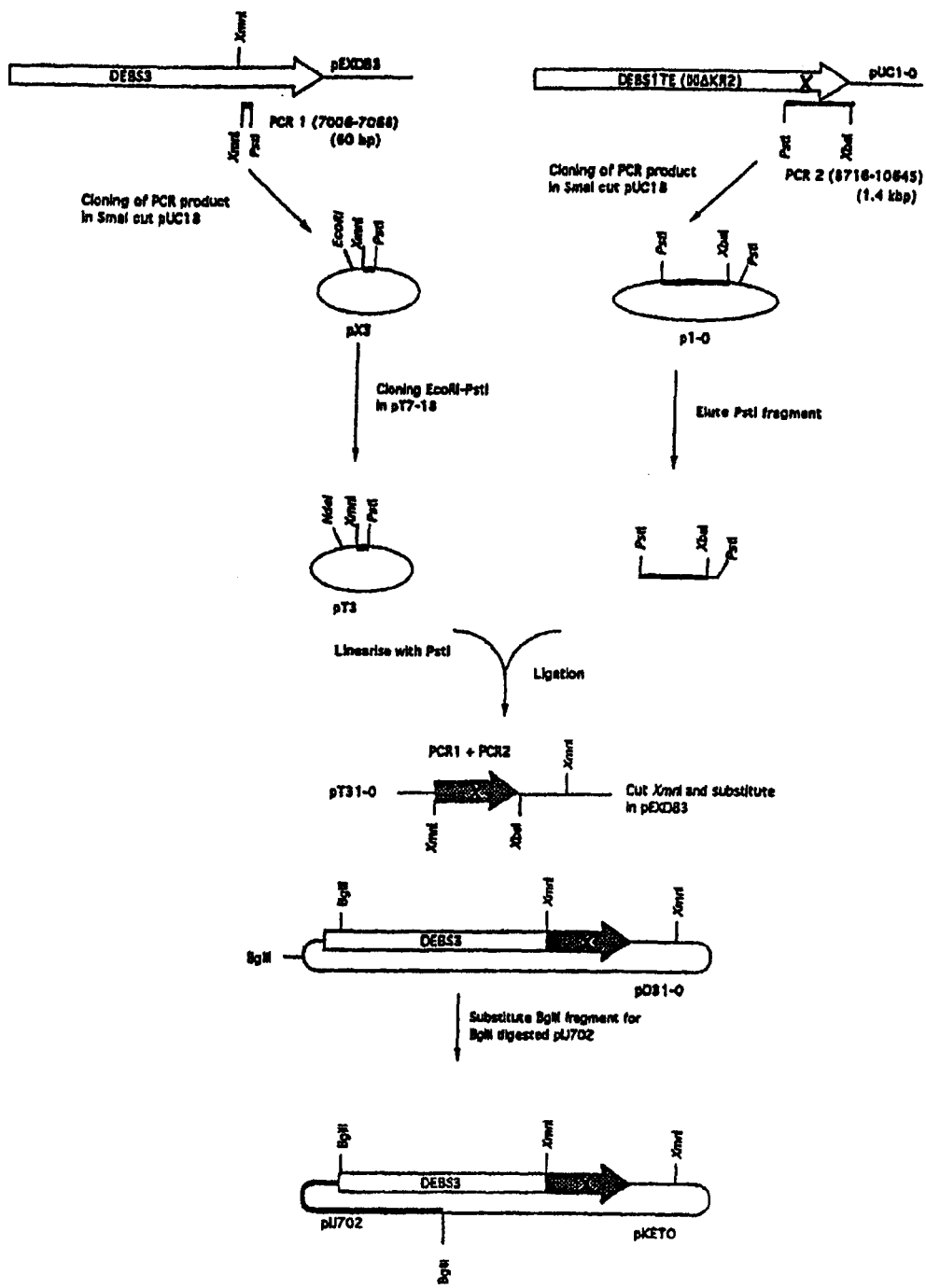
Figure 24:
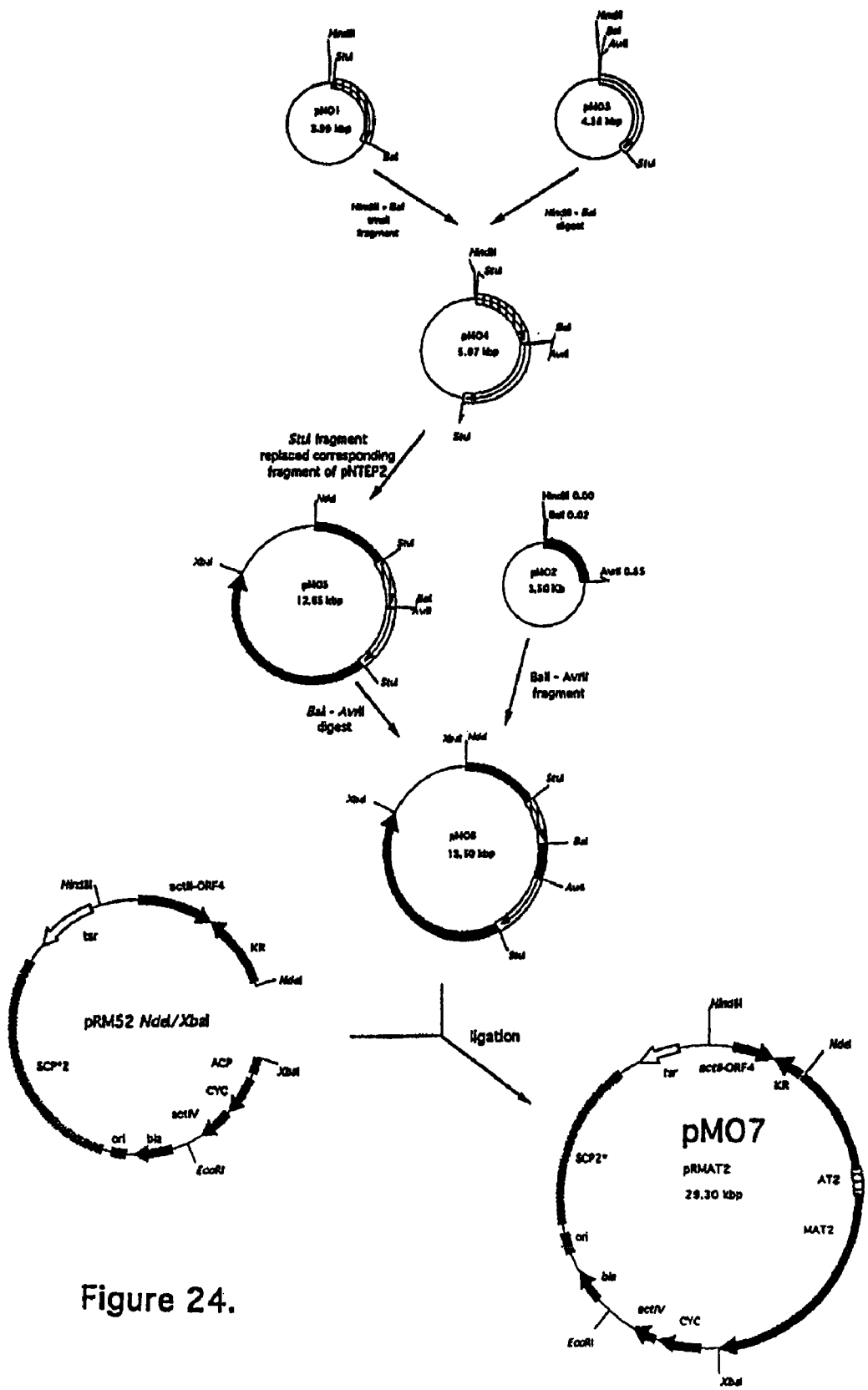
Figure 25:
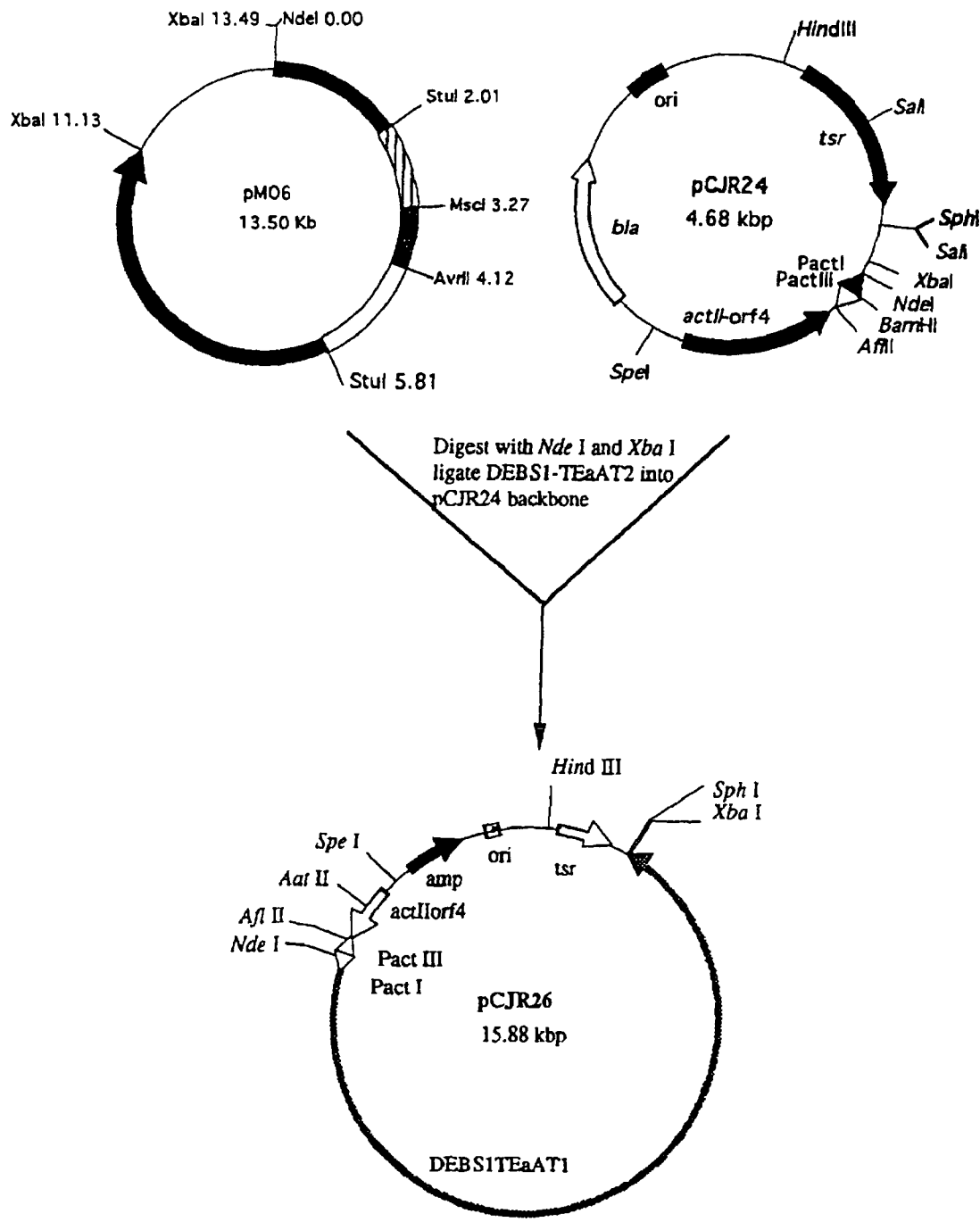
Figure 26:
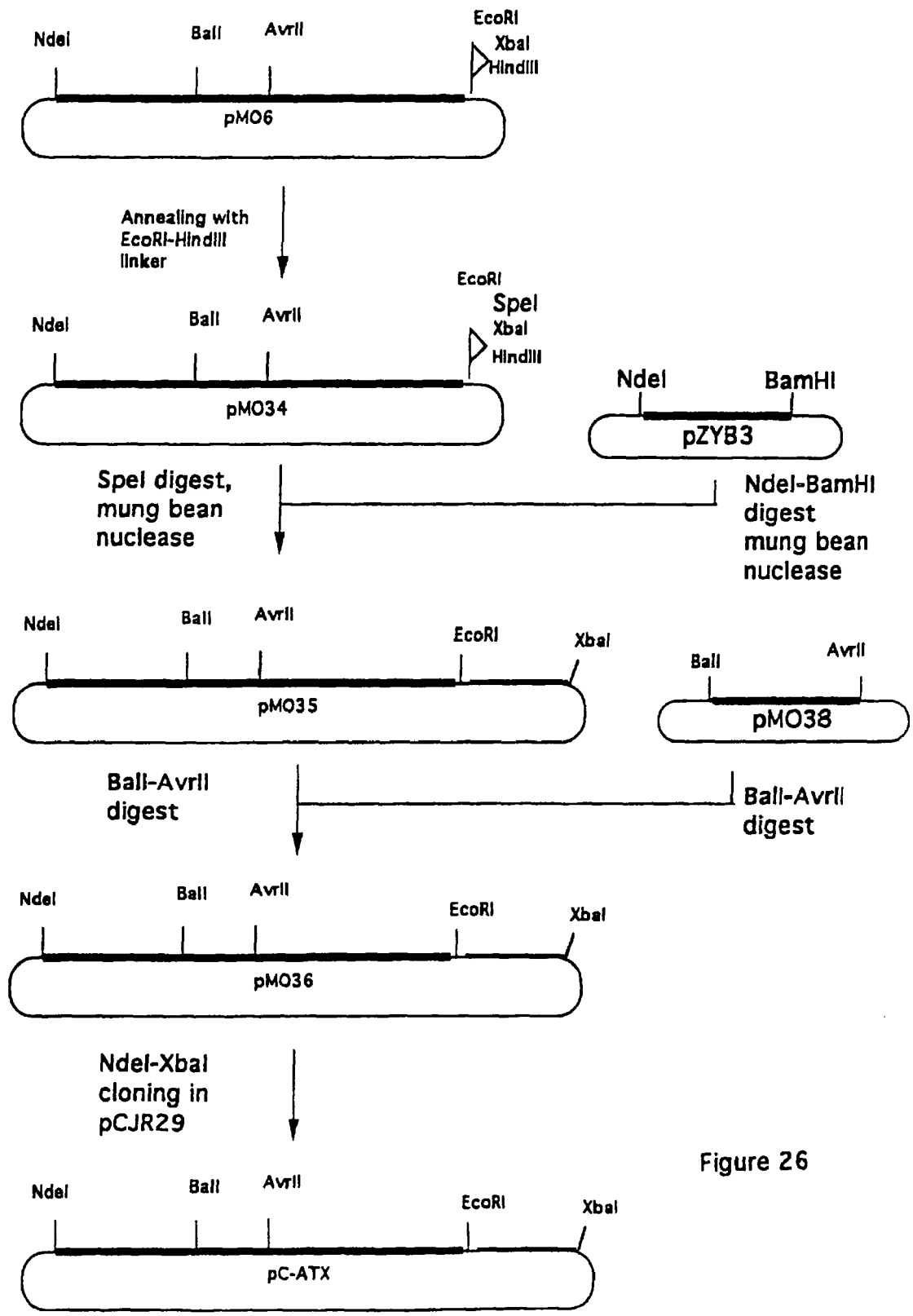
Figure 27:
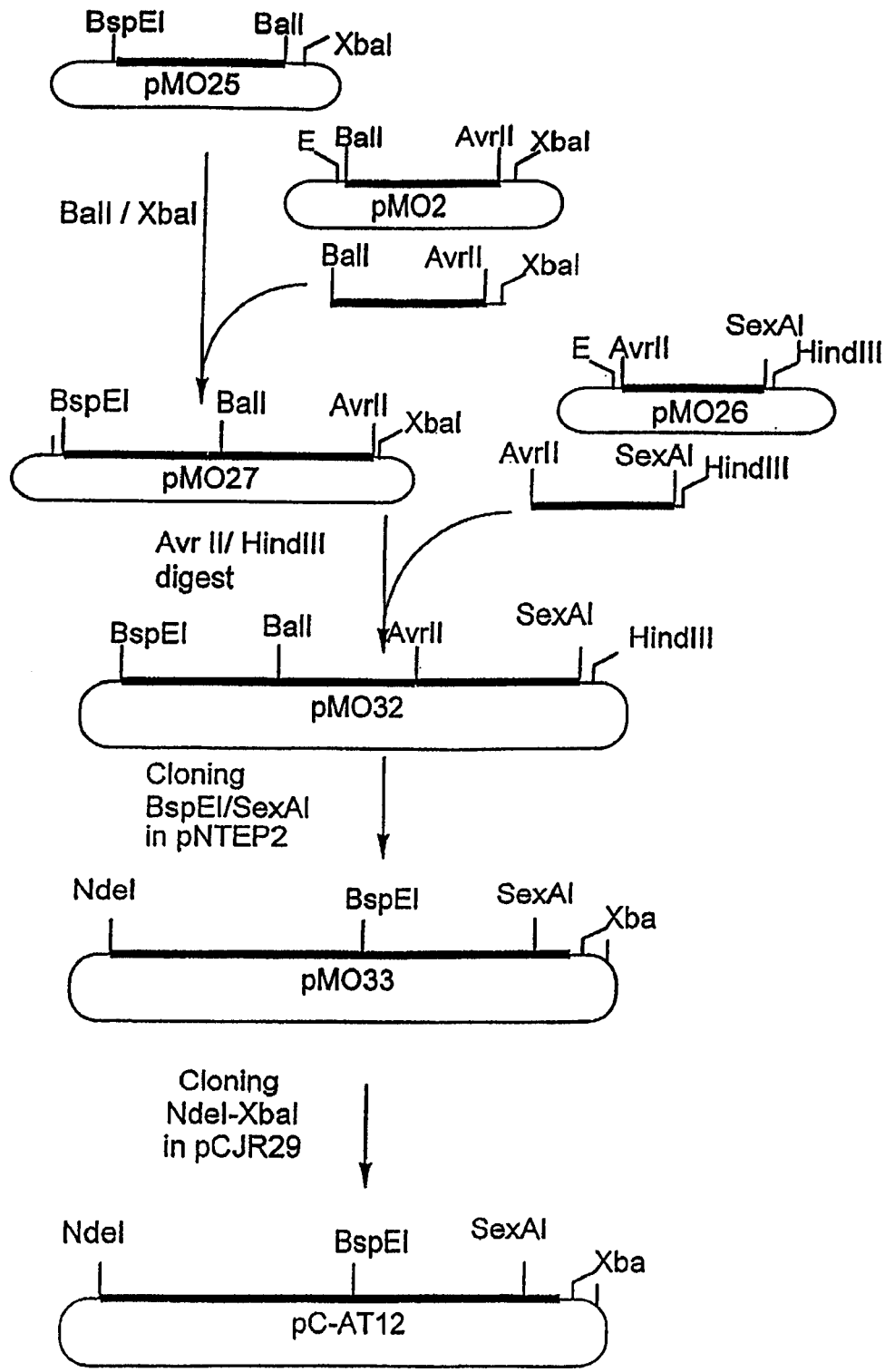
Figure 28:
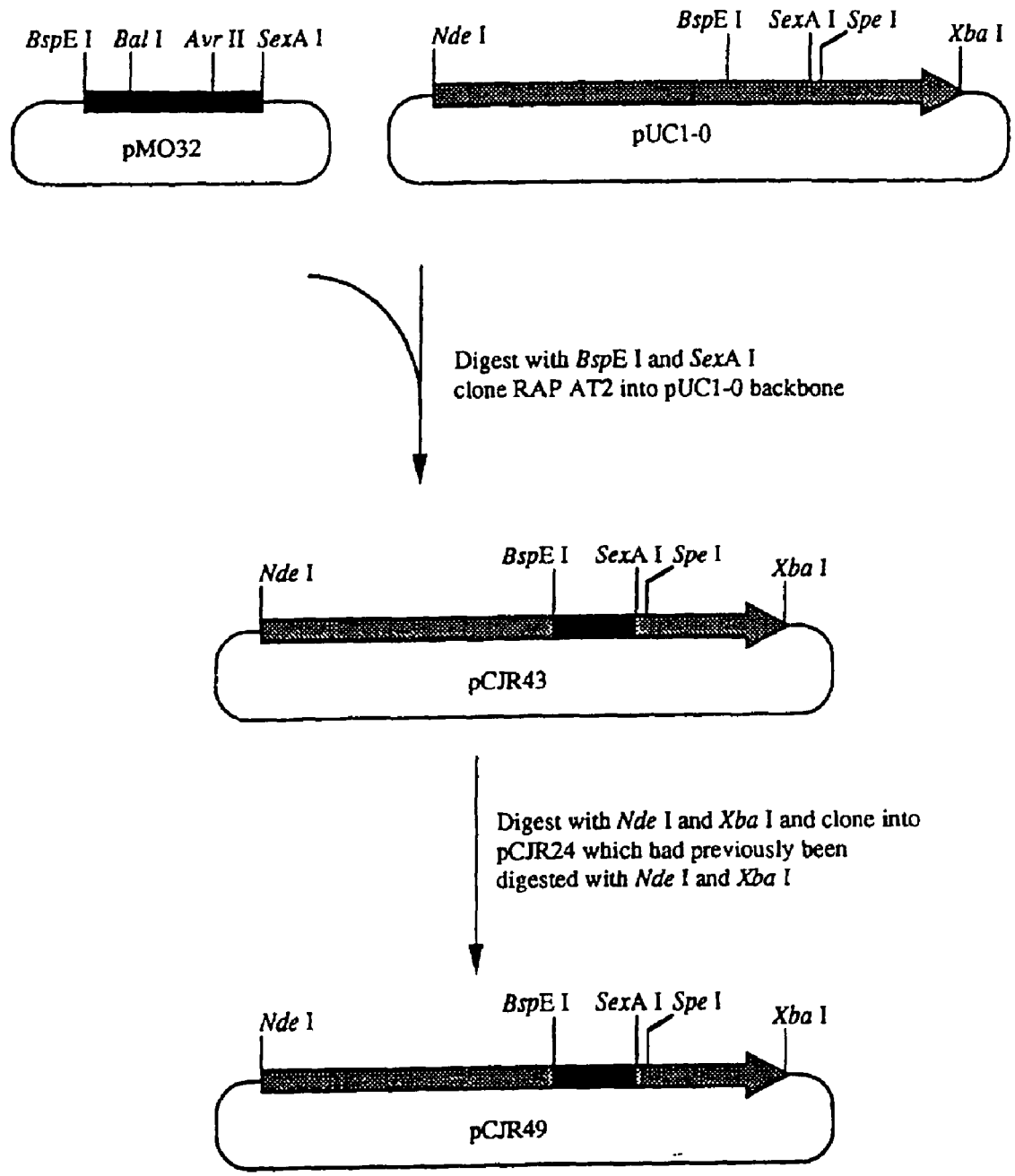
Figure 32:
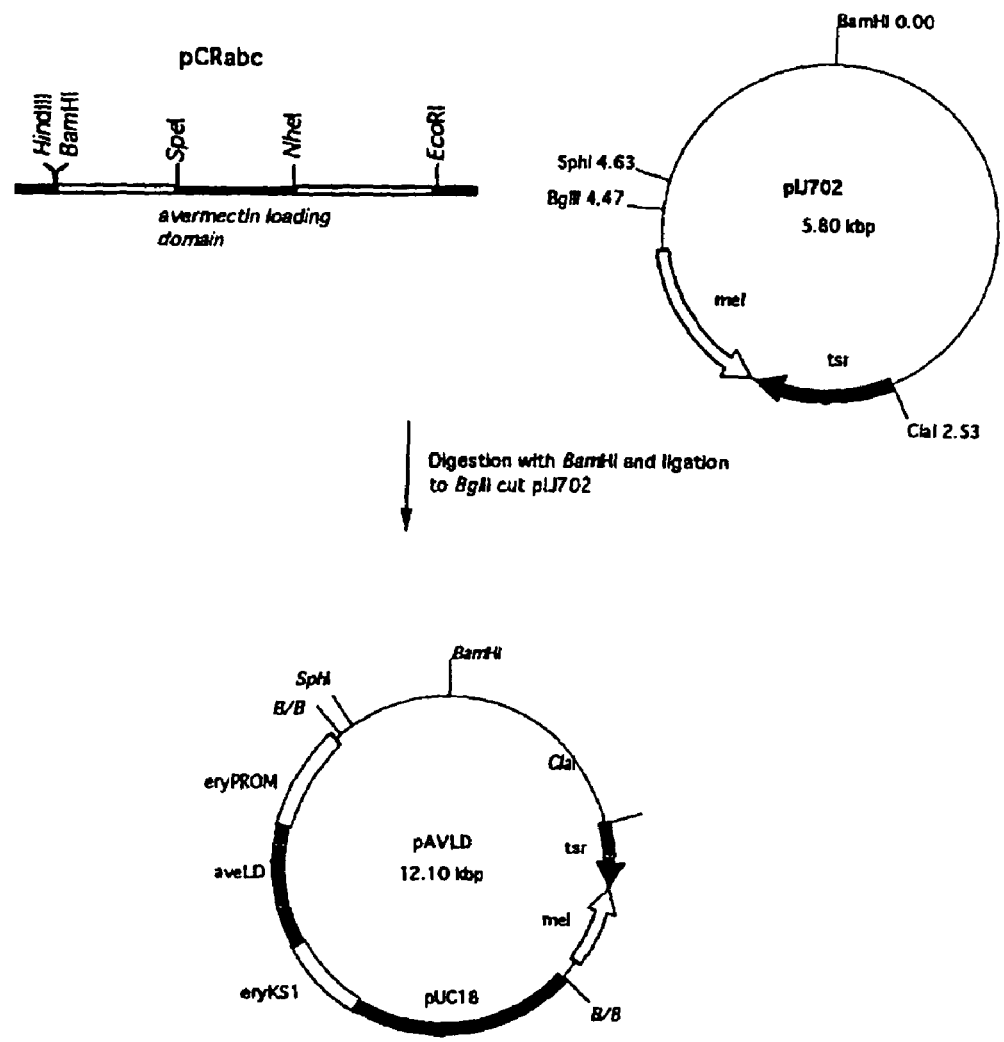
Figure 33:
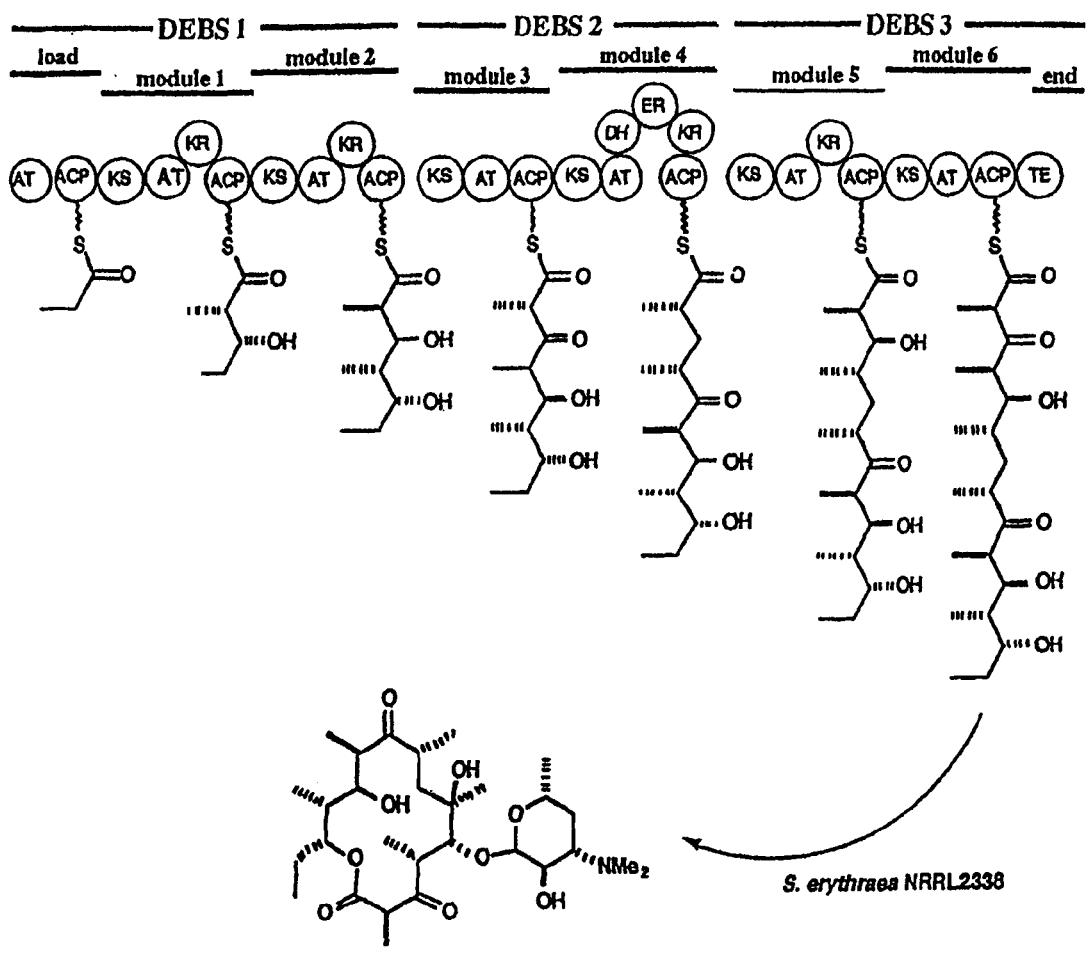

FIG. 10a (i), (ii) and b is a diagram showing the construction of plasmid pIG1;

FIG. 11 is a diagram showing the construction of plasmid pND20;

FIG. 12a and b is a diagram showing the construction of plasmid pKW15; this includes DNA encoding a loading molecule, a first extender module, and the chain-terminating thioesterase, capable of receiving modules;

FIG. 13 is a diagram showing the construction of plasmid pAR33;

FIG. 14a, b, c, and d is a diagram showing the construction of plasmid pAR8;

FIG. 15 is a diagram showing the construction of plasmid pE1A2TE;

FIG. 16 is a diagram showing the construction of plasmid pKS22;

FIG. 17a is a diagram showing the construction of plasmid pIB018;

FIG. 17b is a diagram showing the construction of plasmid pIB017;

FIG. 18 is a diagram showing the construction of plasmid pIB015 and plasmid pIB016;

FIG. 19 is a diagram showing the construction of plasmid pJLK15;

FIG. 20 is a diagram showing the construction of plasmid pJLK18;

FIG. 21 is a diagram showing the construction of plasmid pJLK21;

FIG. 22 is a diagram showing the construction of plasmid pKR1-0;

FIG. 23 is a diagram showing the construction of plasmid pKETO;

FIG. 24 is a diagram showing the construction of plasmid pMO7;

FIG. 25 is a diagram showing the construction of plasmid pCJR26;

FIG. 26 is a diagram showing the construction of plasmid pC-ATX;

FIG. 27 is a diagram showing the construction of plasmid pC-AT12;

FIG. 28 is a diagram showing the construction of plasmid pCJR49;

FIG. 29 is a diagram showing the construction of plasmid pCART11;

FIG. 30 is a diagram showing the construction of plasmid pARE24;

FIG. 31 is a diagram showing the construction of plasmid pARL3;

FIG. 32 is a diagram showing the construction of plasmid pAVLD;

FIG. 33 is a diagram showing the biosynthesis of a ketolide.

The present invention will now be illustrated, but is not intended to be limited, by means of some examples.

Use was made of the following media and solutions.

| Sucrose-Succinate defined medium | |
|---|---|
| sucrose | 69 g |
| $KNO_3$ | 10 g |
| succinic acid | 2.36 g |
| $KH_2PO_4$ | 2.7 g |
| $MgSO_4 \cdot 7H_2O$ | 1.2 g |
| $ZnCl_2$ | 10 mg |
| $MnCl_2 \cdot 4H_2O$ | 6.2 g |
| $CuCl_2 \cdot 2H_2O$ | 0.53 mg |
| $CoCl_2$ | 0.55 mg |
| $FeSO_4 \cdot 7H_2O$ | 2.5 mg |
| $CaCl_2 \cdot 2H_2O$ | 38 mg |
| milli-Q water | to 1 l |
| KOH | To pH 6-6.4 |
| YEME | |

| Tap water medium | |
|---|---|
| sucrose | 340 g |
| glucose | 5 g |
| yeast extract | 3 g |
| tryptone | 5 g |
| peptone | 5 g |
| yeast extract | 2.5 g |
| malt extract | 3 g |
| EDTA | 36 mg |
| glucose | 10 g |
| tap water | to 1.0 l |
| KOH | to pH 7.1 | after sterilisation: 2.5M $MgCl_2$ 2 ml
Trace elements solution: $ZnCl_2$, 40 mg/l; $FeCl_3 \cdot 6H_2O$, 200 mg/l; $CuCl_2 \cdot 2H_2O$, 10 mg/l; $MnCl_2 \cdot 4H_2O$, 10 mg/l; $Na_2B_4O_7 \cdot 10H_2O$), 10 mg/l; $(NH_4)_6MO_7O_{24} \cdot 4H_2O$, 10 mg/l;

| BW1 medium | |
|---|---|
| $CaCO_3$ | 2 g |
| Difco tryptone | 2.5 g |
| soy flour | 5 g |
| Difco yeast extract | 5 g |
| soluble starch (Sigma) | 20 g |
| pH 7.2 | |
| $K_2HPO_4$ | 1.2 g |
| $MgSO_4 \cdot 7H_2O$ | 1.2 g |
| $FeSO_4 \cdot 7HO_2O$ | 0.012 g |
| $MnSO_4$ | 0.0012 g |
| $ZnSO_4 \cdot 7H_2O$ | 0.0012 g |
| Tap water | to 1.0 l |

| BW2 Medium | |
|---|---|
| $CaCO_3$ | 7 g |
| soy flour | 5 g |
| Difco yeast extract | 5 g |

-continued

| soluble starch (Sigma) | 80 g |
| K$_2$HPO$_4$ | 1 g |
| MgSO$_4$·7H$_2$O | 1 g |

10 ml of a trace elements solution
Made up to 1 liter with distilled water. pH adjusted to 7.2.

EXAMPLE 1

Construction of strain Saccharopolyspora erythraea JC2

An S. erythraea host cell, genetically engineered to remove all of the native eryA genes which encode the erythromycin-producing type I PKS, except for the region of eryAIII DNA encoding the chain-terminating thioesterase, was constructed by homologous recombination starting from S. erythraea NRRL2338. S. erythraea NRRL2338 is a wild-type erythromycin-producing strain obtained from the Northern Regional Research Laboratories, Peoria, Ill., USA, under the above designation. The ery cluster is made up of the PKS genes, flanked by other genes involved in later stages of erythromycin biosynthesis, including those involved in glycosylation, hydroxylation and methylation.

Figure 2A:
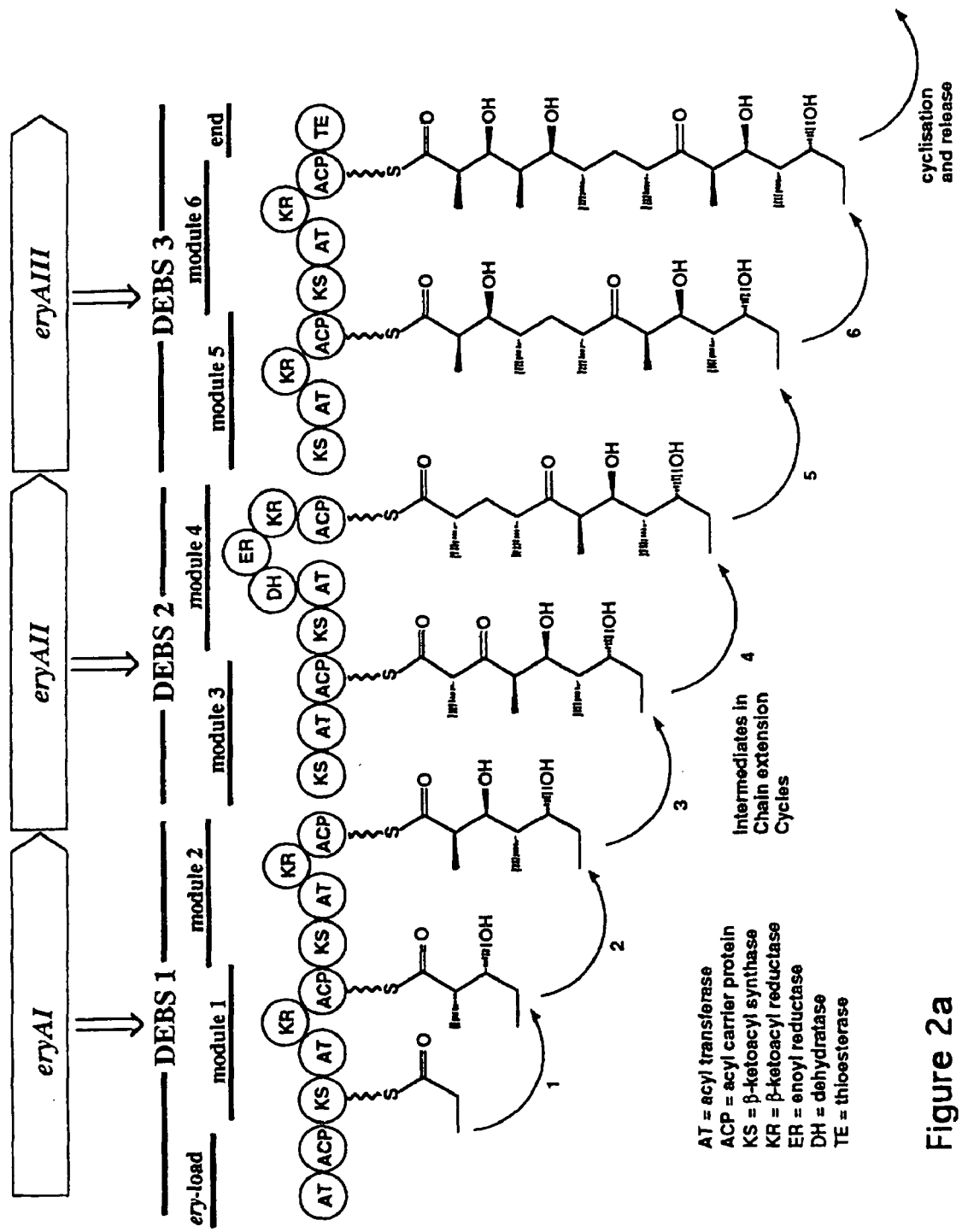
FIG. 2A is a diagram showing the functioning of 6-deoxyerythronolide synthase B (DEBS), a PKS producing 6-deoxyerythronolide B (6-DEB), a precursor of erythromycin A.
Figure 2B:
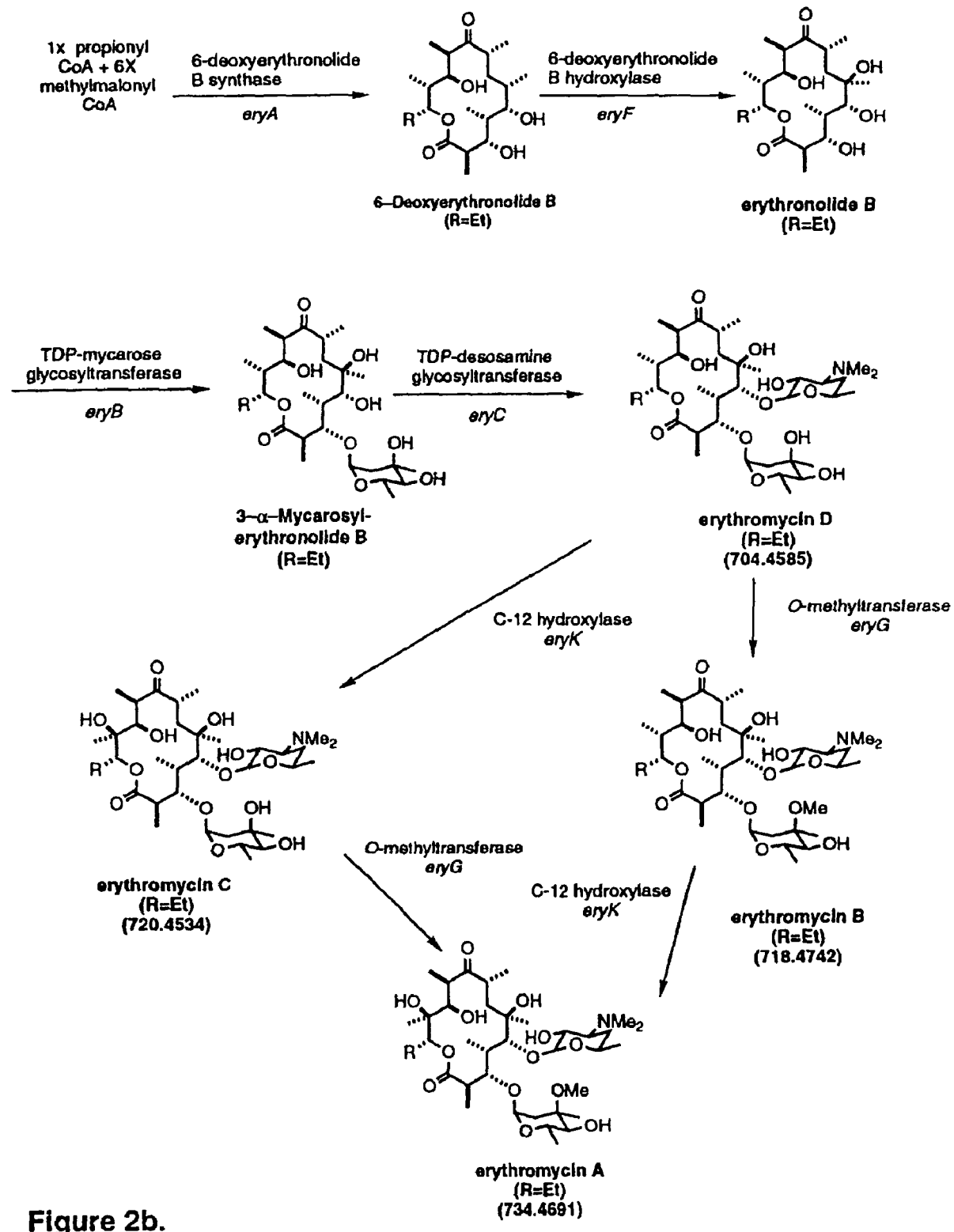
FIG. 2B shows post-PKS biosynthesis of erythromycins including the conversion of 6-DEB to erythromycin A.
Figure 3:
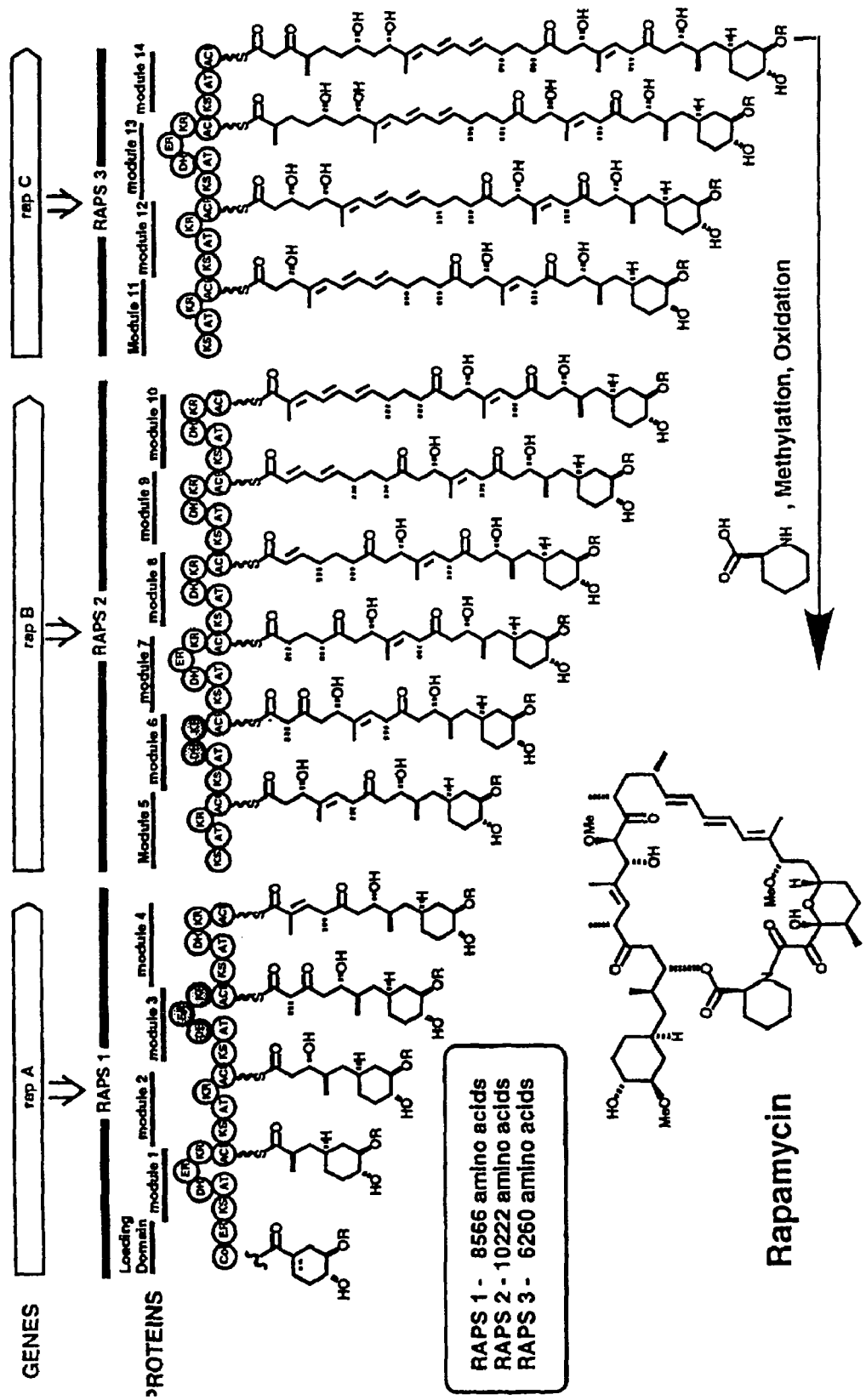
FIG. 3 is a diagram showing the biosynthesis of rapamycin.
Figure 4:
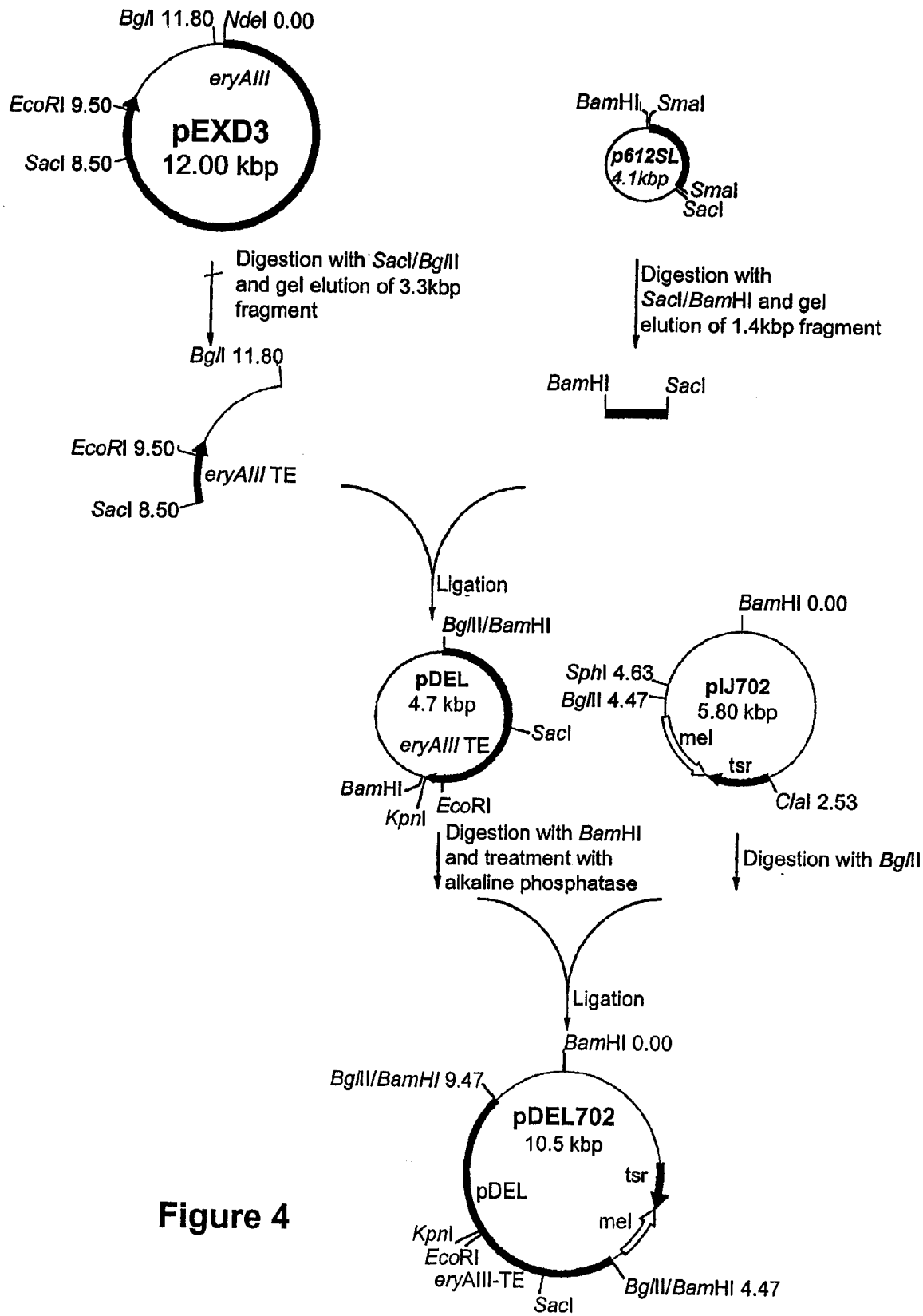
FIG. 4 is a diagram showing the construction of plasmid pDEL702.

Plasmid pDEL was constructed as follows (FIG. 4). The 1.4 kbp SmaI segment containing the start codon of eryAI was cloned into pUC18 to give p612SL, the segment was excised as a BamHI-SacI fragment using the multiple cloning sites of pUC18, and subcloned into a derivative of plasmid pT7-18 (Roberts, G. A. et al. Eur. J. Biochem. (1993) 214:305-311)) containing the SacI/KpnI fragment of eryAIII that encodes the C-terminus of DEBS3 from which a BglII-SacI fragment had been excised. The identity of plasmid pDEL was confirmed by restriction analysis.

Plasmid pDEL was digested with BamHI and treated with calf intestinal alkaline phosphatase, and ligated to plasmid pIJ702 (Katz, E. et al. J. Gen. Microbiol. (1983) 129:2703-2714) which had been linearised with BglII. The resulting mixture contains the desired plasmid pDEL702 (FIG. 4).

Protoplasts of S. erythraea NRRL2338 (Yamamoto, H. et al. J. Antibiot. (1986) 39:1304-1313) were transformed with 10 μg pDEL702 and stable thiostrepton resistant colonies were isolated. Individual colonies were selected and subcultured four times in non-selective liquid medium (tryptic soy broth) followed by preparation and regeneration of protoplasts. Thiostrepton sensitive colonies were isolated and characterised by restriction analysis and Southern hybridisation. One such colony was designated JC2. S. erythraea strain JC2 has been deposited at the National Collection of Industrial and Marine Bacteria, 23 St Machar Drive, Aberdeen, Scotland AB2 1RY, under the designation NCIMB 40802.

EXAMPLE 2

Construction of Strain Saccharopolyspora erythraea JC3

Figure 5:
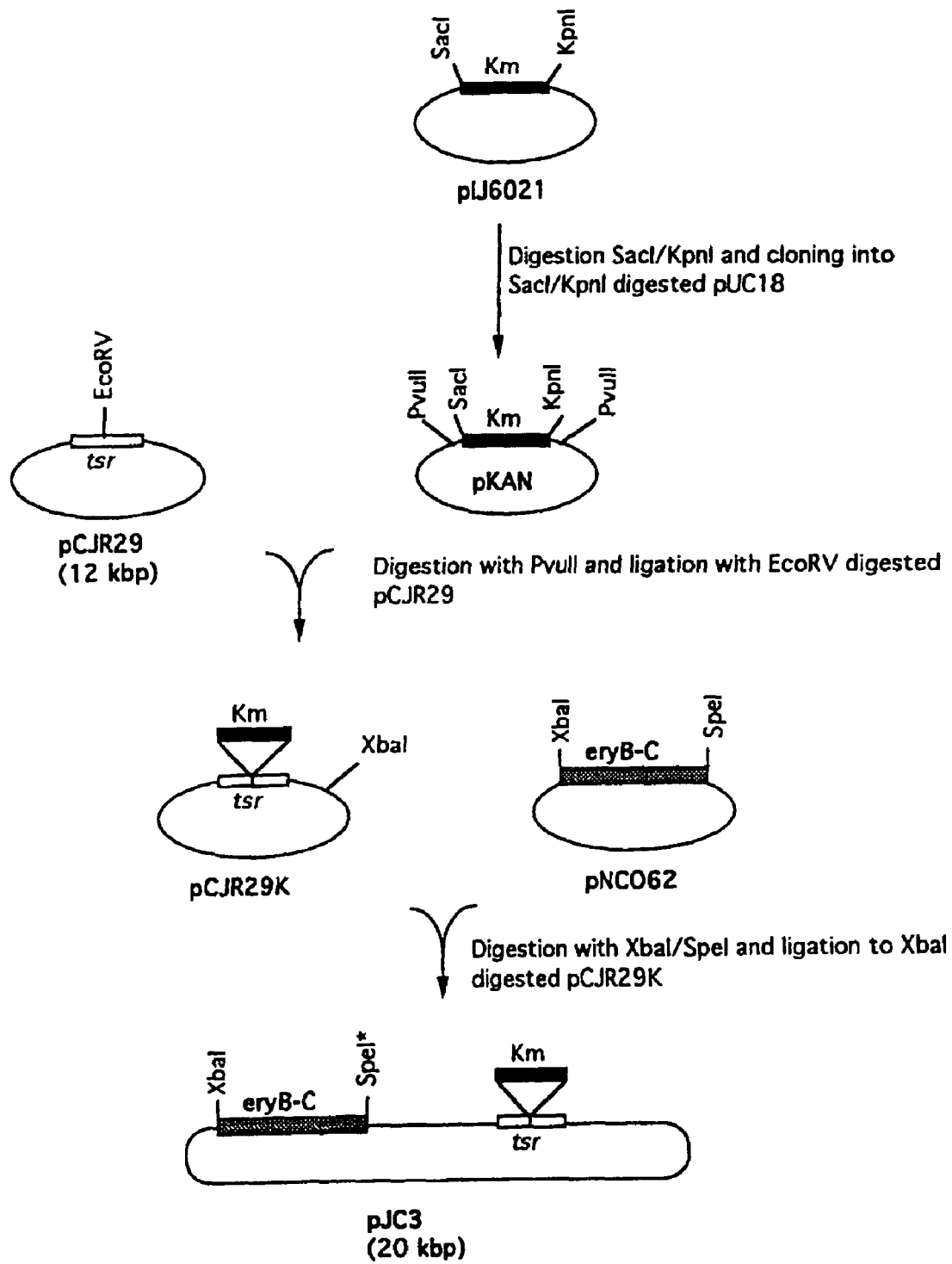
FIG. 5 is a diagram showing the construction of plasmid pJC3.

An S. erythraea host cell, genetically engineered which contains a derivative plasmid of pCJR29 integrated in the chromosome useful for the expression of homologous and heterologous genes was constructed by homologous recombination starting from S. erythraea JC2 (FIG. 5).

Plasmid pCJR29K was constructed as follows (FIG. 5), the 1.4 kbp SacI-SphI restriction fragment containing the kanamycin resistance gene from plasmid pIJ6021 (Takano, E. et al. Gene (1995) 166:133-137) was cloned into SacI-SphI digested pUC18 to produce pKAN, this plasmid was digested with PvuII and the 1.7 kbp fragment containing the kanamycin resistance gene was cloned into EcoRV digested pCJR29 to produce plasmid pCJR29K.

Plasmid pJC3 was constructed as follows (FIG. 5), the 6.2 kbp SpeI-XbaI restriction fragment from pNCO62 (Gaisser, S. et al. Mol. Gen. Genet. (1997) in press) was cloned into Xba I-digested pCJR29K to produce pJC3.

Protoplasts of S. erythraea JC2, prepared as described for S. erythraea NRRL2338, were transformed with 10 μg pJC3 and stable kanamycin (100 μg/ml) resistant colonies were isolated. Individual colonies were isolated and characterised by restriction analysis and Southern hybridisation. One such colony was designated S. erythraea JC3.

EXAMPLE 3

Construction of Strain S. erythraea JC103 (NRRL2338/pNHE)

To obtain an S. erythraea strain that overexpresses DEBS1, DEBS2 and DEBS3, the construction of intermediate plasmids was carried out as follows.

Construction of pARLD

The 1.6 kbp DNA segment encoding the loading domain of the erythromycin polyketide synthase from nucleotide 1 to 1680 was amplified by PCR employing the CloneAmp procedure (Raschtian, A. et al. Anal. Biochem. (1992) 91:91-97) with the following two oligonucleotides as primers:

(SEQ ID NO: 1)
5'-ACGCGUACUAGUCCGATTAATTAAGGAGGACCATCATGGCGGACCTG
TCAAAGCTC-3' and (SEQ ID NO: 2)
5'-AUGGAGAUCUCUCCGCTAGCGGTTCGCCGGGCGCCGCTTCGTTGGTC
CGCGCGCGGGTTTCCC-3' and using as template the DNA of plasmid pNTEP2. Approximately 30-60 ng of the PCR product (1.6 kbp) is digested with uracil DNA glycosylase for 30 minutes at 37° C. in the presence of 25 ng of pAMP18 vector DNA (Gibco BRL), the mixture is cooled on ice and used to transform E. coli TG1recO and individual colonies are checked for their plasmid content. The desired plasmid is identified by its restriction map and is designated pARLD.

Construction of pNHE

A 1.6 kbp fragment of plasmid pARLD is excised using PacI and NheI, purified by gel electrophoresis, and ligated to plasmid pCJR24 which had been cut with PacI and XbaI.

The ligation mixture is transformed into E. coli DH10B (Gibco BRL) and individual colonies, grown in the presence of ampicillin (100 μg/ml), are checked for their plasmid content. The desired plasmid is identified by its restriction map and is designated PNHE.

Construction of S. erythraea JC103 (NRRL2338/pNHE)

Approximately 5 μg pNHE, isolated from E. coli DH10B (pNHE) is used to transform S. erythraea NRRL2338 protoplasts and stable thiostrepton resistant colonies are selected. One of this colonies is selected and total DNA is prepared for Southern hybridisation analysis, to confirm that the plasmid has integrated specifically into the chromosomal copy of the eryAI gene in the area that encodes the N-terminal loading domain. This strain is designated S. erythraea JC103 (NRRL2338/pNHE).

EXAMPLE 4

Figure 6:
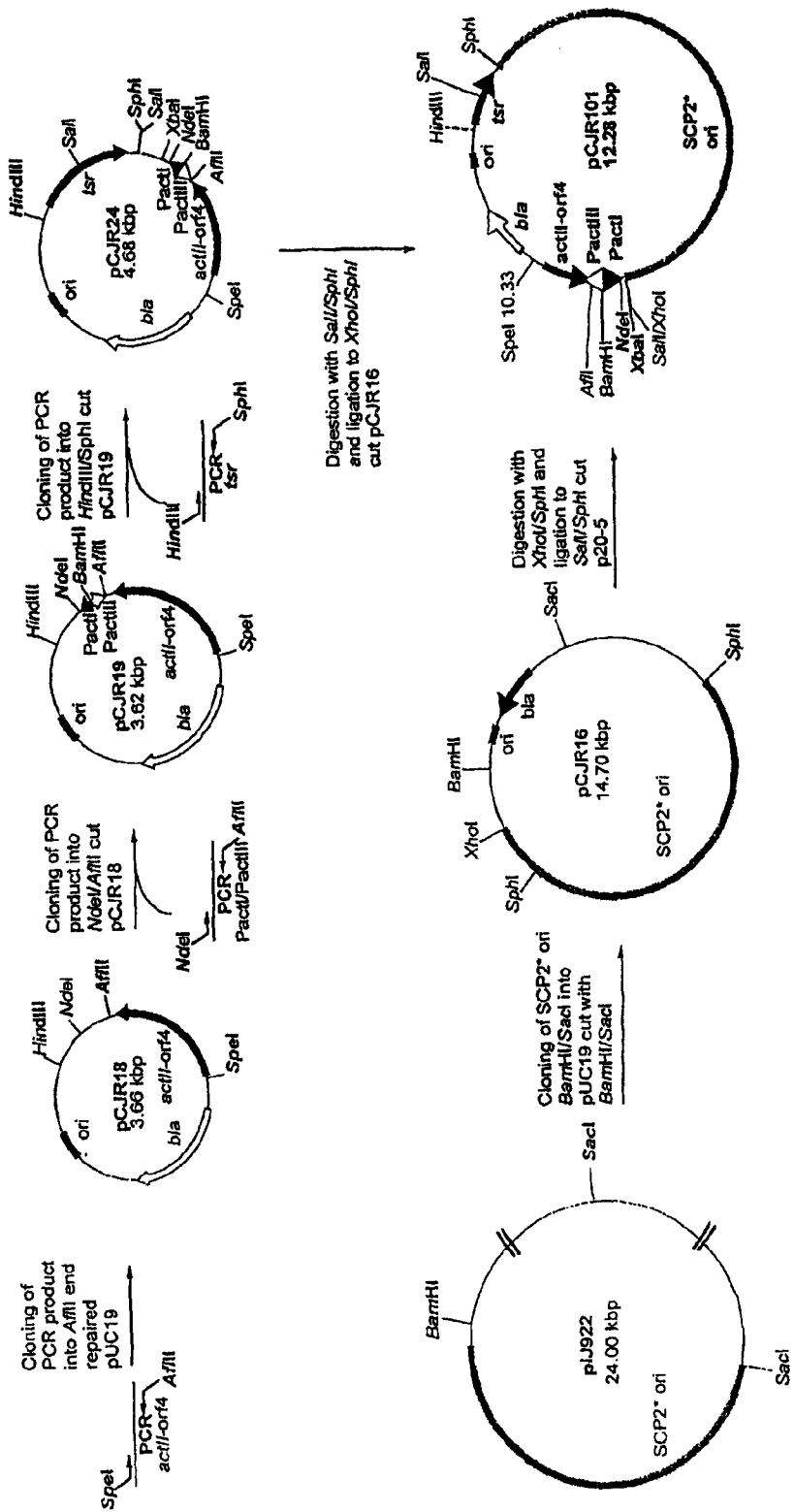
FIG. 6 is a diagram showing the construction of plasmid pCJR101; and of the precursor plasmid p20.5 which is now renamed plasmid pCJR24.

Construction of the Recombinant Vector pCJR101 pCJR101 (FIG. 6) is a shuttle plasmid constructed to be used for expression of PKS genes in actinomycetes. It includes a ColEI replicon to allow it to replicate in E. coli, an SCP2* low copy number Streptomyces replicon (Bibb, M. J. and Hopwood, D. A. J. Gen. Microbiol. (1981) 126:427) and the actII-orf4 activator gene from the act cluster which activates transcription from the act promoter during the transition from growth phase to stationary phase in the vegetative mycelium. It is constructed as follows: an approximately 970 by DNA fragment from pMF1015 (containing the actII-orf4 activator gene) (Fernandez-Moreno, M. A. et al. Cell (1991) 66:769-780) is amplified by PCR, using as primers the synthetic oligonucleotides: 5'-ACT AGT CCA CTG CCT CTC GGT AAA ATC CAG C-3' (SEQ ID NO: 3) and 5'-CTT AAG AGG GGC TCC ACC GCG TTC ACG GAC-3' (SEQ ID NO: 4), which also introduces flanking SpeI and AflII restriction sites. This fragment is introduced into the end-repaired AatII site of plasmid pUC19 to yield plasmid p18.14 (renamed pCJR18). An approximately 215 by DNA fragment is amplified from pMV400 which contains the bidirectional promoter pair PactIII/PactI) (Parro, V. et al. Nucl. Acids Res. (1991) 19:2623-2627), using as primers the synthetic oligonucleotides 5'-ACA TTC TCT ACG CCT AAG TGT TCC CCT CCC TGC CTC-3' (SEQ ID NO: 5) and 5'-GTG ATG TAT GCT CAT ATG TGT CCT CCT TAA TTA ATC GAT GCG TTC GTC CGG TG-3' (SEQ ID NO: 6), which also introduces flanking NdeI and AflII sites. The PCR product is digested with NdeI and AflII and ligated with the plasmid p18.14 (pCJR18) previously cut with NdeI and AflII, to generate plasmid p19.4 (renamed pCJR19). A 1.1 kbp HindIII-SphI fragment containing the tsr gene, which confers resistance to thiostrepton, is obtained by PCR from plasmid pIJ922 (Lydiate, D. J. et al. Gene (1985) 35:223-235) as template, using as primers the oligonucleotides 5'-TGA ACA CCA AGC TTG CCA GAG AGC GAC GAC TTC CCC-3' (SEQ ID NO: 7) and 5'-GAC AGA TTG CAT GCC CTT CGA GGA GTG CCC GCC CGG-3' (SEQ ID NO: 8) which also introduces flanking HindIII and SphI sites. The PCR product is digested with HindIII and SphI and ligated with plasmid p19.4 (pCJR19) cut with HindIII and SphI to obtain plasmid p20.5 (pCJR24). The plasmid pIJ922 is digested with BamHI and SstI and the fragment containing a portion of the fertility locus and the origin of replication (Lydiate, D. J. et al. Gene (1985) 35:223-235) is ligated into pUC19 digested with BamHI and Sst I to generate the bifunctional plasmid p16/2.2 (renamed pCJR16) (14.7 kbp). Plasmid p20.5 (pCJR24) is digested with SalI and SphI, the two larger fragments from the digest are purified by gel electrophoresis, and combined in a four-component ligation with plasmid 16/2.2 (pCJR16) which has been digested with XhoI and SphI. The ligation mixture is used to transform Streptomyces lividans and colonies are selected in the presence of thiostrepton. One such colony is shown to contain the desired plasmid pCJR101 (approx. 12.4 kbp), identified by its restriction pattern.

EXAMPLE 5

Construction of Plasmid pCJR29 (Renamed from pCJR110)

Figure 7:
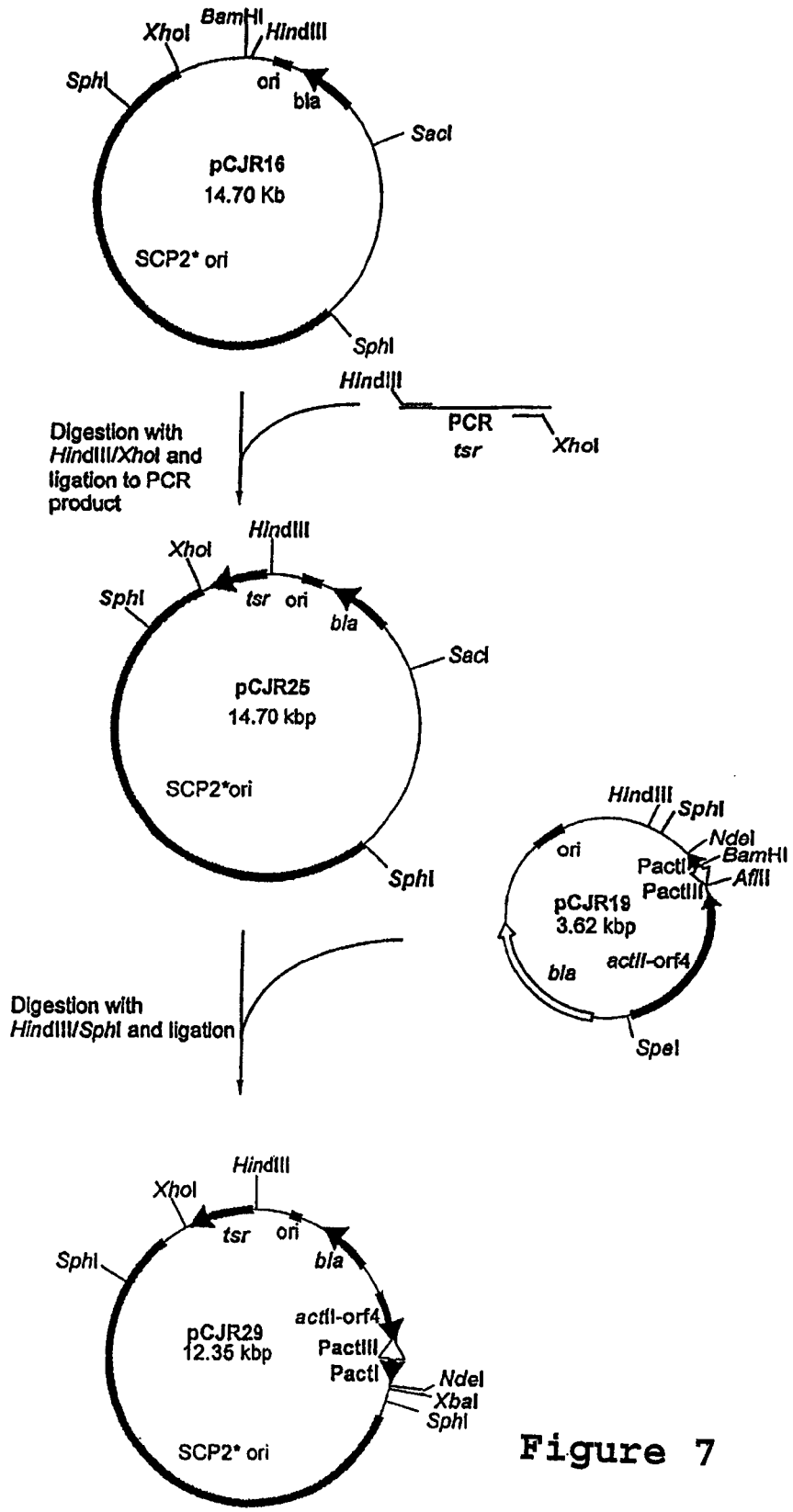
FIG. 7 is a diagram showing the construction of plasmid pCJR110 which is now renamed plasmid pCJR29.

The construction of plasmid pCJR29 (pCJR110) is illustrated in FIG. 7. A 1.1 kbp HindIII-XhoI fragment containing the tsr gene, which confers resistance to thiostrepton, is obtained by PCR from plasmid pIJ922 as template, using as primers the oligonucleotides 5'-TGA ACA CCA AGC TTG CCA GAG AGC GAC GAC TTC CCC-3' (SEQ ID NO: 7) and 5'-GAC AGA TTC TCG AGC CTT CGA GGA GTG CCC GCC CGG-3' (SEQ ID NO: 9) which also introduces flanking HindIII and XhoI sites. The PCR product is digested with HindIII and XhoI and ligated with plasmid 16/2.2 (pCJR16) which has been digested with HindIII and XhoI, to generate plasmid 22.1 (pCJR25). Plasmid p22.1 (pCJR25) is digested with HindIII and SphI and ligated with plasmid p19.4 (pCJR19) which has been digested with HindIII and SphI, to produce the desired plasmid pCJR29 (pCJR110) (approx. 12.4 kbp), identified by its restriction pattern. Plasmid pCJR29 (pCJR110) differs from pCJR101 in the orientation of the tsr gene, the actII-orf4 gene and the actI/actIII promoter, with respect to the SCP2*-derived origin of replication.

EXAMPLE 6

Construction of Plasmid pRM52

Plasmid pRM52 is a derivative of plasmid pRM5 (McDaniel, R. et al. Science, (1993) 262:1546-1550). pRM5 was first linearised by digestion with NdeI, end-repaired and then religated to produce pRM51. pRM51 was cut with PacI and NsiI and the large PacI-NsiI fragment was isolated and ligated to a short double-stranded oligonucleotide linker containing an NdeI site and constructed from the synthetic oligonucleotides 5'-TAAGGAGGACACATATGCA-3' (SEQ ID NO: 10) and 5'-TAATTCCTCCTGTGTAT-3' (SEQ ID NO: 11) which were annealed together. The ligation mixture was transformed into E. coli TG1recO and isolated colonies were screened for their plasmid content. The desired plasmid (19.6 kbp) was identified by its restriction map and was designated pRM52.

EXAMPLE 7

Construction of Plasmid pNTEP2

Figure 8:
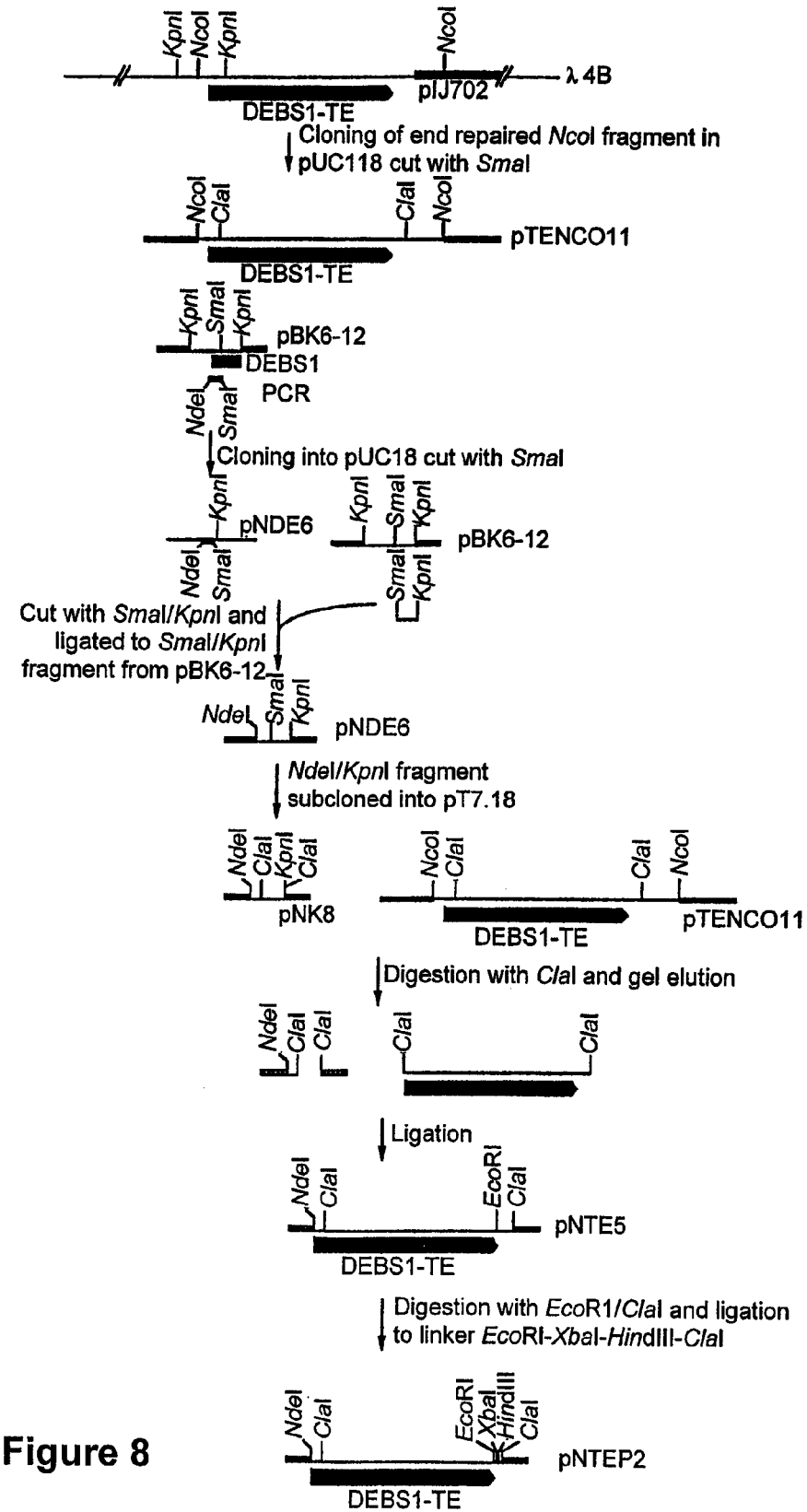
FIG. 8 is a diagram showing the construction of plasmid pNTEP2.

Plasmid pNTEP2 contains the entire open reading frame for the chimaeric DEBS1 plus thioesterase gene, with a unique NdeI site at the start codon and unique XbaI and HindIII sites immediately 3' of the stop codon. It is constructed via several intermediate plasmids as follows (FIG. 8):

Construction of Plasmid pTENCO11

A library of total DNA from S. erythraea TED8 (Cortes, J. et al. Science (1995) 268: 1487-1489) was constructed in the vector_DASH II (Stratagene) and probed with eryA gene fragments. One recombinant bacteriophage designated λ-4B had an insert extending from 700 bp upstream of the eryAI start codon to the thiostrepton resistance gene of the integrated plasmid in S. erythraea TED8. The λ-4b DNA was digested with NcoI and the 12 kbp NcoI fragment was end-repaired and ligated into SmaI-cut pUC18 and transformed into E. coli TG1recO. Individual colonies were screened for their plasmid content and one plasmid bearing the NcoI insert was selected and designated pTENCO11.

Construction of Plasmid pNK8

4.0 kb KpnI fragment extending from 1.4 kbp upstream of the correct eryAI start codon as previously determined (Caffrey, P. et al. FEBS Letters (1992) 304:225-228), to 2.6 kbp inside the eryAI gene of S. erythraea, was excised from plasmid pBK25 (Bevitt, D. J. et al. Eur. J. Biochem. (1992) 204:39-49) and cloned into pUC18 to obtain plasmid pBK6.12. DNA of this plasmid was used as the template for a PCR reaction to obtain a 360 by product in which a unique Nde I site is created at the start codon of eryAI and a unique SmaI site is created at the other end of the PCR product. The oligonucleotides used were 5'-CCC ATA TGG CGG ACC TGT CAA AGC-3' (SEQ ID NO: 12) and 5'-ATT GCG CGC CCT GGC CCG GGA A-3' (SEQ ID NO: 13). The product was end-repaired and ligated into SmaI cut pUC18, and transformed into E. coli TG1recO.

Individual colonies were screened for their plasmid content and one plasmid bearing the insert in an orientation such that the SmaI site was adjacent to the KpnI site of the polylinker was selected and designated plasmid pNDE6.

Plasmid pNDE6 was digested wth SmaI and KpnI, and ligated with a 2.3 kbp fragment of the eryAI gene obtained by digestion of plasmid pBK6.12 with SmaI and KpnI. The ligation mixture was used to transform *E. coli* TG1recO and individual colonies were screened for their plasmid content. A plasmid containing the desired 2.6 kbp NdeI-KpnI fragment was isolated and designated plasmid pNDE7. The NdeI-KpnI insert was excised from plasmid pNDE7 and ligated into plasmid pT7-18, previously digested with NdeI and KpnI. Plasmid pT7-18 is a derivative of plasmid pT7-7 (Tabor, S. and Richardson, C. C. Proc. Natl. Acad. Sci. USA (1985) 82:1074-1078) in which the polylinker is replaced by the polylinker from pUC18. The ligation mixture was used to transform *E. coli* TG1recO and individual colonies were screened for their plasmid content and one plasmid containing the desired 2.6 kbp NdeI-KpnI insert was selected and designated pNK8.

Construction of Plasmid pNTES

Plasmid pNK8 was transformed into a methylation-deficient strain of *E. coli* ET12567 (MacNeil, D. J. et al. Gene (1992) 111:61-68) and the plasmid pNKB was isolated from this strain and digested with ClaI. An 11 kbp ClaI fragment obtained by digestion of pTENC011 was ligated into the digested pNK8 and transformed into *E. coli* TG1recO. Individual colonies were screened for their plasmid content and one plasmid, in which the 11 kbp insert was correctly oriented to regenerate the reading frame of eryAI, was selected and designated pNTE5.

Construction of Plasmid pNTEP2

A ClaI-EcoRI polylinker, bearing unique restriction sites for XbaI and for HindIII was constructed, from the following complementary synthetic oligonucleotides:

```
5'-AATTCATAGTCTAGAAGCTTAT-3' (SEQ ID NO: 14)
and
5'-CGATAAGCTTCTAGACTATG-3' (SEQ ID NO: 15).
```

The polylinker was ligated into plasmid pNTE5, which had been digested with ClaI and EcoRI to remove a 2.3 kbp ClaI-EcoRI fragment. The ligation mixture was used to transform *E. coli* TG1recO and individual colonies were screened for their plasmid content. One plasmid containing the polylinker was identified and designated pNTEP2.

EXAMPLE 8

Construction of Plasmid pRMTE

Figure 9:
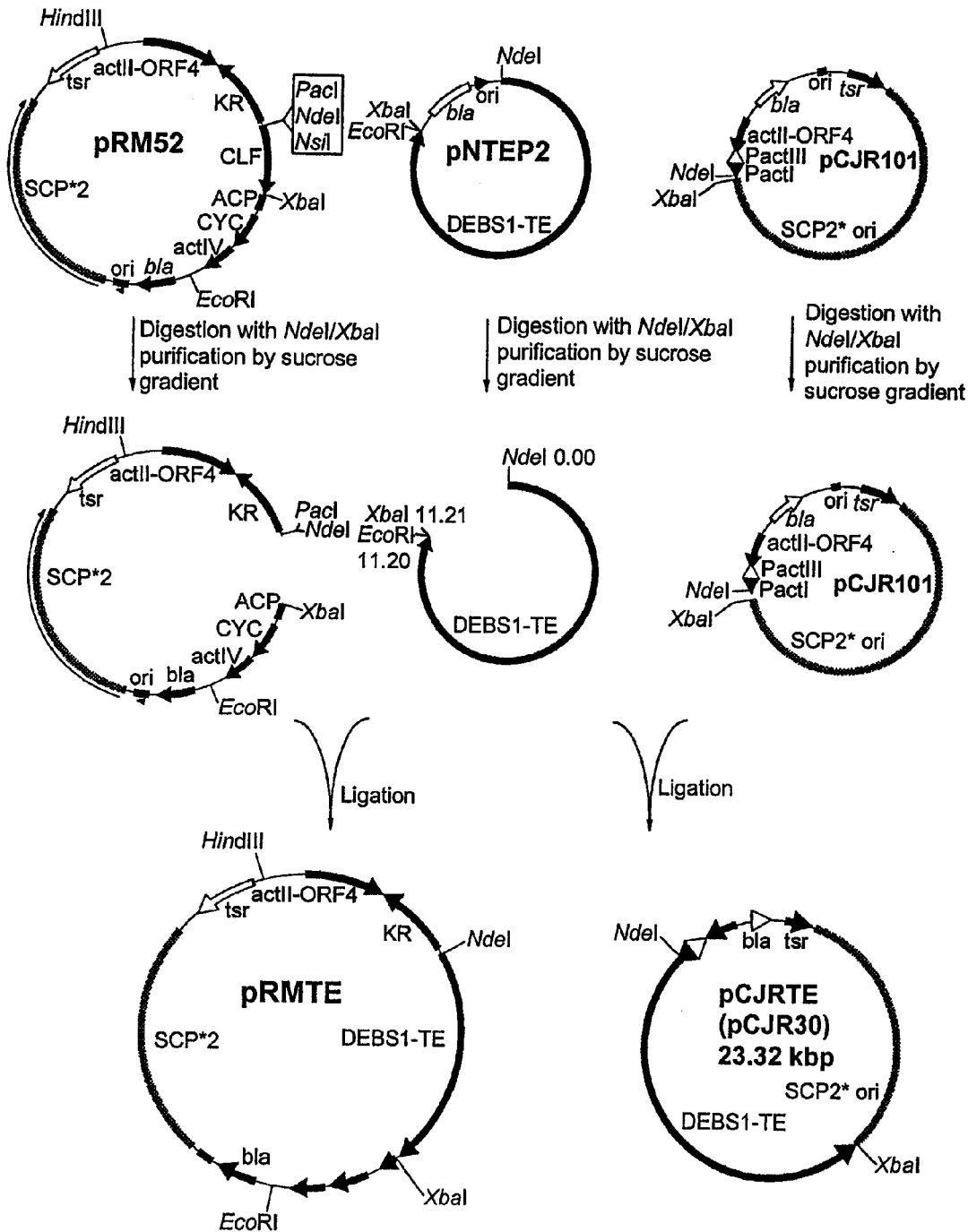
FIG. 9 is a diagram showing the construction of plasmid pRMTE and pCJRTE; the latter plasmid is now renamed pCJR30.

Plasmid pNTEP2 (14 kbp) was digested with NdeI and XbaI and the insert was purified by sedimentation on a sucrose gradient. The purified insert was ligated into plasmid pRM52 (19.6 kbp) (Example 4) which had been digested with NdeI and XbaI, and the vector purified by sedimentation on a sucrose gradient. The ligation mixture was used to transform *E. coli* and individual colonies were checked for their plasmid content. The desired plasmid pRMTE (31.5 kbp) was identified by its restriction pattern (FIG. 9).

EXAMPLE 9

Construction of Plasmid pCJRTE (Also Named pCJR30)

Plasmid pNTEP2 (Example 5) is digested with NdeI and XbaI and the insert is purified by sedimentation on a sucrose gradient. The purified insert is ligated into plasmid pCJR101 (12.4 kbp) which has been digested with NdeI and XbaI, and purified by sedimentation on a sucrose gradient. The ligation mixture is used to transform E. coli DHB10 and individual colonies are screened for their plasmid content. The desired plasmid PCJRTE (pCJR30) (24.3 kbp) is identified by its restriction pattern (FIG. 9).

EXAMPLE 10

Construction of *S. avermitilis* ATCC 31272/pCJRTE (pCJR30) and production of triketide lactone ("TKL") derivatives therewith.

(i) Construction

Approximately 5 µg of plasmid pCJRTE (pCJR30) is transformed into protoplasts of *S. avermitilis* ATCC 31272 and stable thiostrepton resistant colonies are isolated. Several such colonies are analysed for their content of plasmid DNA. A colony containing a plasmid whose restriction map shows it to be identical to pCJRTE (pCJR30), is designated *S. avermitilis* ATCC 31272/pCJRTE (pCJR30).

(ii) Production of (Ac)-TKL and TKL

*S. avermitilis* ATCC 31272/pCJRTE (pCJR30) is inoculated into medium BW1 containing 50 µg/ml thiostrepton, and allowed to grow for four days at 28-30% C. After this time, 15 ml of the cell suspension is used to inoculate 150 ml of liquid medium BW2 containing 50_g/l thiostrepton, and allowed to grow for 6 days. After this time the cells are removed by centrifugation, washed with water, and the supernatants are combined and extracted three times with ethyl acetate (250 ml). The combined ethyl acetate extracts are washed with an equal volume of saturated sodium chloride, dried over anhydrous sodium sulphate and the ethyl acetate is removed by evaporation under reduced pressure. Samples of the residue are taken up in a minimal quantity of diethyl ether, filtered through a plug of silica, and analyzed by GC, which reveals the presence of both (Ac)-TKL and TKL (Formula II: $R_1=R_2=Me$; $R_3=Me$ for (Ac)-TKL, and Et for TKL), with identical retention times to authentic synthetic samples.

EXAMPLE 11

Construction of Plasmids pIG1 and pIG101

Figure 10B:
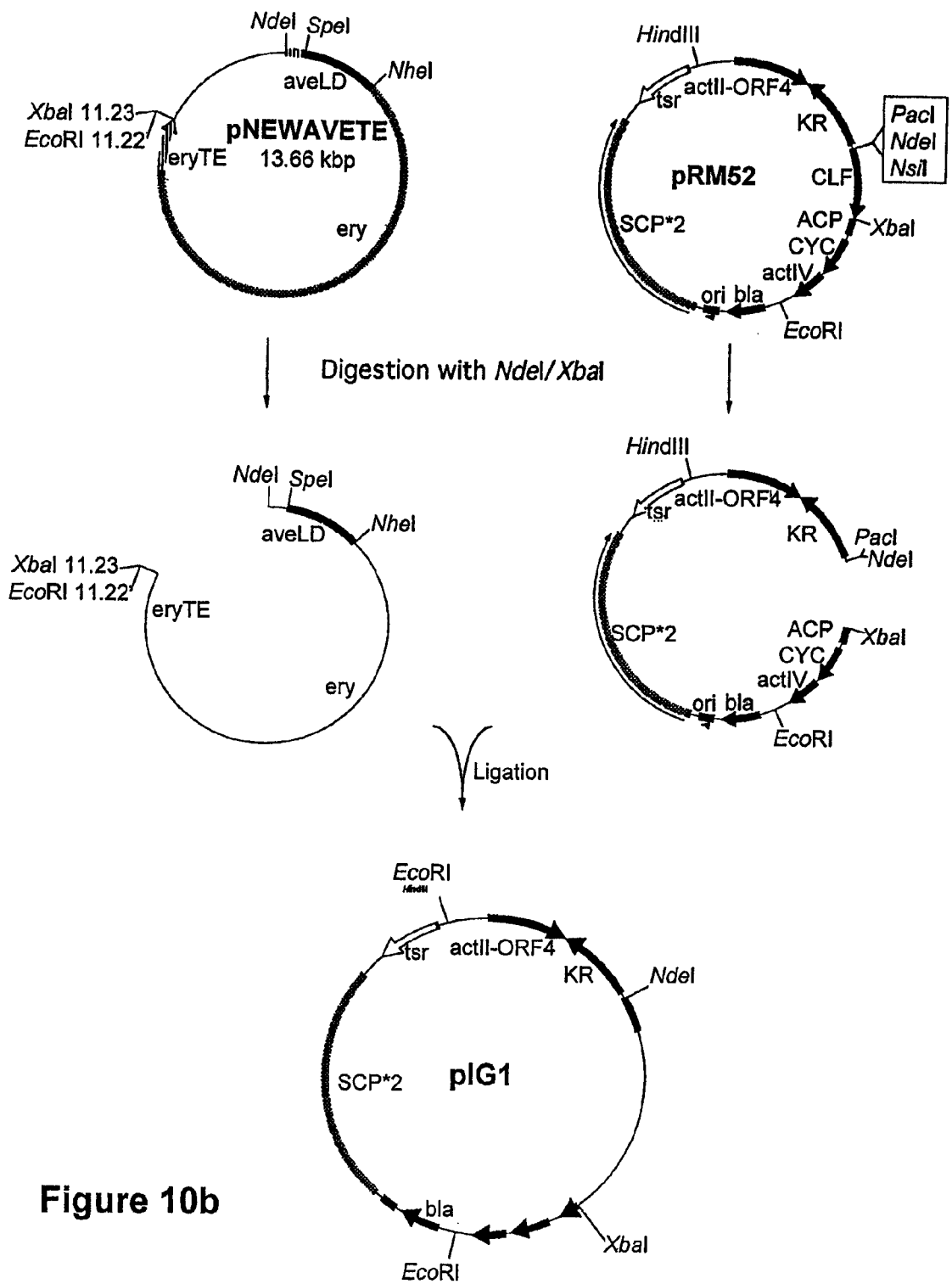

Plasmids pIG1 and pIG101 each consist of an SCP2*-derived plasmid containing a hybrid Type I PKS gene comprising the avr loading module in place of the ery loading module, the first two extension modules of the ery PKS and the thioesterase of the ery PKS. These are constructed via several intermediate plasmids as follows (FIG. 10).

Construction of Plasmid pVE 3.4

Plasmid pVE1446 which contains a portion of the avermectin (avr) PKS genes was obtained from *E. coli* strain ATCC 68250 (MacNeil, D. J. et al. Ann. N. Y. Acad. Sci. (1994) 721:123-132). Plasmid pVE1446 was digested with BamHI and the 7.6 kbp fragment between coordinates 32.15 and 3.40 (MacNeil, D. J. et al. Ann. N. Y. Acad. Sci. (1994) 721:123-132) was purified by gel electrophoresis and recircularised. The mixture contained the desired plasmid pVE3.4 which was isolated after transformation of *E. coli* strain TG1recO.

Construction of Plasmid pNCO12

Plasmid pBK25 (Bevitt, D. J. et al. Eur. J. Biochem. (1992) 204:39-49) was digested with NcoI and the 12 kbp fragment was end-repaired and ligated into plasmid pUC18 which had been linearised with SmaI. The ligation mixture was transformed into *E. coli* TG1 recO and individual colonies were checked for their plasmid content. The desired plasmid pNCO12 was identified by its restriction pattern.

Construction of Plasmid pCRabc

Plasmid pCRabc (FIG. 10) was constructed as follows. Three separate PCR reactions were conducted: First, 20 pmol each of synthetic oligonucleotides A1 (5'-CTC GTC GGT GGC TTT GCG-3'; SEQ ID NO: 16) and A2 (5'-CCC GGG AAA AAC GAA GAC TAG TGG CGC GGA CGG CCG-3'; SEQ ID NO: 17) were used to amplify a 1.0 kbp product from 100 ng pNCO12 template. The PCR product was end-repaired, phosphorylated and cloned into SmaI-cut pUC18 to obtain plasmid pCRa. Secondly, 20 pmol each of synthetic oligonucleotides C1 (5'-CAC GCG CAG CGC GGC GGA-3'; SEQ ID NO: 18) and C2 (5'-CGAA CCG CTA GCG GTC GTC GCG ATG GCC T-3'; SEQ ID NO: 19) were used to amplify a 1.5 kbp product from 100 ng pNCO12 template. The product was end-repaired, phosphorylated and cloned into SmaI-cut pUC18 to obtain plasmid pCRc. Thirdly, 20 pmol each of synthetic oligonucleotides B1 (5'-GTGGC-CCGGCCGTCCGCGCCACTAGTCTTCGTTTTT-3'; SEQ ID NO: 20) and B2 (5'-AACAGCTAGCGGTTCGTCCGC-CGCTGCCGTGCC-3'; SEQ ID NO: 21) were used to amplify a 1.4 kbp product from 100 ng pVE3.4 template. The product was end-repaired, phosphorylated and cloned into SmaI-cut pUC18 to obtain plasmid pCRb.

Plasmid pCRa was digested with HindIII and SpeI and the 1.0 kbp insert was ligated with plasmid pCRb previously digested with HindIII and SpeI, to obtain plasmid pCRab. Plasmid pCRc was digested with NheI and EcoRI and the 1.5 kbp insert was ligated with plasmid pCRab previously digested with NheI and EcoRI to obtain plasmid pCRabc.

Construction of Plasmid pNEWAVETE

Plasmid pCRabc was digested with MfeI and SfiI and the DNA fragment containing the loading domain of the avr PKS was purified by gel electrophoresis and ligated with plasmid pNTEP2 which had been digested with MfeI and SfiI and the larger fragment purified by gel electrophoresis. The ligation mixture was transformed into *E. coli* TG1 recO and individual colonies were checked for their plasmid content. The desired plasmid pNEWAVETE (13.7 kbp) was identified by its restriction pattern.

Construction of Plasmid pIG1

Plasmid pNEWAVETE was digested with NdeI and XbaI and the insert was purified by sedimentation on a sucrose gradient. The purified insert was ligated into plasmid pRM52 (19.6 kbp) which had been digested with NdeI and XbaI, and the vector purified by sedimentation on a sucrose gradient. The ligation mixture was used to transform *E. coli* and individual colonies were checked for their plasmid content. The desired plasmid pIG1 was identified by its restriction pattern.

Construction of Plasmid pIG101

Plasmid pNEWAVETE is digested with NdeI and XbaI and the insert is purified by sedimentation on a sucrose gradient. The purified insert is ligated into plasmid pCJR101 (Example 4) which has been digested with NdeI and XbaI, and purified by gel electrophoresis. The ligation mixture is used to transform *E. coli* DHB10 and individual colonies are screened for their plasmid content. The desired plasmid pIG101 is identified by its restriction pattern.

EXAMPLE 12

Construction of *S. coelicolor* CH999/pIG1 and Production of TKL Derivatives.

(i) Construction

Plasmid pIG1 which had been isolated from *E. coli* ET12567 (MacNeil. D. J. et al. Gene (1992) 111:61-68) was used to transform protoplasts of *S. coelicolor* CH999 and stable thiostrepton resistant colonies were isolated.

Individual colonies were checked for their plasmid content and the presence of plasmid pIG1 was confirmed by its restriction pattern.

(ii) Production of TKL, (Ac)TKL, (i-but)TKL and (s-pent) TKL using *S. coelicolor* CH999/pIG1

*S. coelicolor* CH999/pIG1 was inoculated into 100 ml YEME medium containing 50 µg/ml thiostrepton and allowed to grow for five days at 28-30° C. After this time the broth was filtered to remove mycelia. The broth was extracted three times with quarter volumes of ethyl acetate and the combined ethyl acetate extracts were dried over anhydrous sodium sulphate, and the ethyl acetate was removed under reduced pressure. The residue was taken up in ethyl acetate and filtered through a plug of silica, the ethyl acetate was again removed and the residue was taken up in diethyl ether and subjected to flash chromatography on a column of silica gel eluted with diethyl ether. A fraction containing (s-pent)-TKL and (i-but)-TKL was separated from a fraction containing TKL, with minor amounts of (Ac)-TKL in a third fraction. The compounds were identified by their co-migration with authentic standards on GC analysis (25 m column, programmed for 2 minutes at 70° C., then ramped to 250° C. over 24 minutes. The retention times for (s-pent)-TKL, (i-but)-TKL, TKL and (Ac)-TKL were 14.9, 13.6, 12.9 and 11.9 minutes respectively. GC, electrospray MS and 1H-NMR were used to show that the major component (50-60%) was TKL.

EXAMPLE 13

Construction of *S. coelicolor* CH999/pIG101 and Production of TKL Derivatives (i) Construction Plasmid pIG101 which has been isolated from *E. coli* ET12567 (MacNeil, D. J. et al. Gene (1992) 111:61-68) is used to transform protoplasts of *S. coelicolor* CH999 and stable thiostrepton resistant colonies were isolated. Individual colonies are checked for their plasmid content and the presence of plasmid pIG101 is confirmed by its restriction pattern.

(ii) Production of TKL, (Ac)TKL, (i-but)TKL and (s-pent) TKL Using *S. coelicolor* CH999/pIG101

*S. coelicolor* CH999/pIG101 is inoculated into YEME medium containing 50 µg/ml thiostrepton and allowed to grow for five days at 28-30° C. The broth is extracted three times with quarter volumes of ethyl acetate and the combined ethyl acetate extracts are dried over anhydrous sodium sulphate, and the ethyl acetate is removed under reduced pressure. The residue was treated as in Example 12 and gave similar results.

EXAMPLE 14

Construction of *S. avermitilis* ATCC31272/pIG1 and Production of TKL Derivative (i) Construction Plasmid pIG1 which had been isolated from *E. coli* ET12567 (MacNeil, D. J. et al. Gene (1992) 111:61-68) was transformed into protoplasts of *S. avermitilis* ATCC31272 and stable thiostrepton resistant colonies were isolated.

Individual colonies were checked for their plasmid content and the presence of plasmid pIG1 was confirmed by its restriction pattern.

(ii) Production of TKL, (Ac)TKL, (i-but)TKL and (s-pent) TKL Using *S. avermitilis* ATCC31272/pIG1

*S. avermitilis* ATCC31272/pIG1 was first inoculated into medium BW1 containing 50 µg/ml thiostrepton, and allowed to grow for four days at 28-30°C. After this time 20 ml of the broth is used to seed 150 ml of medium BW2 containing 50 µg/ml of thiostrepton.

The inoculated organism was then allowed to grow for 10-12 days. The broth was filtered to remove mycelia, and extracted three times with quarter volumes of ethyl acetate and the combined ethyl acetate extracts were dried over anhydrous sodium sulphate, and the ethyl acetate was removed under reduced pressure, to give about 10 mg crude product per litre. The residue was dissolved in ethyl acetate, passed through a plug of silica, and the solvent was removed. The residue was dissolved in diethyl ether and subjected to flash chromatography on a silica column (1 cm×15 cm) eluted with diethyl ether, and fractions of 10 ml each were collected and assayed by GC. The diethyl ether was evaporated to leave about 10 mg of oily residue containing triketide lactones. The major component (50-60%) was (s-pent)-TKL, with (i-but)-TKL, TKL and (Ac)-TKL also present (i.e. compounds of formula II with $R_1=R_2=Me$, and $R_3=$1-methylpropyl ((s-pent)-TKL), i-Pr((i-But)-TKL), Et(TKL) and Me((Ac)-TKL).

EXAMPLE 15

Construction of S. avermitilis ATCC31272/pIG101 and Production of TKL Derivatives
(i) Construction
Plasmid pIG101 which has been isolated from E. coli ET12567 (MacNeil, D. J. et al. Gene (1992) 111:61-68) is transformed into protoplasts of S. avermitilis ATCC31272 and stable thiostrepton resistant colonies are isolated.
Individual colonies are checked for their plasmid content and the presence of plasmid pIG101 is confirmed by its restriction pattern.
(ii) Production of TKL, (Ac)TKL, (i-but)TKL and (s-pent) TKL using S. avermitilis ATCC31272/pIG101
S. avermitilis ATCC31272/pIG101 is first inoculated into medium BW1, described above and allowed to grow for 10-12 days. Isolation of products as in the previous example gives a fraction containing (s-pent)-TKL and (i-but)-TKL, a fraction containing TKL, and a third fraction with minor amounts of (Ac)-TKL. The compounds are identified by their co-migration with authentic standards on GC analysis.

EXAMPLE 16

Construction of S. erythraea JC2/pIG1 and Production of TKL Derivatives
(i) Construction
Approximately 5 μg of plasmid pIG1 is transformed into protoplasts of S. erythraea JC2 and stable thiostrepton resistant colonies are isolated. From several such colonies, total DNA is obtained and analysed by Southern hybridisation, to confirm that the plasmid has integrated specifically into the portion of the eryAIII gene that encodes the C-terminal thioesterase/cyclase, by homologous recombination.
(ii) Production of Triketide Lactones Using S. erythraea JC2/pIG1
S. erythraea JC2/pIG1 is inoculated into tap water medium containing 50 μg/ml thiostrepton and allowed to grow for four days at 30° C. After this 20 ml of the mycelium is used to seed 500 ml of sucrose-succinate medium containing 50 μg/ml thiostrepton, in a 2 L flask with a single spring to reduce clumping, shaken at 280 rpm. After between 3.5 and 6 days, the broth is filtered to remove mycelia and then extracted three times with a quarter volume of ethyl acetate. The combined ethyl acetate extracts are dried over anhydrous sodium sulphate and solvent removed by evaporation. Analysis of the product mixture using GC and electrospray MS revealed that of a total of 5-6 mg/L of triketide lactone products, the major component was (s-pent)-TKL (about 1.5 mg/L), with other components present being (i-but)-TKL, TKL and a minor amount of (Ac)-TKL.

EXAMPLE 17

Construction of S. erythraea JC2/pIG101 and Production of TKL Derivatives
(i) Construction
Approximately 5 μg of plasmid pIG101 is transformed into protoplasts of S. erythraea JC2 and stable thiostrepton resistant colonies are isolated. From several such colonies, total DNA is obtained and analysed by Southern hybridisation, to confirm that the plasmid has integrated specifically into the portion of the eryAIII gene that encodes the C-terminal thioesterase/cyclase, by homologous recombination.
(ii) Production of Triketide Lactones Using S. erythraea JC2/pIG101
The same procedure as in Example 16 (ii) was followed. Analysis of the product mixture using GC and electrospray MS revealed that of a total of 5-6 mg/L of triketide lactone products, the major component was (s-pent)-TKL (about 1.5 mg/L), with other components present being (i-but)-TKL, TKL and a minor amount of (Ac)-TKL.

EXAMPLE 18

Construction of Plasmid pND20
This was accomplished in two stages:
(i) Construction of Plasmid pHISAVE
Plasmid pNEWAVETE was digested with EcoRI and HindIII and the vector was purified by gel electrophoresis. A synthetic oligonucleotide double-stranded insert encoding a 6-histidine tag and possessing these sites at either end (shown below) was ligated to the vector.

```
                                            (SEQ ID NO: 22)
(5'-AATTCACATCACCATCACCATCACTAGTAGGAGGTCTGGCCATC
TAGA-3');

(SEQ ID NO: 23)
(3'-GTAGTGGTAGTGGTAGTGATCATCCTCCAGACCGGTAGATCTTC
GC-5');
```

The ligation mixture was used to transform E.coli DH10B and individual colonies were screened for their plasmid content. The desired plasmid, pHISAVE was identified by its restriction pattern.
(Ii) Construction of Plasmid pND20
Plasmid pHISAVE was digested with NdeI and XbaI and the insert was ligated into pCJR24 digested with NdeI and XbaI. The ligation mixture was used to transform DH10B and individual colonies were screened for their plasmid content. The desired plasmid, pND20 was identified by its restriction pattern.

EXAMPLE 19

(i) Construction of S. erythraea JC3/pND20
Plasmid pND20 which has been isolated from E. coli ET12567 is used to transform protoplasts of S. erythraea JC3 and stable thiostrepton colonies are isolated.
(ii) Production of TKL and (Ac)TKL
S. erythraea JC3/pND20 is inoculated into tap water medium containing 50 μg/ml thiostrepton and allowed to grow for four days at 30° C. 20 ml of this is used to inoculate 500 ml of sucrose-succinate medium containing 50 μg/ml thiostrepton, in a 2 L flask with a single spring to reduce clumping and shaken at 280 rpm. After between 3.5 and 6 days, the broth is filtered to remove mycelia and then extracted three times with a quarter-volume of ethyl acetate. The combined ethyl acetate extracts are dried over anhydrous sodium sulphate and the solvent is removed by evaporation. Analysis of the product mixture using GC and electrospay MS reveals that of a total of about 20 mg/L of triketide lactone products, about ninety percent consisted of TKL and the remainder was Ac(TKL).

EXAMPLE 20

Construction of Plasmid pKW15

Plasmid pKW15 is a pT7-derived vector containing an insert comprising the loading module, the first extension module and the thioesterase of the ery PKS, suitable for subcloning into an SCP2*-based vector to obtain expression of a diketide synthase gene; and also suitable for insertion of heterologous DNA containing one or more intact modules. Plasmid pKW15 is obtained via several intermediate plasmids as follows (FIG. 12).

Construction of Plasmid pKW11

Plasmid pNTEP2 (Example 5) was digested with BglII, the sticky ends were filled in and religated, to produce plasmid pKW11. The insert in plasmid pKW11 consists of a chimaeric eryAI-eryAIII gene encompassing the loading didomain, module 1 and module 2 from DEBS1 and the thioesterase from DEBS3. The strategy to obtain this 'diketide synthase' was to remove the DNA encoding part of module 1, the whole of module 2 and part of the thioesterase, by digestion of plasmid pKW11 with EcoRV and EcoR1, and then to reconstitute module 1 and the N-terminal part of ACP1 by insertion of an appropriate PCR product, and similarly a PCR product was designed to replace the C-terminal part of ACP2 and the thioesterase. The two PCR products are joined by a unique BglII site created in the active site of the ACP, which involves an alteration in amino acid sequence of the hybrid ACP domain from EL (glutamic acid followed by leucine) as found in both ACP1 and ACP2 domains, to DL (aspartic acid followed by leucine). Such alterations in sequence at a PKS active site, with a view to retaining function, have not been previously attempted and it is not obvious that such altered sites should remain active.

Construction of Plasmids pKW12, pKW13, pKW14 and pKW15

For the PCR amplification of DNA for module 1, the following synthetic oligonucleotides were used as mutagenic primers, one containing an EcoRV site and the other a BglII site:

```
                                        (SEQ ID NO: 24)
    5'-GCAGGGATATCGCACGTTCCTGG-3'
    and (SEQ ID NO: 25)
    5'-CGCCGAGATCTGCGAAGGCCTGGTCGGCGGG-3'.
```

PCR was carried out on pNTEP2 as template using Pfu DNA polymerase and 30 cycles of 95% (1 min); annealing at 55% C (1 min) and extension at 72% C (2 min), in the presence of 10% (vol/vol) dimethylsulphoxide. The product (PCR1) was end-repaired and cloned into SmaI-cut phagemid pUC119 and the ligation mixture was used to transform E. coli TG1recO. Plasmid DNA was prepared from individual colonies and the desired plasmid (5.0 kbp) was identified by its restriction pattern and was designated pKW12.

For PCR amplification of the DNA for the 5' end of module and the thioesterase domain, the following oligonucleotides containing respectively a Bgl II site and an EcoRI site, were used as mutagenic primers:

```
                                        (SEQ ID NO: 26)
    5'-ATGAATTCCCTCCGCCCAGCCAG-3'
    and (SEQ ID NO: 27)
    5'-ACAGATCTCGGCTTCGACTCGCTGACCG-3'.
```

PCR was carried out on pNTEP2 as template exactly as described above for PCR1 and the product (PCR2) was end-repaired and cloned into SmaI-cut phagemid pUC119. The ligation mixture was used to transform E. coli TG1recO and plasmid DNA was prepared from individual colonies. The desired plasmid (4.1 kbp) was identified by its restriction pattern and was designated pKW13.

Plasmid pKW12 was digested with EcoRV and HindIII, and the 1.8 kbp insert was end-repaired, and then ligated together with plasmid pKW11 which had been linearised with EcoRV and treated with alkaline phosphatase. The ligation mixture was transformed into E. coli TG1recO and the plasmid content of individual colonies was checked. The desired plasmid (15.8 kbp) was identified in which the unique Eco RV site had been reconstituted, and this plasmid was designated pKW14.

Plasmid pKW13 was digested with BglII and EcoRI and the 0.9 kbp insert was ligated into plasmid pKW14 which had been digested with BglII and EcoRI. The ligation mixture was transformed into E. coli TG1recO and the plasmid content of the individual colonies was checked. The desired plasmid (9.32 kbp) was identified, in which the 0.9 kbp BglII-EcoRI fragment of pKW13 replaced the 9.5 kbp BglII-EcoRI segment of pKW14, and this plasmid was designated pKW15.

EXAMPLE 21

Construction and Use of Plasmid pKW16
(i) Construction

Plasmid pKW15 was digested with NdeI and XbaI and the insert was ligated into plasmid pRM52 which had also been digested with NdeI and XbaI. The ligation was transformed into E. coli TGI recO and isolated colonies were screened for their plasmid content. The desired plasmid was identified by its restriction map and was designated pKW16.

(ii) Use of Plasmid pKW16 for Construction of S. coelicolor CH999/pKW16

Plasmid pKW16 was used to transform the methylation-deficient strain E. coli ET12567 (MacNeil, D. J. et al. Gene (1992) 111:61-68) and the demethylated plasmid pKW16 DNA isolated from this strain was used to transform S. coelicolor CH999 (McDaniel, R. et al. Science (1993) 262:1546-1550. S. coelicolor protoplasts were transformed with pKW16 and stable thiostrepton resistant colonies were transferred to tap water medium agar plates containing 50 μg/ml thiostrepton.

(iii) Isolation and Characterisation of (2S)-methyl-(3R)-hydroxypentanoic acid and (2S)-methyl-(3R)-hydroxybutanoic acid.

A colony of S. coelicolor CH999/pKW16 was picked and transferred to 100 ml YEME supplemented with 50 μg/ml thiostrepton and allowed to grow at 30° C. After 4 days the broth was filtered to remove mycelia, acidified to pH 3.0 and solid sodium chloride added until the solution was saturated. The broth was extracted 5 times with an equal volume of ethyl acetate, and the combined ethyl acetate extracts were dried by extraction with saturated sodium chloride solution and concentrated by evaporation. Thin layer chromatography on silica gel plates, eluted with ethyl acetate:acetic acid 99:1 (v/v) and stained with potassium permanganate, showed the presence of a compound with the same mobility (Rf 0.55) as a reference sample of (2S)-methyl-(3R)-butanoic acid, which was not present in an extract obtained from *S. coelicolor* CH999 alone. Electrospray mass spectrometry (ESMS) analysis, in the negative ion mode, of the ethyl acetate extracts showed a major peak at m/e 117 not present in the control sample. In positive ion mode, and in the presence of formic acid, a peak was observed at m/e 119, which shifted to m/e 141 in the presence of added sodium ions. The exact mass of the sodium adduct was determined to be 141.05171 (the sodium salt of 2-methyl-3-hydroxybutanoic acid requires 141.05248). When a colony of *S. coelicolor* CH999/pKW16 was picked and transferred to 100 ml YEME supplemented with 50 µg/ml thiostrepton and allowed to grow at 30° C. for 7 days, an ethyl acetate extract prepared as above showed an additional peak, in ESMS operated in negative ion mode, at m/e 131. In ESMS operated in positive ion mode, and in the presence of added formic acid, the peak is found at m/e 155. The exact mass of this peak was determined to be 155.06973 (the sodium salt of 2-methyl-3-hydroxypentanoic acid requires 155.06890).

EXAMPLE 22

Construction of Plasmid pAR33

Plasmid pAR33 contains a hybrid Type I PKS comprising the ery loading module, extension module 1 of the ery PKS, extension module 12 of the rap PKS, and the ery chain-terminating thioesterase. It is constructed via several intermediate plasmids as follows (FIG. 13):

Construction of Plasmid pARRAP

The 4.7 kbp DNA segment of the rapC gene encoding module 12 of the rapamycin PKS was amplified by PCR employing the CloneAmp procedure (Raschtian, A. et al. Anal. Biochem. (1992) 91:91-97) and with the following two oligonucleotides as primers:

```
                                         (SEQ ID NO: 28)
5'-ACGCGUACUAGUCAGATCTGGGCATCAATTCGCTGACCGCGGTGGAA
CTGCGCAA-3', and (SEQ ID NO: 29)
5'-AUGGAGAUCUCUCAGATCTTGAATGCGGCGGCTGCGGGGATGGTGCT
GGCGTCA-3',
``` and using as template the DNA of clone _λ_-1C (Schwecke, T. et al. Proc. Natl. Acad. Sci. USA (1995) 92:7839-7843). Approximately 30-60 ng of the PCR product (4.7 kbp) is digested with uracil DNA glycosylase for 30 minutes at 37° C. in the presence of 25 ng pAMP18 vector DNA (Gibco BRL), the mixture is cooled on ice and transformed into *E. coli* TG1recO and individual colonies are checked for their plasmid content. The desired plasmid (7.4 kbp) is identified by its restriction map and is designated pARRAP.

Construction of Plasmid pAR32

Plasmid pARRAP is digested with BglII to release the 4.7 kbp fragment encoding rap module 12, which is purified by gel electrophoresis and then ligated into plasmid pKW15, which has been linearised by digestion with BglII. The ligation mixture is transformed into *E. coli* TG1recO and individual colonies are checked for their plasmid content. The desired plasmid is one in which the rap module 12 has the correct orientation with respect to the coding sequence of the open reading frame of the insert in pKW15, so that a hybrid triketide lactone synthase gene is produced. Such a plasmid is identified by its restriction pattern, and is designated pAR32.

Construction of Plasmid pAR33

Plasmid pAR32 contains an insert that can be excised by digestion with NdeI and XbaI, but there is an additional NdeI site in the insert that must be specifically protected against cleavage. This is done using the RecA protection method (Koob, M. et al. Nucl. Acids Res. (1992) 20:5831-5835)). The synthetic oligonucleotide 5'-GCACCCACGACGCCAC-CACCACATATGCCCTGCACCCTGCCCTCC-3' (SEQ ID NO: 30) (in which the NdeI site is underlined) is used together with purified RecA protein and ATP_S, to form a stable triplex DNA-protein complex that specifically protects the internal NdeI site in rap module 12 from digestion. The protected plasmid pAR32 is digested with NdeI and XbaI, producing the desired full-length insert (13.1 kbp), and this is ligated with plasmid pRM52 (Example 4) which has been digested with NdeI and XbaI. The ligation mixture is transformed into *E. coli* TG1 recO and individual colonies are screened for their plasmid content. The desired plasmid pAR33 is identified by its restriction pattern.

EXAMPLE 23

Construction of *S. erythraea* JC2/pAR33 and Preparation of TKL Derivatives (i) Construction Approximately 5 µg of plasmid pAR33 is transformed into protoplasts of *S. erythraea* JC2 and stable thiostrepton resistant colonies are selected. Total DNA from one such colony is isolated and analysed by Southern hybridisation, to confirm that the plasmid has integrated specifically into the chromosomal copy of the portion of the eryAIII gene that encodes the C-terminal thioesterase/cyclase. This strain is designated *S. erythraea* JC2/pAR33.

(ii) Production of a Novel Triketide Lactone by *S. erythraea* JC2/pAR33

*S. erythraea* JC2/pAR33 is inoculated into sucrose-succinate medium containing 50 µg/ml thiostrepton, and allowed to grow for five days at 28-30% C. After this time, the broth is filtered, and extracted twice with an equal volume of ethyl acetate, and the combined ethyl acetate extracts are dried over anhydrous sodium sulphate and the ethyl acetate is removed by evaporation under reduced pressure. Electrospray MS of the residue showed the presence of Ac-2-nor-3-epi-TKL (III, R=Me) and 2-nor-3-epi-TKL (III, R=Et).

EXAMPLE 24

Construction of Plasmid pAR8

Construction of a hybrid triketide lactone synthase containing the ery loading didomain and ery chain-terminating thioesterase/cyclase, and modules 11 and 12 of the rap PKS This example requires the initial construction of five separate plasmids, four housing separate elements of the target construct, and a fifth housing a gene conferring resistance to tetracycline. The inserts in these plasmids are sequentially combined by standard in vitro recombinant DNA techniques to form plasmid pAR5. A further three cloning steps lead to the final expression plasmid pAR8 (FIG. 14).

Construction of Plasmid pARLD

The segment of the ery AI gene from nucleotide 1 to nucleotide 1673, encoding the loading AT-ACP didomain, was amplified by PCR employing the CloneAmp procedure with the following two oligodeoxynucleotides as primers:

(SEQ ID NO: 31)
5'-ACGCGUACUAGUCCGATTAATTAAGGAGGACCATCAATGGCGGACCT
GTCAAAGCTC-3' and (SEQ ID NO: 2)
5'-AUGGAGAUCUCUCCGCTAGCGGTTCGCCGGGCGCCCCTTCGTTGGTC
CGCGCGCGGGTTTCCC-3' and plasmid pBK6.12 (Example 5) as template, to give plasmid pARLD.

Construction of Plasmid pAR11
Construction of Plasmid pAR12

The segment of the rapC gene of *S. hygroscopicus* (Schwecke, T. et al. Proc. Natl. Acad. Sci. USA (1995) 92:7839-7843) from nucleotide 112 to nucleotide 2095, the 5'-end of the DNA encoding rap module 11, is amplified by PCR employing the CloneAmp procedure with the following two olidodeoxvnucleotides as primers:

(SEQ ID NO: 32)
5'-AUGGAGAUCUCUCCGCTAGCGATTGTGGGTATGGCG-3'
and (SEQ ID NO: 33)
5'-ACGCGUACUAGUCCATGCATCTGCAGCACGGCGGCCTCA
TCACCGGA-3' and the DNA of recombinant bacteriophage _λ-1C (Schwecke, T. et al., Proc. Natl. Acad. Sci. USA (1995) 92:7839-7843) as the template. Approximately 30-60 ng of the PCR product (2.0 kbp) is digested with uracil DNA glycosylase for 30 min at 37° C. in the presence of 25 ng pAMP18 vector DNA, the mixture is cooled on ice and transformed into *E. coli* TG1 recO and individual colonies checked for their plasmid content. The desired plasmid (4.7 kbp) is identified by its restriction map and is designated pAR11.

The segment of the rapC gene of *S. hygroscopicus* (Schwecke, T. et al., Proc. Natl. Acad. Sci. USA (1995) 92:7839-7843) from nucleotide 7405 to nucleotide 9396, the 3' end of the DNA encoding rap module 12, is amplified by PCR employing the CloneAmp procedure with the following two oligodeoxynucleotides as primers:

(SEQ ID NO: 34)
5'-ACGCGUACUAGUCCATGCATTCCCGGAGCGGCGATCTGTGG-3'
and (SEQ ID NO: 35)
5'-AUGGAGAUCUCUCCCGCGGCCGCGCTGTCACGCACCAGCTTCAG
CAGTGCGTC-3' and the DNA of recombinant bacteriophage λ-1C (Schwecke, T. et al., Proc. Natl. Acad. Sci. USA (1995) 92:7839-7843) as template. Approximately 30-60 ng of the PCR product (2.0 kbp) is digested with uracil DNA glycosylase for 30 minutes at 37° C. in the presence of 25 ng pAMP18 vector DNA, the mixture is cooled on ice and transformed into *E. coli* TG1recO and individual colonies are checked for their plasmid content. The desired plasmid (4.7 kbp) is identified by its restriction map and is designated pAR12.

Construction of pARTE
The 1.3 kbp segment of the eryAIII gene, extending by 132 nucleotides 3' of the eryAIII stop codon to a KpnI site, and encoding the C-terminal chain-terminating thioesterase/cyclase of DEBS, is amplified by PCR employing the CloneAmp procedure with the following two oligodeoxynucleotides as primers:

(SEQ ID NO: 36)
5'-ACGCGUACUAGUCCGCGGCCGCGATCCTCGGGCATTCCAGC-3'
and (SEQ ID NO: 37)
5'-AUGGAGAUCUCUAAGCATTGGTAACTGTC-3',
and plasmid pEXDB3 (Roberts, G. A. et al. Eur J. Biochem. (1993) 214:305-311) as the template. Approximately 30-60 ng of the PCR product (1.3 kbp) is digested with uracil DNA glycosylase for 30 min at 37° C. in the presence of 25 ng pAMP18 vector DNA, the mixture is cooled on ice and transformed into *E. coli* TG1 recO and individual colonies checked for their plasmid content. The desired plasmid (4.0 kbp) is identified by its restriction ma and is designated pARTE.

Construction of Plasmid pARTr
The 1.3 kbp segment of plasmid pBR322 containing the tetracycline resistance gene is amplified by the CloneAmp procedure with the following two oligodeoxynucleotides as primers:

(SEQ ID NO: 38)
5'-ACGCGUACUAGUATCTAGACCATGCATGTTTGACAGCTTATCA
TC-3' and (SEQ ID NO: 39)
5'-AUGGAGAUCUCUAUCTAGACCATGCATGCCGCCGGCTTCCATT
CA-3' and plasmid pBR322 as the template. Approximately 30-60 ng of the PCR product (1.3 kbp) is digested with uracil DNA glycosylase for 30 minutes at 37° C. in the presence of 25 ng pAMP18 vector DNA, the mixture is cooled on ice and transformed into *E. coli* TG1recO and individual colonies are checked for their plasmid content. The desired plasmid (4.0 kbp) is identified by its restriction map and is designated pARTr.

Construction of Plasmid pAR1
Plasmid pARLD is digested with NheI and HindIII, and ligated to the 2.0 kbp NheI-HindIII insert obtained from plasmid pAR11. The ligation mixture is transformed into *E. coli* TG1recO and individual colonies are checked for their plasmid content. The desired plasmid is identified by its restriction map and is designated pAR1.

Construction of Plasmid pAR2
Plasmid pAR1 is linearised with NsiI and ligated with the NsiI fragment from pARTr. The ligation mixture is transformed into *E. coli* TG1recO and individual colonies are checked for their plasmid content. The desired plasmid is identified by its restriction map and is designated pAR2.

Construction of Plasmid pAR3
Plasmid pAR2 is digested with SpeI and XbaI and the insert is ligated with plasmid pAR12 which has been linearised with SpeI. The ligation mixture is transformed into *E. coli* TG1recO and individual colonies are checked for their plasmid content. The desired plasmid is identified by its restriction map and is designated pAR3.

Construction of Plasmid pAR4
Plasmid pAR3 is digested with NsiI and the vector is ligated to the NsiI fragment of pARTr, containing the tetracycline resistance gene. The ligation mixture is transformed into *E. coli* TG1recO and individual colonies, grown in the presence of tetracycline (12.5 µg/ml), are checked for their plasmid content. The desired plasmid is identified by its restriction map and is designated pAR4.

Construction of Plasmid pAR5

Plasmid pAR4 is digested with NotI and XbaI and ligated with a NotI-XbaI fragment obtained by digestion of plasmid pARTE. The ligation mixture is transformed into *E. coli* TG1recO and individual colonies, grown in the presence of tetracycline (12.5 μg/ml), are checked for their plasmid content. The desired plasmid is identified by its restriction map and is designated pAR5.

Construction of Plasmid pAR5-2

A 7.2 kbp segment of the rapC gene of *S. hygroscopicus* is excised from cosmid 13 (Schwecke, T. et al., Proc. Natl. Acad. Sci. USA (1995) 92:7839-7843) using BstXI and NdeI, purified by gel electrophoresis, and ligated with plasmid pAR5 which has also been digested with BstXI and NdeI. The ligation mixture is transformed into *E. coli* TG1recO and individual colonies, grown in the presence of tetracycline (12.5 μg/ml), are checked for their plasmid content. The desired plasmid (11.9 kbp) is identified by its restriction map and is designated pAR5-2.

Construction of Plasmid pAR5-3

A 3.0 kbp segment of plasmid pAR5 is excised by digestion with NdeI, purified by gel electrophoresis, and ligated with plasmid pAR5-2 which had been linearised with NdeI. The ligation mixture is transformed into *E. coli* TG1recO and individual colonies, grown in the presence of tetracycline (12.5 μg/ml), are checked for their plasmid content. The desired plasmid (14.9 kbp) is identified by its restriction map and is designated pAR5-3.

Construction of Plasmid pAR8

A 12.2 kbp fragment of plasmid pAR5-3 is excised using PacI and XbaI, purified by gel electrophoresis, and ligated with plasmid pRM52 (Example 4) which had been cut with PacI and XbaI. The ligation mixture is transformed into *E. coli* TG1recO and and individual colonies, grown in the presence of tetracycline (30.3 μg/ml), are checked for their plasmid content. The desired plasmid (14.9 kbp) is identified by its restriction map and is designated pAR8.

EXAMPLE 25

Construction of *S. erythraea* JC2/pAR8 and Production of TKL Derivatives (i) Construction Approximately 5-10 μg pAR8, isolated from *E. coli* DH10B (pARB) is used to transform *S. erythraea* JC2 protoplasts and stable thiostrepton resistant colonies are selected.

One of these colonies is selected and total DNA is prepared for Southern hybridisation analysis, to confirm that the plasmid has integrated specifically into the chromosomal copy of the portion of the eryAIII gene that encodes the C-terminal thioesterase/cyclase. This strain is designated *S. erythraea* JC2/pAR8

(ii) Production of 2,4-bisnor-3-epi-TKL and (Ac)-2,4-bisnor-3-epi-TKL

A colony of *S. erythraea* JC2/pAR8 is picked and transferred to sucrose-succinate medium supplemented with 50 μg/ml thiostrepton and allowed to grow at 30° C. After 3 days the broth is filtered and extracted twice with an equal volume of ethyl acetate. The combined ethyl acetate extracts are dried over anhydrous sodium sulphate and concentrated under reduced pressure. GC-MS of the residue shows the presence of 2,4-bisnor-3-epi-TKL (IV,R=E+) and (Ac)-2,4-bisnor-3-epi-TKL (IV, R=Me)

EXAMPLE 26

Construction of Plasmid pE1A2TE

Plasmid pE1A2TE (like plasmid pE1A2TE-2 also described herein) consists of a pT7.7 derived plasmid containing a hybrid Type I PKS gene comprising the ery loading module, the first extension module of the ery PKS, then the second extension module of the avr PKS, and the thioesterase of the ery PKS. It is constructed via several intermediate plasmids as follows (FIG. 15).

Construction of Plasmid pIG70

Plasmid pVE1446 which contains a portion of the avermectin PKS genes was obtained from *E. coli* ATCC 68250. Plasmid pVE1446 was digested with BamHI and the 7.0 kbp fragment between coordinates 6.05 and 13.05 was purified by gel electrophoresis and ligated into plasmid pUC119 which had been linearised with BamHI. The ligation mixture was used to transform *E. coli* TG1 recO and individual colonies were checked for their plasmid content. Of the two possible orientations of the BamHI insert pIG70 was selected such that when digested with PstI fragments of approximately 2.0 and 8.6 kbp were obtained and when digested with EcoRI fragments of approximately 5.1 and 5.5 kbp were obtained.

Construction of Plasmid pIG71

Plasmid pVE1446 which contains a portion of the avermectin PKS genes was obtained from *E. coli* ATCC 68250. Plasmid pVE1446 was digested with BamHI and the 7.1 kbp fragment between coordinates 13.05 and 20.15 was purified by gel electrophoresis and ligated into plasmid pUC119 which had been linearised with BamHI. The ligation mixture was used to transform *E. coli* TG1 recO and individual colonies were checked for their plasmid content. Of the two possible orientations of the BamHI insert pIG71 was selected such that when digested with EcoRI and XhoI 2 fragments of approximately 5 kbp were obtained.

Construction of Plasmid pIG70ΔPst pIG70 was cut with Pst1 and religated. pIG70ΔPst was isolated after transformation into *E. coli* TG1 recO.

Construction of Plasmid pIG70ΔEco pIG70 was cut with EcoRI and religated. pIG70ΔEco was isolated after transformation into *E. coli* TG1 recO Construction of Plasmid pIG71ΔSac pIG71 was cut with SacI and religated. pIG71ΔSac was isolated after transformation into *E. coli* TG1 recO Construction of Plasmid pIGPCRstart 50 pmol of each of synthetic oligonucleotides 8985 (5'-GAGCAGTCGTTCCGAGATCTCGGCTTCGATTCA-3'; SEQ ID NO: 40) which introduced a BglII site and 9204 (5'-GGGAGGAGATCAGATCCCAGAAGT -3'; SEQ ID NO: 41) were used by PCR to amplify a 300 bp product from 60 ng pIG70ΔEco. The PCR product was end-repaired, phosphorylated and ligated into pUC18 that had been linearised with SmaI and dephosphorylated. The ligation mixture was used to transform *E. coli* TG1 recO and individual colonies were checked for their plasmid content. The orientation of pIGPCRstart was identified by a double restriction enzyme digest with EcoRI and BglII to give a pattern that included a 300 by fragment.

Construction of Plasmid pIGPCRend 50 pmol of each of synthetic oligonucleotides 8986 (5'-GAGGGAGTCGAACCGAGATCTCGGAACGCGCGG-3'; SEQ ID NO: 42) which introduced a BglII site and 9205 (5'-GGGGGATCCTGGGGTCGGCCGGGCAGGGCAA-3'; SEQ ID NO: 43) were used by PCR to amplify a 440 by product from 60 ng pIG71ΔSac. The PCR product was end-repaired, phosphorylated and ligated into pUC18 that had been linearised with SmaI and dephosphorylated. The ligation mixture was used to transform *E. coli* TG1 recO and individual colonies were checked for their plasmid content. The orientation of pIGPCRend was identified by its restriction enzyme digest pattern.

Construction of Plasmid pIGstart+Middle

Plasmid pIGPCRstart was digested with PstI and the 300 bp fragment was purified by gel electrophoresis and ligated into plasmid pIG70ΔPst which had been linearised with PstI and dephosphorylated. The ligation mixture was used to transform *E. coli* TG1 recO and individual colonies were checked for their plasmid content. Plasmids which contained the correct orientation of the PstI-PstI insert were identified by DNA sequencing.

Construction of Plasmid pIGAve2Bgl

Plasmid pIGstart+middle was digested with BamHI and the 5.0 kbp fragment was purified by gel electrophoresis and ligated into plasmid pIGPCRend which had been cut with BamHI and dephosphorylated. The ligation mixture was used to transform *E. coli* TG1 recO and individual colonies were checked for their plasmid content.

Plasmids which contained the correct orientation of the BamHI-BamHI insert were identified by DNA sequencing.

Construction of Plasmid pE1A2TE

Plasmid pIGAve2Bgl was digested with BglII and the 6 kbp fragment was purified by gel electrophoresis and ligated into plasmid pKW15 (Example 16) which had been linearised with BglII and dephosphorylated. The ligation mixture was used to transform *E. coli* TG1 recO and individual colonies were checked for their plasmid content. Plasmids which contained the correct orientation of the BglII-BglII insert were identified by restriction enzyme digest with EcoRI.

EXAMPLE 27

Construction and Use of Plasmid pIG2

(i) Construction

Plasmid pE1A2TE was digested with NdeI and XbaI and the 11 kbp fragment was purified by gel electrophoresis and ligated into plasmid pRM52 (Example 4) which had been cut with NdeI and XbaI. The ligation mixture was used to transform *E. coli* TG1 recO and individual colonies were checked for their plasmid content.

(ii) Construction of *S. coelicolor* CH999/pIG2

Plasmid pIG2 which had been isolated from *E. coli* ET12567 (MacNeil, D. J. et al. Gene (1992) 111:61-68) was transformed into protoplasts of *S. coelicolor* CH999 and stable thiostrepton resistant colonies were isolated.

Individual colonies were checked for their plasmid content and the presence of plasmid pIG2 was confirmed by its restriction pattern.

EXAMPLE 28

Construction of Plasmid pIG102

Plasmid pE1A2TE was digested with NdeI and XbaI and the 11 kbp fragment was purified by gel electrophoresis and ligated into plasmid pCJR101 (Example 2) which had been cut with NdeI and XbaI. The ligation mixture was used to transform *E. coli* TG1 recO and individual colonies were checked for their plasmid content.

EXAMPLE 29

(i) Construction of Plasmid pKS22

Plasmid pKS22 is a pNTEP2-derived vector containing a DEBS1-TE-derived triketide synthase with a KS2 domain in the place of the KS1 domain. Plasmid pKS22 is obtained via several intermediate plasmids as follows (FIG. 16).

Construction of Plasmids pMO07, pMO08 and pMO09

For the PCR amplification for plasmid pMO07, the following synthetic oligonucleotides were used as mutagenic primers, one containing a HindIII site and the other an EcoRV site:

```
                                      (SEQ ID NO: 44)
    5'-GTCTCAAGCTTCGGCATCAGCGGCACCAA-3'
    and
                                      (SEQ ID NO: 45)
    5'-CGTGCGATATCCCTGCTCGGCGAGCGCA-3'.
```

For the PCR amplification for plasmid pMO08, the following synthetic oligonucleotides were used as mutagenic primers, one containing a PstI site and the other a HindIII site:

```
                                      (SEQ ID NO: 46)
    5'-CATGGCCTGCAGGCTGCCCGGGGAGGTCGACT-3'
    and
                                      (SEQ ID NO: 47)
    5'-CCCGAAGCTTGACACACCTGCCCGGCGCACCCCGT-3'.
```

For the PCR amplification for plasmid pMO09, the following synthetic oligonucleotides were used as mutagenic primers, one containing a Mun I site and the other a PstI site:

```
                                      (SEQ ID NO: 48)
    5'-GCGCGCCAATTGCGTGCACATCTCGAT-3'
    and
                                      (SEQ ID NO: 49)
    5'-CCTGCAGGCCATCGCGACGACCGCGACCGGTTCGCCG-3'.
```

PCR was carried out on pNTEP2 as template using Pwo DNA polymerase and one cycle of: 96° C. (1 min); annealing at 50° C. (3 min); and extension at 72° C. (1 min), and 25 cycles of: 96° C. (1 min); annealing at 50° C. (1 min); and extension at 72° C. (1 min) in the presence of 10% (vol/vol) dimethylsulphoxide. The products were end-repaired and cloned into pUC18 digested with SmaI and the ligation mixture was transformed into *E. coli* DH 10B. Plasmid DNA was prepared from individual colonies. The desired plasmids for pMO07 (3.8 kbp), pMO08 (3.9 kbp) and pMO09 (4.3 kbp) were identified by their restriction pattern and DNA sequencing.

Plasmid pMO08 was digested with HindIII, and the 1.2 kbp insert was cloned into pMO07 which had been digested with HindIII. The ligation mixture was transformed into *E. coli* DH 10B. The desired plasmid (5.0 kbp) was identified by its restriction pattern and designated pMO10.

Plasmid pMO09 was digested with PstI, and the 1.6 kbp insert was cloned into pMO10 which had been digested with PstI. The ligation mixture was transformed into *E. coli* DH 10B. The desired plasmid (6.6 kbp) was identified by its restriction pattern and designated pMO11.

Plasmid pMO11 was digested with MunI and EcoRV, and the 3.9 kbp fragment was cloned into pNTEPH (see below) which had been digested with MunI and EcoRV. The ligation mixture was transformed into *E. coli* DH 10B. The desired plasmid (13 kbp) was identified by its restriction pattern and designated pKS22.

Plasmid pNTEPH was obteined from pNTEP2 by removing the HindIII site. pNTEP2 was digested with HindIII, the 5' overhang was filled in with Klenow Fragment DNA Polymerase I and religated. The desired plasmid (13.6 kbp) was identified by its restriction pattern.

EXAMPLE 30

(i) Construction of Plasmid pIB018

Plasmid pIB018 is a pCJR24-derived vector containing a DEBS1TE-derived triketide synthase with KS1 in the place of KS2. Plasmid pIB018 is obtained via several intermediate plasmids as follows (FIG. 17A).

Construction of Plasmids pKSA, pKSB and pKSC

For the PCR amplification for plasmid pKSA, the following synthetic oligonucleotides were used as mutagenic primers, one containing a PstI site and the other a HindIII site:

```
                                        (SEQ ID NO: 50)
5'-GATGGCCTGCAGGCTGCCCGGCGGTGTGAGCA-3'
and
                                        (SEQ ID NO: 51)
5'-GCCGAAGCTTGAGACCCCCGCCCGGCGCGGTCGC-3'.
```

For the PCR amplification for plasmid pKSB, the following synthetic oligonucleotides were used as mutagenic primers, one containing an EspI site and the other a PstI site:

```
                                        (SEQ ID NO: 52)
5'-TGGCTTCGCTGGCGGACACGCTCAG-3'
and
                                        (SEQ ID NO: 53)
5'-CCTGCAGGCCATGCCGACGATCGCGATCGGCT-3'.
```

For the PCR amplification for plasmid pKSC, the following synthetic oligonucleotides were used as mutagenic primers, one containing a HindIII site and the other a BspEI site:

```
                                        (SEQ ID NO: 54)
5'-GTCAAGCTTCGGGGTGAGCGGGACGAA-3'
and
                                        (SEQ ID NO: 55)
5'-GCGTCCGGACGTGGCTCCAGCA-3'.
```

PCR was carried out on pNTEP2 as template using Pwo DNA polymerase and one cycle of: 96° (1 min); annealing at 50° (3 min); and extension at 72° (1 min), and 25 cycles of: 96° C. (1 min); annealing at 50° C. (1 min); and extension at 72° C. (1 min) in the presence of 10% (vol/vol) dimethylsulphoxide. The products were end-repaired and cloned into pUC18 digested with SmaI and the ligation mixture was transformed into E. coli DH 10B. Plasmid DNA was prepared from individual colonies. The desired plasmids for pKSA (4.0 kbp), pKSB (4.2 kbp) and pKSC (3.2 kbp) were identified by their restriction pattern.

Plasmid pKSA was digested with PstI, and the 1.2 kbp insert was cloned into pKSB which had been digested with PstI. The ligation mixture was transformed into E. coli DH 10B. The desired plasmid (5.5 kbp) was identified by its restriction pattern and designated pKSD.

Plasmid pKSC was digested with HindIII, and the 0.5 kbp insert was cloned into pKSC which had been digested with HindIII. The ligation mixture was transformed into E. coli DH 10B. The desired plasmid (6.0 kbp) was identified by its restriction pattern and designated pKSE.

Plasmid pKSE was digested with EspI and BspeEI, ant the 3.3 kbp fragment was cloned into pUCTE which had been digested with EspI and BspeEI. The ligation mixture was transformed into E. coli DH 10B. The desired plasmid (13.9 kbp) was identified by its restriction pattern and designated pIB004.

Plasmid pIB004 was digested with NdeI and XbaI, and the 11.2 kbp insert was cloned into pCJR24 which had been digested with NdeI and XbaI. The ligation mixture was transformed into E. coli DH 10B. The desired plasmid (15.9 kbp) was identified by its restriction pattern and designated pIB018.

(ii) Use of Plasmid pIB018 for Contruction of S. erythraea NRRL2338/pIB018

Approximately 5 µg plasmid pIB018 is transformed into protoplasts of S. erythraea NRRL 2338 and stable thiostrepton resistant colonies are isolated. From several colonies total DNA is obtained and analysed by Southern hybridisation, to confirm that the plasmid has integrated into the end of module2 of eryAI.

S. erythraea NRRL2338/pIB018 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton in a 2 L flask with a single spring to reduce clumping, shaken at 300 rpm. After 6 days the broth was filtered, adjusted to pH 4 and extracted three times with an equal volume of ethyl acetate. The solvent was removed by evaporation. Triketide lactone products (10 mg/L) were identified by GC-MS and NMR. The major component was (2R, 3S, 4S, 5R)-2,4-dimethyl-3,5-dihydroxy-n-hexanoic acid δ lactone; (2R, 3S, 4S, 5R)-2,4-dimethyl-3,5-dihydroxy-n-heptanoic acid δ lactone was also found:

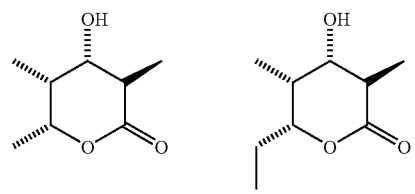

The following macrolides were identified by HPLC/MS:

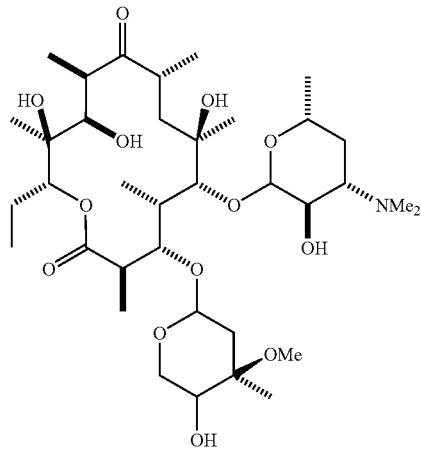

-continued

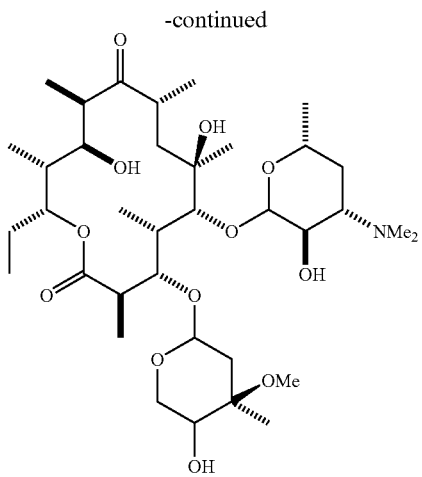

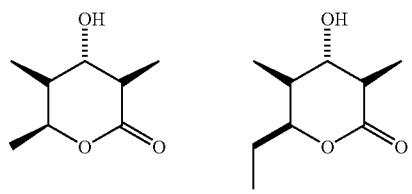

The following macrolides were identified by HPLC/MS:

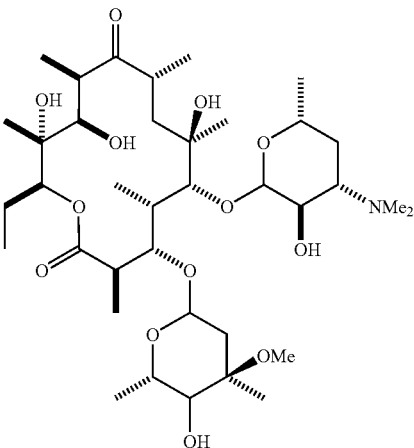

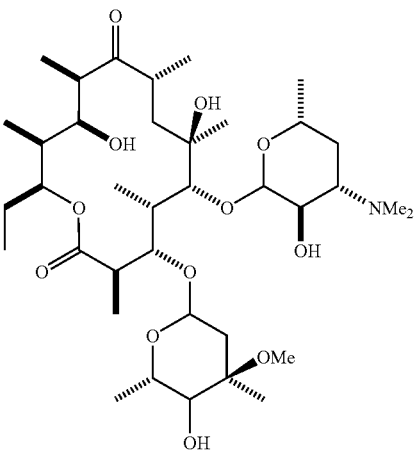

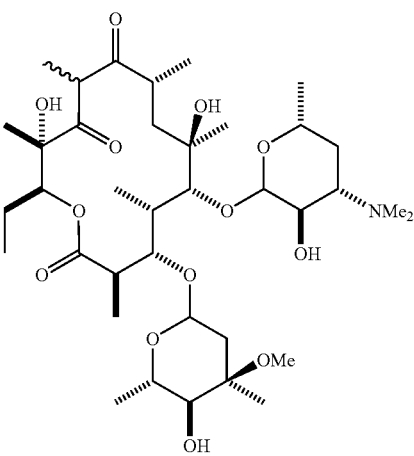

EXAMPLE 31

(i) Construction of Plasmid pIB017

Plasmid pIB017 is a pCJR24-derived vector containing a DEBS1TE-derived triketide synthase with KS2 in the place of KS1 and KS1 in the place of KS2. Plasmid pIB017 is obtained via several intermediate plasmids as follows (FIG. 17B).

Plasmid pIB004 was digested with EcoRV and EcoRI, and the 7.2 kbp fragment was cloned into pKS22 which had been digested with EcoRV and EcoRI. The ligation mixture was transformed into E. coli DH 10B. The desired plasmid (13.6 kbp) was identified by its restriction pattern and designated pIB009.

Plasmid pIB009 was digested with NdeI and XbaI, and the 11.2 kbp insert was cloned into pCJR24 which had been digested with NdeI and XbaI. The ligation mixture was transformed into E. coli DH 10B. The desired plasmid (15.9 kbp) was identified by its restriction pattern and designated pIB017.

(ii) Construction of S. erythraea NRRL2338/pIB017

Approximately 5 μg plasmid pIB017 is transformed into protoplasts of S. erythraea NRRL 2338 and stable thiostrepton resistant colonies are isolated. From several colonies total DNA is obtained and analysed by Southern hybridisation, to confirm that the plasmid has integrated into the end of module 2 of eryAI.

S. erythraea NRRL2338/pIB017 is inoculated into tryptic soy broth containing 50 μg/ml thiostrepton and allowed to grow for three days at 30° C. 20 ml of this seed culture are used to inoculate 400 ml of sucrose-succinate medium containing 50 μg/ml thiostrepton in a 2 L flask with a single spring to reduce clumping, shaken at 300 rpm. After 6 days the broth was filtered, adjusted to pH 4 and extracted three times with an equal volume of ethyl acetate. The solvent was removed by evaporation. Analysis of triketide lactones (0.4 mg/L) was done by GC-MS, optical rotation and NMR. The compunds isolated were found to be (2R, 3S, 4S, 5S)-2,4-dimethyl-3,5-dihydroxy-n-hexanoic acid δ lactone; and (2R, 3S, 4S, 5S)-2,4-dimethyl-3,5-dihydroxy-n-heptanoic acid δ lactone.

-continued

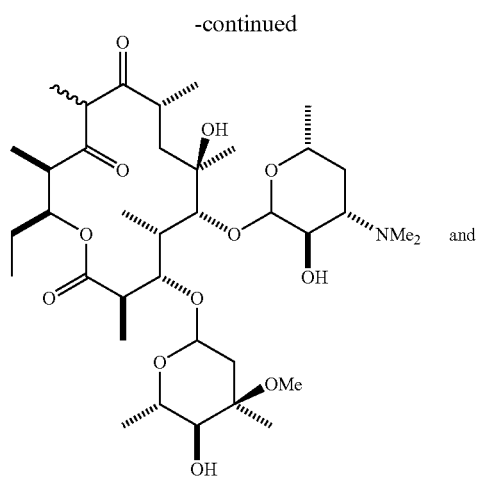

EXAMPLE 32

(I) Construction of Plasmid pIB015

Plasmid pIB015 is a pCJR24-derived vector containing a diketide synthase with LD, KS1, AT2, KR2, ACP2/6 and TE. Plasmid pIB015 is obtained via several intermediate plasmids as follows (FIG. 18).

Plasmid pIB009 was digested with PstI to remove a 4.4 kbp fragment, and religated. The ligation mixture was transformed into E. coli DH 10B. The desired plasmid (9.2 kbp) was identified by its restriction pattern and designated pIB011.

Plasmid pIB011 was digested with NdeI and XbaI, and the 6.8 kbp insert was cloned into pCJR24 which had been digested with NdeI and XbaI. The ligation mixture was transformed into E. coli DH 10B. The desired plasmid (9.2 kbp) was identified by its restriction pattern and designated pIB015.

(ii) Use of Plasmid pIB015 for Contruction of S. erythraea JC2/pIB015

Approximately 5 µg plasmid pIB015 is transformed into protoplasts of S erythraea JC2 and stable thiostrepton resistant colonies are isolated. From several colonies total DNA is obtained and analysed by Southern hybridisation, to confirm that the plasmid has integrated into the TE.

S. erythraea JC2/pIB015 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton, 0.1 mg/ml 4-pentynoic acid and 0.1 mg/ml 3-tetradecylsulfanyl-propionic acid in a 2 L flask with a single spring to reduce clumping, shaken at 300 rpm. After 6 days the broth was filtered, adjusted to pH 3 and extracted three times with an equal volume of ethyl acetate. The solvent was removed by evaporation. Analysis of diketide acid was done by GC-MS equipped with a chiral column (Hydrodex-β-PM 25 m×0.25 mm ID (Machery-Nagel GmbH & COKG, Germany)) using all 4 synthetic stereoisomers of the diketide acid as standards. The compound produced was identified as (2R, 3S)-2-methyl, 3-hydroxy pentanoic acid.

iii) Use of Plasmid pIB015 for Contruction of S. erythraea ORF5/pIB015

Approximately 5 µg plasmid pIB015 is transformed into protoplasts of S. erythraea ORF5 and stable thiostrepton resistant colonies are isolated. From several colonies total DNA is obtained and analysed by Southern hybridisation, to confirm that the plasmid has integrated into module 2 of eryAI.

S. erythraea ORF5/pIB015 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton in a 2 L flask with a single spring to reduce clumping, shaken at 300 rpm. After 6 days the broth was filtered and extracted three times with an equal volume of ethyl acetate. The solvent was analysed by ESMS. The following compounds were detected:

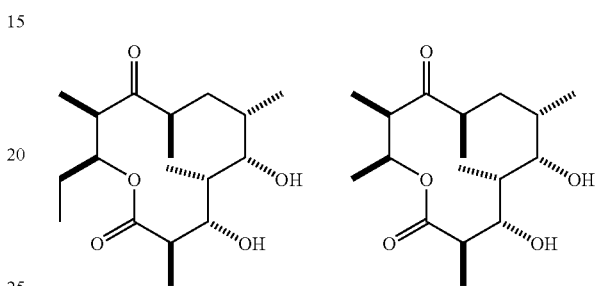

EXAMPLE 33

(i) Construction of Plasmid pIB016

Plasmid pIB016 is a pCJR24-derived vector containing a diketide synthase with LD, KS2, AT2, KR2, ACP2/6 and TE. Plasmid pIB016 is obtained via several intermediate plasmids as follows (FIG. 18).

Plasmid pIB009 was digested with HindIII to remove a 4.4 kbp fragment, and religated. The ligation mixture was transformed into E. coli DH 10B. The desired plasmid (9.2 kbp) was identified by its restriction pattern and designated pIB012.

Plasmid pIB012 was digested with NdeI and XbaI, and the 6.8 kbp insert was cloned into pCJR24 which had been digested with NdeI and XbaI. The ligation mixture was transformed into E. coli DH 10B. The desired plasmid (9.2 kbp) was identified by its restriction pattern and designated pIB016.

ii) Use of Plasmid pIB016 for Contruction of S. erythraea ORFS/pIB016

Approximately 5 µg plasmid pIB016 is transformed into protoplasts of S. erythraea ORF5 and stable thiostrepton resistant colonies are isolated. From several colonies total DNA is obtained and analysed by Southern hybridisation, to confirm that the plasmid has integrated into module 2 of eryAI.

S. erythraea ORF5/pIB016 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton in a 2 L flask with a single spring to reduce clumping, shaken at 300 rpm. After 6 days the broth was filtered and extracted three times with an equal volume of ethyl acetate. The extract was analysed by ESMS. The following compounds were detected:

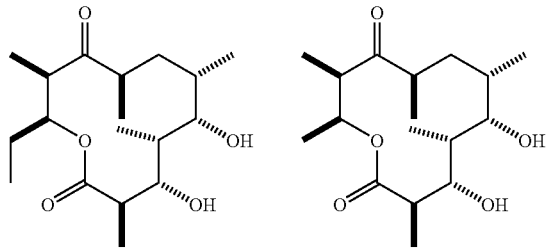

EXAMPLE 34

Construction of Plasmid pJLK15

Plasmid pJLK15 is a pCJR24 based plasmid containing a PKS gene comprising the ery loading module, the first and the second extension modules of the ery PKS and the ery chain-terminating thioesterase except that the DNA segment between the end of the acyltransferase and the beginning of the ACP of the second ery extension module has been substituted by the equivalent segment of module 13 of the rap PKS. It was constructed via several intermediate plasmids as follows (FIG. 19).

Construction of Plasmid pJLK01

The approximately 0.46 kbp DNA fragment of the erAI gene of *S. erythraea* was amplified by PCR using as primers the synthetic oligonucleotides: 5'-GGAGTACTGC-GAGGGCGTGGGCAT-3' (SEQ ID NO: 56) and 5'-CAC-CTAGGACCGCTTCCCAGTCGACC-3'(SEQ ID NO: 57) and plasmid pNTEPH as template. The PCR product was treated with T4 polynucleotide kinase and then ligated with plasmid pUC18, which had been linearised by digestion with SmaI and then treated with alkaline phosphatase. The ligation mixture was used to transform *E. coli* DH10B and individual colonies were checked for their plasmid content. The desired plasmid pJLK01 was identified by its restriction pattern and DNA sequencing.

Construction of Plasmid pJLK08

The approximately 1.47 kbp DNA fragment of the erAI gene of *S. erythraea* was amplified by PCR using as primers the synthetic oligonucleotides:

```
                                        (SEQ ID NO: 58)
5' -TACCTAGGCCGGGCCGGACTGGTCGACCTGCCGGGTT-3'
and
                                        (SEQ ID NO: 59)
5' -ATCCTCAGGCTCTCCGTCTCCGGTTCTCC-3'
and
``` plasmid pNTEPH as template. The PCR product was treated with T4 polynucleotide kinase and then ligated with plasmid pUC18, which had been linearised by digestion with SmaI and then treated with alkaline phosphatase. The ligation mixture was used to transform *E. coli* DH10B and individual colonies were checked for their plasmid content. The desired plasmid pJLK08 was identified by its restriction pattern and DNA sequencing.

Construction of Plasmid pJLK09

The approximately 1.12 kbp DNA fragment of the erAI gene of *S. erythraea* was amplified by PCR using as primers the synthetic oligonucleotides:

```
                                        (SEQ ID NO: 60)
5' -TACCTGAGGGACCGGCTAGCGGGTCTGCCGCGTG-3'
and
                                        (SEQ ID NO: 61)
5' -CTTCTAGACTATGAATTCCCTCCGCCCAGC-3'
and
``` plasmid pNTEPH as template. The PCR product was treated with T4 polynucleotide kinase and then ligated with plasmid pUC18, which had been linearised by digestion with SmaI and then treated with alkaline phosphatase. The ligation mixture was used to transform *E. coli* DH10B and individual colonies were checked for their plasmid content. The desired plasmid pJLK09 was identified by its restriction pattern and DNA sequencing.

Construction of Plasmid pJLK10

Plasmid pJLK08 was digested with PstI and Bsu36I and the insert was ligated with plasmid pJLK09 which had been digested with PstI and Bsu36I. The ligation mixture was used to transform *E. coli* DH10B and individual colonies were checked for their plasmid content. The desired plasmid pJLK10 was identified by its restriction pattern.

Construction of Plasmid pJLK11

Plasmid pJLK01 was digested with PstI and AvrII and the insert was ligated with plasmid pJLK10 which had been digested with PstI and AvrII. The ligation mixture was used to transform *E. coli* DH10B and individual colonies were checked for their plasmid content. The desired plasmid pJLK11 was identified by its restriction pattern.

Construction of Plasmid pJLK12

Plasmid pJLK11 was digested with ScaI and the 4.7 kbp fragment was ligated with plasmid pCJR34 which had been digested with ScaI. The ligation mixture was used to transform *E. coli* DH10B and individual colonies were checked for their plasmid content. The desired plasmid pJLK12 was identified by its restriction pattern. pCJR34 was constructed in the following way. pNTEP2 was digested with NdeI and XbaI and cloned into pUC19 which had previously been digested with NdeI and XbaI. The desired plasmid pCJR34 was identified by its restriction pattern.

Construction of Plasmid pJLK13

Plasmid pJLK12 was digested with NdeI and XbaI and the 11.2 kbp fragment was ligated with plasmid pCJR24 which had been digested with NdeI and XbaI. The ligation mixture was used to transform *E. coli* DH10B and individual colonies were checked for their plasmid content. The desired plasmid pJLK13 was identified by its restriction pattern.

Construction of Plasmid pJLK14

The approximately 3.3 kbp DNA of the rapC gene of *S. hygroscopicus* encoding the reduction loop of module 13 was amplified by PCR using as primers the synthetic oligonucleotides:

```
                                        (SEQ ID NO: 62)
5' -CGCCTAGGCACCACCACAACCCGGGTACTGGACC-3'
and
                                        (SEQ ID NO: 63)
5' -TAGCTAGCCGGGCGCTCAGGGGCTGCGAGCCGACCT-3'
and
``` cosmid cos 31 (Schwecke, T. et al. (1995) Proc. Natl. Acad. Sci. USA 92:7839-7843) as template. The PCR product was treated with T4 polynucleotide kinase and then ligated with plasmid pUC18, which had been linearised by digestion with SmaI and then treated with alkaline phosphatase. The ligation mixture was used to transform *E. coli* DH10B and individual colonies were checked for their plasmid content. The desired plasmid pJLK14 was identified by its restriction pattern and DNA sequencing.

Construction of Plasmid pJLK15

Plasmid pJLK14 was digested with AvrII and NheI and the 3.3 kbp fragment was ligated with plasmid pJLK13 which had been digested with AvrII and NheI. The ligation mixture was used to transform E. coli DH10B and individual colonies were checked for their plasmid content. The desired plasmid pJLK15 was identified by its restriction pattern.

EXAMPLE 35

Use of Plasmid pJLK15 for Construction of JC2/pJLK15

Approximately 5 µg plasmid pJLK15 is transformed into protoplasts of S. erythraea JC2 and stable thiostrepton resistant colonies are isolated. From several colonies total DNA is obtained and analysed by Southern hybridisation, to confirm that the plasmid has integrated into the TE. JC2/pJLK15 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton in a 2 L flask with a single spring to reduce clumping, shaken at 300 rpm. After 6 days the broth was filtered, adjusted to pH 3 and extracted three times with an equal volume of ethyl acetate. The solvent was removed by evaporation and the residue dissolved in methanol (5 ml) and analysed by electrospray mass spectroscopy. The major products were identified as (2R, 4R, 5R)-2,4-dimethyl-5-hydroxy-n-hexanoic acid b-lactone ($C_8H_{14}O_2$; MH$^+$: calc. 143.1072, found 143.110; MNa$^+$: calc.165.0891, found 165.093) and as (2R, 4R, 5R)-2,4-dimethyl-5-hydroxy-n-heptanoic acid δ-lactone ($C_9H_{16}O_2$; MH$^+$: calc. 156.1150, found 156.118; MNa$^+$: calc. 178.0970, found 178.099).

EXAMPLE 36

Construction of Plasmid pJLK18

Plasmid pJLK18 is a pCJR24 based plasmid containing a PKS gene comprising the ery loading module, the first and the second extension modules of the ery PKS and the ery chain-terminating thioesterase except that the DNA segment between the end of the acyltransferase and the beginning of the ACP of the second ery extension module has been substituted by the equivalent segment of module 4 of the rap PKS. It was constructed via several intermediate plasmids as follows (FIG. 20).

Construction of Plasmid pJLK16

The approximately 2.8 kbp DNA fragment of the rapA gene of S. hygroscopicus encoding the reduction loop of module 4 was amplified by PCR using as primers the synthetic oligonucleotides:

```
                                            (SEQ ID NO: 64)
5'-CCTAGGCACCACCACGGCCCGGCTGCTGGACCTT-3'
and
                                            (SEQ ID NO: 65)
5'-CCTCAGCCTGTCACCGGTAGAGGCGGCCCT-3'
and
``` cosmid cos 25 (Schwecke, T. et al. (1995) Proc. Natl. Acad. Sci. USA 92:7839-7843) as template. The PCR product was treated with T4 polynucleotide kinase and then ligated with plasmid pUC18, which had been linearised by digestion with SmaI and then treated with alkaline phosphatase. The ligation mixture was used to transform E. coli DH10B and individual colonies were checked for their plasmid content. The desired plasmid pJLK16 was identified by its restriction pattern and DNA sequencing.

Construction of Plasmid pJLK17

Plasmid pJLK16 was digested with AvrII and Bsu36I and the 2.8 kbp fragment was ligated with plasmid pJLK12 which had been digested with AvrII and Bsu36I. The ligation mixture was used to transform E. coli DH10B and individual colonies were checked for their plasmid content. The desired plasmid pJLK17 was identified by its restriction pattern.

Construction of Plasmid pJLK18

Plasmid pJLK17 was digested with NdeI and XbaI and the 11.2 kbp fragment was ligated with plasmid pCJR24 which had been digested with NdeI and XbaI. The ligation mixture was used to transform E. coli DH10B and individual colonies were checked for their plasmid content. The desired plasmid pJLK18 was identified by its restriction pattern.

EXAMPLE 37

Use of Plasmid pJLK18 for Construction of JC2/pJLK18

Approximately 5 µg plasmid pJLK18 is used to transform protoplasts of S. erythraea JC2 and stable thiostrepton resistant colonies are isolated. From several colonies total DNA is obtained and analysed by Southern hybridisation, to confirm that the plasmid has integrated into the TE. S. erythraea JC2/pJLK18 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton, 0.1 mg/ml 4-pentynoic acid and 0.1 mg/ml 3-tetradecylsulfanyl-propionic acid in a 2 L flask with a single spring to reduce clumping, shaken at 300 rpm. After 6 days the broth was filtered, adjusted to pH 3 and extracted three times with an equal volume of ethyl acetate. The solvent was removed by evaporation and the residue dissolved in methanol (5 ml) and analysed by electrospray mass spectroscopy. The major products were identified as (E, 4R, 5R)-2,4-dimethyl-5-hydroxy-n-2-hexenoic acid ($C_8H_{14}O_3$; MH$^+$: calc. 159.1021, found 159.098; MNa$^+$: calc.181.0841, found 181.079) and (E, 4R,-5R)-2,4-dimethyl-5-hydroxy-n-2-heptenoic acid ($C_9H_{16}O_2$; MH$^+$: calc. 173.1178, found 173.118; MNa$^+$: calc.195.0997, found 195.104).

EXAMPLE 38

Construction of Plasmid pJLK21 (FIG. 21)

Construction of Plasmid pJLK19

For the PCR amplification of an approximately 1.3 kbp DNA fragment for plasmid pJLK19, the following synthetic oligonucleotides were used as primers:

```
                                            (SEQ ID NO: 54)
5'-GTCAAGCTTCGGGGTGAGCGGGACGAA-3'
and
                                            (SEQ ID NO: 66)
5'-ATCCTAGGACCGCTTCCCAGTCGACCGCGACA-3'
```

PCR was carried out on pNTEPH as template. The PCR product was treated with T4 polynucleotide kinase and then ligated with plasmid pUC18, which had been linearised by digestion with SmaI and then treated with alkaline phosphatase. The ligation mixture was used to tranform E. coli DH10B and individual colonies were checked for their plasmid content. The desired plasmid pJKL19 was identified by its restriction pattern.

Construction of Plasmid pJLK20

Plasmid pIB011 was digested with HindIII and NdeI and the 2.9 kbp fragment was cloned into pJKL19 which had been digested with HindIII and NdeI. The ligation mixture was used to tranform *E. coli* DH10B and individual colonies were checked for their plasmid content. The desired plasmid pJKL20 was identified by its restriction pattern.

Construction of Plasmid pJLK21

Plasmid pJKL20 was digested with AvrII and NdeI cloned into pJLK15 which had been digested with AvrII and NdeI. The ligation mixture was used to tranform *E. coli* DH10B and individual colonies were checked for their plasmid content. The desired plasmid pJKL21 was identified by its restriction pattern.

EXAMPLE 39

Use of Plasmid pJKL21 for Construction of JC2/pJKL21

Approximately 5 µg plasmid pJKL21 is transformed into protoplasts of JC2 and stable thiostrepton resistant colonies are isolated. From several colonies total DNA is obtained and analysed by Southern hybridisation, to confirm that the plasmid has integrated into the thioesterase. JC2/pJKL21 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton, 0.1 mg/ml 4-pentynoic acid and 0.1 mg/ml 3-tetradecylsulfanyl-propionic acid in a 2 L flask with a single spring to reduce clumping, shaken at 300 rpm. After 6 days the broth was filtered, the pH adjusted to pH 3 and extracted 3 times with an equal volume of ethyl acetate. The solvent was removed by evaporation and the residue dissolved in methanol (5 ml) and analysed by electrospray mass spectroscopy. The major products were identified as (2R)-2-methyl-butanoic acid ($C_5H_{10}O_2$; MH$^+$: calc. 103.0759, found 103.071; MNa$^+$: calc. 125.0578, found 125.052) and as (2R)-2-methyl-pentanoic acid.

EXAMPLE 40

Construction of Plasmid pJLK22

Plasmid pJKL20 was digested with AvrII and NdeI cloned into pJLK18 which had been digested with AvrII and NdeI. The ligation mixture was used to tranform *E. coli* DH10B and individual colonies were checked for their plasmid content. The desired plasmid pJKL22 was identified by its restriction pattern.

EXAMPLE 41

Use of Plasmid pJKL22 for Construction of *S. erythraea* JC2/pJKL22

Approximately 5 µg plasmid pJKL22 is transformed into protoplasts of JC2 and stable thiostrepton resistant colonies are isolated. From several colonies total DNA is obtained and analysed by Southern hybridisation, to confirm that the plasmid has integrated into the thioesterase.

JC2/pJKL22 is inoculated into tryptic soy broth containing 50 µg/ml thiostrepton and allowed to grow for three days at 30° C. 20 ml of this seed culture are used to inoculate 400 ml of sucrose-succinate medium containing 50 µg/ml thiostrepton, 0.1 mg/ml 4-pentynoic acid and 0.1 mg/ml 3-tetradecylsulfanyl-propionic acid in a 2 L flask with a single spring to reduce clumping, shaken at 300 rpm. After 6 days the broth was filtered, the pH adjusted to pH 3 and extracted 3 times with an equal volume of ethyl acetate. The solvent was removed by evaporation and the residue dissolved in methanol (5 ml) and analysed by electrospray mass spectroscopy. The major products were identified as (E)-2-methyl-butenoic acid ($C_5H_8O_2$; MH$^+$: calc. 101.0602, found 101.062; MNa$^+$: calc.123.0422, found 123.043) and (E)-2-methyl-pentenoic acid ($C_6H_{10}O_2$; MH$^+$: calc. 115.0759, found 115.077; MNa$^+$: calc.137.0578, found 137.058).

EXAMPLE 42

For the construction of plasmid pKR1-0, a derivative of pCJR24 which encodes a ketolactone synthase, several intermediate plasmids were constructed (FIG. 22).

Construction of Plasmid p37

The 1.4 kbp segment of plasmid pNTEP2 containing from nucleotide 9838 to 11214 (encoding amino acids 3279 to the end of DEBS1-TE) is amplified by PCR with the following two synthetic oligonucleotides as primers:

```
                                        (SEQ ID NO: 67)
5' -GCCACTAGTGTGGCGTGGGGGCTGTGGG-3'
and
                                        (SEQ ID NO: 68)
5' -TGAATTCCCTCCGCCCAGCCAGGCGTCGAT-3'
and
``` plasmid pNTEP2 as template. The PCR product was end-repaired and ligated with plasmid pUC18, which had been linearised by digestion with SmaI and then treated with alkaline phosphatase. The ligation mixture was used to transform *E. coli* DH10B and individual colonies were checked for their plasmid content. The desired plasmid p37 in which an SpeI site was introduced at the 5' end of this fragment was identified by its restriction pattern and by DNA sequencing.

Construction of Plasmid p37N

Plasmid p37 was digested with EcoRI and KpnI and the 1.4 fragment was ligated to pNTEP2 previously digested with EcoRI and KpnI. The ligation mixture was used to transform *E. coli* DH10B and individual colonies were checked for their plasmid content. The desired plasmid p37N was identified by its restriction pattern.

Construction of Plasmid pSCA7

The 1.1 kbp DNA segment of the erAI gene *S. erythraea* extending from nucleotide 8202 to nucleotide 9306 was amplified by PCR using as primers the synthetic oligonucleotides:

```
                                        (SEQ ID NO: 69)
5' -CCTGGAGTACTGCGAGGGCGTG--3'
and
                                        (SEQ ID NO: 70)
5' -CTGACTAGTGGCGGTGACGTGGGCGGGGAAA-3'
and
``` plasmid pNTEP2 as template. The PCR product was end-repaired and ligated with plasmid pUC18, which had been linearised by digestion with SmaI and then treated with alkaline phosphatase. The ligation mixture was used to transform *E. coli* DH10B and individual colonies were checked for their plasmid content. The desired plasmid pSCA7 in which an SpeI site has been introduced at the 3' end of this PCR product was identified by its restriction pattern and by DNA sequencing.

Construction of Plasmid pSH

Plasmid p37N was digested with SpeI and HindIII and the 1.4 kbp fragment was ligated with plasmid pSCA7 previously digested with SpeI and HindIII. The ligation mixture was used to transform E. coli DH10B and individual colonies were checked for their plasmid content. The desired plasmid pSH was identified by its restriction pattern.

Construction of Plasmid pUCTE

Plasmid pNTEP2 was digested with BglII and HindIII and the 11.2 kbp insert was ligated to BamHI and HindIII digested plasmid pUC18. The ligation mixture was used to transform E. coli DH10B and individual colonies were checked for their plasmid content. The desired plasmid PUCTE was identified by its restriction pattern.

Construction of Plasmid pUC1-0

The 3.9 kbp ScaI restriction fragment of PUCTE was substituted for the 3.4 kbp ScaI restriction fragment of pSH. The desired plasmid pUC1-0 was identified by its restriction pattern.

Construction of Plasmid pKR1-0

The 10.7 kbp NdeI and XbaI restriction fragment of pUC1-0 was ligated to NdeI and XbaI digested pCJR24. The ligation mixture was used to transform E. coli DH10B and individual colonies were checked for thier plasmid content. The desired plasmid pKR1-0 was identified by its restriction pattern.

EXAMPLE 43

Construction and Use of S. erythraea JC2/pKR1-0

(i) Construction

Approximately 5 μg of plasmid pKR1-0 was used to transform protoplasts of S. erythraea JC2 and stable thiostrepton resistant colonies were isolated. From several such colonies, total DNA was obtained and analysed by Southern hybridisation, to confirm that the plasmid had integrated specifically into the portion of the eryAIII gene that encodes the C-terminal thioesterase/cyclase, by homologous recombination. One such clone was selected and designated S. erythraea JC2/pKR1-0.

(ii) Production of Triketide Lactones Using S. erythraea JC2/pKR1-0

S. erythraea JC2/pKR1-0 was inoculated into sucrose-succinate medium containing 10 μg/ml thiostrepton and allowed to grow for four days at 30° C. After this time the broth is filtered to remove mycelia and then extracted twice with ethyl acetate. The combined ethyl acetate extracts are analysed by gas chromatography, mass spectrometry and NMR and it is found that the major products were (2R,4R,5R)-2,4-dimethyl-3-keto-5-hydroxy-n-hexanoic acid δ_lactone and (2R, 4R,5R)-2,4-dimethyl-3-keto-5-hydroxy-n-heptanoic acid δ lactone in total yields of 20 mg/L for each lactone.

EXAMPLE 44

For the construction of an S. erythraea strain that produces ketolides, the construction of plasmid pKETO required the construction of the following intermediate plasmids (FIG. 23).

Construction of p1-0

The 1.9 kbp segment of pUC1-0 from nucleotide 8715 to 10645 was amplified by PCR using as primers the synthetic oligonucleotides: 5'-CCCCTGCAGCCGGACCGCAC-CACCCCTCGTGACGA-3' (SEQ ID NO: 71) and 5'-CT-TCTAGACTATGAATTCCCTCCGCCCAGC (SEQ ID NO: 61) and the DNA of pUC1-0 as template. The PCR product was end repaired and ligated with plasmid pUC18, which had been linearised by digestion with SmaI and treated with alkaline phosphatase. The ligation mixture was used to transform E. coli DH10B and individual colonies were checked for their plasmid content. The desired plasmid designated p1-0 was identified by restriction analysis and DNA sequencing.

Construction of pX3

The 60 by segment of eryAIII from nucleotide 7006 to 70066 was amplified by PCR using as primers the synthetic oligonucleotides:

(SEQ ID NO: 72)
5'-GGCGGAACGTCTTCCCGGCGGCACCT-3'
and
(SEQ ID NO: 73)
5'-CCCCTGCAGCCAGTACCGCTGGGGCTCGAA-3'
and pEXDB3 (Roberts, G. A., et al. (1993) Eur. J. Biochem. 214:305-311) as template. The PCR product was end-repaired and ligated with plasmid pUC18, which had been linearised by digestion with SmaI and then treated with alkaline phosphatase. The ligation mixture was used to transform E. coli DH10B and individual colonies were checked for their plasmid content. The desired plasmid designated pD3P was identified by restriction analysis and DNA sequencing.

Construction of pT3

The 0.1 kbp EcoRI and PstI restriction fragment from pX3 was ligated with EcoRI and PstI digested pT7-18. The ligation mixture was used to transform E. coli DH10B and individual colonies were checked for their plasmid content. The desired plasmid designated pT3 was identified by restricition analysis.

Construction of pT31-0

The 1.9 kbp PstI and fragment from p1-0 was ligated to PstI digested pT3. The ligation mixture was used to transform E.coli DH10B and individual colonies were checked for their plasmid content. The desired plasmid designated pT31-0 was identified by restriction analysis.

Construction of pD31-0

The 3.3 kbp XmnI restriction fragment from pEXDB3 (Roberts, G. A., et al. (1993) Eur. J. Biochem. 214:305-311) was substituted for the 2.7 kbp XmnI restriction fragment of pT31-0. The desired plasmid pD31-0 was identified by restriction analysis.

Construction of pKETO

Plasmid pD31-0 was digested with BglII and the 11.3 kbp fragment was ligated to pIJ702 which had been linearised by digestion with BglII. The ligation mixture was used to transform E. coli DH10B and individual colonies were check for plasmid content. The desired plasmid designated pKETO was identified by restriction analysis.

EXAMPLE 45

Construction of S. erythraea NRRL2338/pKETO

Approximately 5 μg of plasmid PKETO isolated from E. coli DH10B was used to transform protoplasts of S. erythraea NRRL2338 and stable thiostrepton resistant colonies were isolated. From several such colonies, total DNA was obtained and analysed by Southern hybridisation, to confirm that the plasmid had integrated specifically into the eryAIII gene by homologous recombination. One such clone was selected and designated S. erythraea NRRL2338/pKETO.

(ii) Production of Ketolides Using S. erythraea NRRL2338/pKETO

S. erythraea NRRL2338/pKETO was inoculated into sucrose-succinate medium containing 10 μg/ml thiostrepton and allowed to grow for four days at 30° C. After this time the broth is filtered to remove mycelia, the supernatant adjusted to pH 9.5 and then extracted twice with equal volumes of ethyl acetate. The combined ethyl acetate extracts were evaporated to dryness, the residue taken up in methanol (5 mL) and then analysed by HPLC and electrospray MS. It is found that the major product is the expected 3-ketolide in an approximate yield of 10 mg/L. Analysis of the electrospray mass spectrum shows that the proton adduct for this compound displays a MH+ mass of 558.4, which was confirmed by accurate mass analysis; MH+requires 558.36418 $C_{29}H_{52}O_9N$, observed 558.36427.

EXAMPLE 47

Construction of Plasmid pMO7

Plasmid pMO7 (like plasmid pMO107 also herein described) is an SCP2*-based plasmid containing a PKS gene comprising the ery loading module, the first and second extension modules of the ery PKS and the ery chain-terminating thioesterase, except that the DNA segment encoding the methylmalonyl-CoA:ACP acyltransferase within the first ery extension module has been specifically substituted by the DNA encoding the malonyl-CoA:ACP acyltransferase of module 13 of the rap PKS. It was constructed via several intermediate plasmids as follows (FIG. 24).

Construction of Plasmid pMO1

The approximately 1.3 kbp DNA segment of the eryAI gene of S. erythraea extending from nucleotide 1948 to nucleotide 3273 of erAI (Donadio, S. et al. Science (1991) 252:675-679) was amplified by PCR employing as primers the synthetic oligonucleotides:

```
                                          (SEQ ID NO: 74)
5'-CATGCTCGAGCTCTCCTGGGAAGT-3'
and
                                          (SEQ ID NO: 75)
5'-CAACCCTGGCCAGGGAAGACGAAGACGG-3',
and
``` plasmid pNTEP2 (Example 5) as template. The PCR product was end-repaired and ligated with plasmid pUC18, which had been linearised by digestion with SmaI and then treated with alkaline phosphatase. The ligation mixture was used to transform E. coli TG1 recO and individual colonies were checked for their plasmid content. The desired plasmid pMO1 (3.9 kbp), in which the StuI site bordering the insert is adjacent to the HindIII site in the polylinker, was identified by its restriction pattern.

Construction of Plasmid pMO2

The approximately 0.85 kbp DNA segment of the rapA gene of S. hygroscopicus, extending from nucleotide 1643 to nucleotide 2486 of rapA, was amplified by PCR employing as primers the following oligonucleotides:

```
5'-TTCCCTGGCCAGGGGTCGCAGCGTG-3'(SEQ ID NO: 76)
and
5'-CACCTAGGACCGCGGACCACTCGAC-3'(SEQ ID NO: 77),
and
``` the DNA from the recombinant bacteriophage _-1E (Schwecke, T. et al. Proc. Natl. Acad. Sci. USA (1995) 92:7839-7843) as the template. The PCR product was end-repaired and ligated with plasmid pUC18, which had been linearised by digestion with SmaI and then treated with alkaline phosphatase. The ligation mixture was used to transform E. coli TG1 recO and individual colonies were checked for their plasmid content. The desired plasmid pMO2 (3.5 kbp) was identified by its restriction pattern.

Construction of Plasmid pMO3

The approximately 1.7 kbp DNA segment of the erAI gene of S. erythraea extending from nucleotide 4128 to nucleotide 5928 of eryAI, was amplified by PCR employing as primers the synthetic oligonucleotides:

```
5'-TGGCCAGGGAGTCGGTGCACCTAGGCA-3'(SEQ ID NO: 78)
and
5'-GCCGACAGCGAGTCGACGCCGAGTT-3'(SEQ ID NO: 79)
and plasmid
``` pNTEP2 as template. The PCR product was end-repaired and ligated with plasmid pUC18, which had been linearised by digestion with SmaI and then treated with alkaline phosphatase. The ligation mixture was used to transform E. coli TG1 recO and individual colonies were checked for their plasmid content. The desired plasmid pMO3 (4.4 kbp), in which the BalI and AvrII sites are adjacent to the HindIII site of the polylinker, was identified by its restriction pattern.

Construction of Plasmid pMO4

Plasmid pMO1 was digested with HindIII and BalI and the 1.3 kbp insert was ligated with plasmid pMO3 which had been digested with HindIII and BalI. The ligation mixture was used to transform E. coli TG1 recO and individual colonies were checked for their plasmid content. The desired plasmid pMO4 (5.6 kbp) was identified by its restriction pattern.

Construction of Plasmid pMO5

Plasmid pMO4 was digested with StuI and the 3.0 kbp insert was ligated with plasmid pNTEP2 which had been digested with StuI and the vector purified by gel electrophoresis to remove the 3.8 kbp insert. The ligation mixture was transformed into E. coli TG1 recO and individual colonies were checked for their plasmid content. The desired plasmid pMOS (12.8 kbp) was identified by its restriction pattern.

Construction of Plasmid pMO6

Plasmid pMO2 was digested with BalI and AvrII and the insert was ligated with plasmid pMO5 which had been digested with BalI and AvrII. The ligation mixture was used to transform E. coli TG1 recO and individual colonies were checked for their plasmid content. The desired plasmid pMO6 (13.5 kbp) was identified by its restriction pattern.

Construction of Plasmid pMO7

Plasmid pMO6 was digested with NdeI and XbaI and the insert was ligated with plasmid pRM52 (Example 4) which had been digested with NdeI and XbaI and purified by gel electrophoresis. The ligation mixture was transformed into E. coli TG1 recO and individual colonies were checked for their plasmid content. The desired plasmid pMO7 (also designated pRMAT2) was identified by its restriction pattern.

EXAMPLE 48

Construction of S. coelicolor CH999/pMO7 and Production of TKL Derivatives (i) Construction Plasmid pMO7 which had been isolated from E. coli ET12567 (MacNeil, D. J. et al. Gene (1992) 111:61-68) was transformed into protoplasts of S. coelicolor CH999 and stable thiostrepton resistant colonies were isolated. Individual colonies were checked for their plasmid content and the presence of plasmid pMO7 was confirmed by its restriction pattern.

(ii) Production and Isolation of 4-nor-TKL and (Ac)4-nor-TKL Using *S. coelicolor* CH999/pMO7

*S. coelicolor* CH999/pMO7 was inoculated into YEME medium containing 50_g/ml thiostrepton and allowed to grow for five days at 28-30% C. After this time the broth was filtered to remove mycelia and the pH adjusted to pH 3. The broth was extracted twice with two volumes of ethyl acetate and the combined ethyl acetate extracts were washed with an equal volume of saturated sodium chloride, dried over anhydrous sodium sulphate, and the ethyl acetate was removed under reduced pressure, to give about 200 mg crude product. This was digested with 2 ml of methanol, and mixed with 0.5 g of dry silica gel, and then subjected to flash chromatography on a column of the same material (1 cm×15 cm) The column was eluted with diethyl ether, and fractions of 10 ml each were collected. Fractions 4-8 were pooled, and the diethyl ether was evaporated to leave about 10 mg of oily residue containing the compounds of interest. These were purified further by hplc on an octadecylsilica reverse phase column (10 mm×25 cm) eluted at a flow rate of 2 ml/minute first with an isocratic mixture of water/methanol 75:25 (vol/vol) for five minutes, then with a linear gradient of increasing methanol, reaching water/methanol 55:45 (vol/vol) after 30 minutes. After about 11 minutes, fractions were collected containing, as the minor component, (Ac)4-nor-TKL ($R_1$=Me, $R_2$=H, $R_3$=Me) and after about 18 minutes fractions were collected containing, as the major component, 4-nor-TKL ($R_1$=Me, $R_2$=H, $R_3$=Et)

The $^1$H spectrum of 4-nor-TKL was determined using a Bruker AM-400 NMR spectrometer. Found: H (400 MHz, $CDCl_3$) 4.18 (1H, dtd, 11.8, 6.1, 2.9 Hz, H-5), 3.75 (1H, ddd, 11.0, 10.0, 4.0 Hz, H-3), 2.35 (1H, dq, 10.0, 7.0 Hz, H-2), 2.20 (1H, ddd, 13.3, 4.0, 2.9 Hz, H-4eq), 1.6-1.88 (3H, m, 2xH-6, H-4ax), 1.41 (1H, d, 7.0 Hz, CH3-3'), 1.01 (1H, t, 7.5 Hz, CH3-7) ppm.

The $^{13}$C NMR spectrum of 4-nor-TKL was also determined (100 MHz, $CDCl_3$): 173.3 (C-1), 77.7 (C-5), 70.4 (C-3), 45.1 (C-2), 37.7 (C-4), 28.8 (C-6), 13.5 (C-3'), 9.1 (C-7).

EXAMPLE 49

Construction of Plasmid pMO107 and Production of TKL Derivatives (i) Construction Plasmid pMO6 was digested with NdeI and XbaI and the insert was ligated with plasmid pCJR101 (Example 2) which had been digested with NdeI and XbaI and purified by gel electrophoresis. The ligation mixture was transformed into *E. coli* TG1 recO and individual colonies were checked for their plasmid content. The desired plasmid pMO107 was identified by its restriction pattern.

(ii) Production and Isolation of 4-nor-TKL and (Ac)4-nor-TKL Using *S. erythraea* JC2/pMO107

*S. erythraea* JC2/pMO107 was prepared by standard techniques (c.f. Example 26(i)) and inoculated into sucrose-succinate medium containing 50_g/ml thiostrepton and allowed to grow for three-five days at 28-30% C. After this time the broth was filtered to remove mycelia and the pH adjusted to pH 3. The broth was extracted three times with quarter volumes of ethyl acetate and the combined ethyl acetate extracts were dried over anhydrous sodium sulphate, and the ethyl acetate was removed under reduced pressure, to give about 10 mg/L crude product. This was digested with 2 ml of methanol, and mixed with 0.5 g of dry silica gel, and then subjected to flash chromatography on a column of the same material (1 cm×15 cm) The column was eluted with diethyl ether, and fractions of 10 ml each were collected. Fractions 4-8 were pooled, and the diethyl ether was evaporated to leave about 15 mg of oily residue containing the compounds of interest. These were purified further by hplc on an octadecylsilica reverse phase column (10 mm×25 cm) eluted at a flow rate of 2 ml/minute first with an isocratic mixture of water/methanol 75:25 (vol/vol) for five minutes, then with a linear gradient of increasing methanol, reaching water/methanol 55/45 (vol/vol) after 30 minutes. After about 11 minutes, fractions were collected containing, as the minor component, (Ac)4-nor-TKL and after about 18 minutes fractions were collected containing, as the major component, 4-nor-TKL.

The $^1$H and $^{13}$C spectra of the purified 4-nor-TKL and (Ac)4-nor-TKL were identical with the spectra obtained for authentic material.

EXAMPLE 50

Construction of Plasmid pCJR26

Plasmid pCJR26 is an SCP2* based plasmid containing a PKS gene comprising the ery loading module, the first and second extension modules of the ery PKS and the ery chain-terminating thioesterase, except that the DNA segment encoding the methylmalonyl-CoA:ACP acyltransferase within the first extension module has been specifically substituted by the DNA encoding the malonyl-CoA:ACP acyltransferase of module 2 of the rap PKS. It was constructed as follows (FIG. 25):

Plasmid pMO6 was digested with NdeI and XbaI and the insert was ligated with plasmid pCJR24, which had been digested with NdeI and XbaI and purified by gel electrophoresis. The ligation mixture was transformnd into *E.coli* TG1 recO and individual colonies were checked for their plasmid content. The desired plasmid pCJR26 was identified by its restriction pattern.

EXAMPLE 51

Construction of *S. erythraea* JC2/pCJR26 and Production of TKL Derivatives.

Plasmid pCJR26 was used to transform *S.erythraea* JC2 protoplasts. Thiostrepton resistant colonies were selected on R2T20 medium containing 10 µg/ml of thiostrepton. Several clones were tested for the presence of pCJR26 integrated into the chromosome, by Southern blot hybridisation of their genomic DNA with DIG-labelled DEBS1-TE gene.

A clone with an integrated copy of pCJR26 was grown in SSM medium, containing 5 µg/ml of thiostrepton and allowed to grow for seven days at 28-30° C. After thIs time the broth was filtered to remove mycelia and the pH was adjusted to pH=3. The broth was extracted twice with two volumes of ethyl acetate and the combined ethyl acetate extracts were washed with an equal volume of saturated sodium chloride, dried over anhydrous sodium sulphate, and the ethyl acetate was removed under reduced pressure, to give about 500 mg of crude product. The products were shown to be (Ac)4-nor-TKL and 4-nor-TKL:

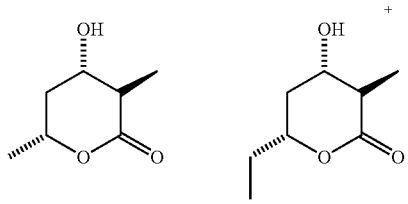

EXAMPLE 52

Construction of *S. erythraea* NRRL 2338/pCJR26 and its Use in production of 14-Membered Macrolides Approximately 5 µg pCJR49 DNA was used to transform *S. erythraea* NRRL2338 protoplasts to give a strain in which the plasmid is integrated into the chromosome. From several colonies, total DNA was obtained and analysed by Southern hybridisation to confirm that the plasmid has integrated in module 2 of EryAI to give a novel macrolide biosynthetic pathway. Further integrations had occurred to give repeated plasmid sequences. *S. erythraea* NRRL 2338/pCJR49 was inoculated into tryptic soy broth containing 5 μg/ml thiostrepton and incubated at 30° C. for three days. 100 ml of this seed culture was used to inoculate 2 litres of sucrose succinate defined medium containing 5 μg/ml thiostrepton in 5×2 litre flasks each containing 500 ml medium with 2 springs to aid dispersion and shaken at 300 rpm. After a further 5 days of growth the cultures were centrifuged and the pH of the supernatant adjusted to pH 9. The supernatant was then extracted three times with an equal volume of ethyl acetate and the solvent removed by evaporation. Products were analysed by HPLC/MS and two macrolides were identified as the erythromycin analogues:

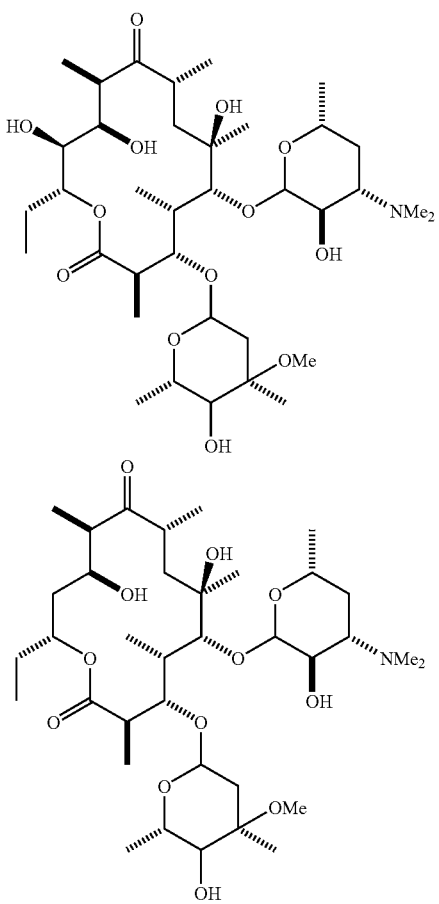

EXAMPLE 53

Construction of Plasmid pC-ATX

Plasmid pC-ATX is an SCP2* based plasmid containing a PKS gene comprising the ery loading module, the first and second extension modules of the ery PKS and the ery chain-terminating thioesterase, except that the DNA segment encoding the methylmalonyl-CoA:ACP acyltransferase within the first extension module has been specifically substituted by the DNA encoding the malonyl-CoA:ACP acyltransferase from a putative type I PKS gene cluster cloned from *Streptomyces cinnamonensis* ATCC 14513 (producer of the polyether polyketide monensin). It was constructed via several intermediate plasmids as follows (FIG. 26).

Isolation of Cosmid pSCIN02.

Genomic library of *Streptomyces cinnamonensis* ATCC 14513 (the monensin producer) was constructed from size fractioned 35-45 kbp Sau3A fragments of chromosomal DNA ligated into BamHI-linearised and alkaline phosphatase-treated cosmid vector pWE15. The ligation mixture was packaged into λ-particles using Gigapack packaging extracts, and transfected into *E.coli* NM1blue. Approximately 600 colonies of the library were grown on the surface of a nylon membrane, lysed, and their DNA was crosslinked to the membrane by UV irradiation. The membrane was subsequently used for the screening procedure. The insert of pMOB comprising the ketosynthase domain from module 2 of DEBS was labelled by random priming in the presence of $^{33}$PaATP and used as a probe for DNA hybridisation. The probe was hybridised for 16h at 68° C. in 4.0×SSC buffer and subsequently washed off for 1 h at 68° C. in 0.8×SSC buffer. Three positive clones were isolated. DNA of the inserts of all three clones was end sequenced from T3 and T7 priming sites present in the vector pWE15. A region homologous to type I ketosynthase and malonyl-CoA:ACP acyltransferase domains was discovered in the DNA sequence from the T7 priming site using clone 2 (named pSCIN02) as a template. Partial DNA sequencing of the malonyl-CoA:ACP acyltransferase domain (named ATX) revealed an unusual sequence motif in the putative substrate recognition part of the domain wich was substantially different from previously described malonate- or methylmalonate-specific CoA:ACP acyltransferases (Haydock, S. F. et al., FEBS (1995) 374:246-248)

Construction of Plasmid pMO38

The approximately 0.9 kbp DNA segment of the ATX domain was amplified by PCR employing as primers the following oligonucleotides:

(SEQ ID NO: 80)
5' CTGGCCAGGGCGCGCAATGGCCGAGCAT 3'
and
(SEQ ID NO: 81)
5' CCCTAGGAGTCGCCGGCAGTCCAGCGCGGCGCCC 3' using the DNA from the cosmid pSCIN02 as the template. The PCR product was end-repaired and ligated with plasmid pUC18, which had been linearised by digestion with SmaI and then treated with alkaline phosphatase. The ligation mixture was used to transform E. coli TG1 recO and individual colonies were checked for their plasmid content. The desired plasmid pMO33 (3.5 kbp) was identified by its restriction pattern.

Construction of Plasmid pMO34

Plasmid pMPO34 is a derivative of pMO6 with a polycloning site inserted after the stop codon of the inserted D1-AT2 gene. Plasmid pMO6 was digested with EcoRI and HindIII and annealed with two oligonucleotides forming the double-stranded region of the polycloning site:

(SEQ ID NO: 82)
5' AATTCATAACTAGTAGGAGGTCTGGCCATCTAGA 3'
and
(SEQ ID NO: 83)
5' TCGAAGATCTACCGGTCTGGAGGATGATCAATAC 3'.

The mixture was ligated and transformed into E. coli TG1 recO. Individual colonies were checked for their plasmid content. The desired plasmid pMO34 (13.5 kbp) was identified by its restriction pattern.

Construction of Plasmid pMO35

Plasmid pMO35 is a derivative of pMO34 containing TKLS-AT2 gene and a translationally coupled crotonyl-CoA-reductase gene from *Streptomyces collinus* (Wallace et al., E. J. Biochem. (1995) 233: 954-962). The crotonyl-CoA-reductase gene was excised from the plasmid pZYB3 (the gift of Prof. K. Reynolds) as an NdeI-BamHI fragment, which was treated with mung bean nuclease to produce blunt ends and ligated into pMO34 previously cut with SpeI and likewise blunt-ended using mung bean nuclease. The ligation mixture was used to transform *E. coli* TG1 recO and individual colonies were checked for their plasmid content. The desired plasmid pMO35 (14.2 kbp), with the correct orientation of the crotonyl-CoA-ketoreductase gene, was identified by its restriction pattern.

Construction of Plasmid pMO36

Plasmid pMO33 was digested with BalI and AvrII and the insert was ligated with plasmid pMO35 which had been digested with BalI and AvrII. The ligation mixture was used to transform *E.coli* TG1 recO and individual colonies were checked fon their plasmid content. The desired plasmid pMO36 (13.5 kbp) was identified by its restriction pattern.

EXAMPLE 54

Construction of Plasmid pC-ATX

Plasmid pMO36 was digested with NdeI and XbaI and the insert was ligated with plasmid pCJR29, which had been digested with NdeI and XbaI and purified by gel electrophoresis. The ligation mixture was transformed into *E.coli* TG1 recO and individual colonies were checked fon their plasmid content. The desired plasmid pC-ATX was identified by its restriction pattern.

EXAMPLE 55

Construction of *S. erythraea* JC2/pC-ATX and Production of TKL Derivatives.

Plasmid pC-ATX was used to transform *S.erythraea* JC2 protoplasts. Thiostrepton resistant colonies were selected on R2T20 medium containing 10 µg/ml of thiostrepton. Several clones were tested for presence of pC-ATX integrated into the chromosome, by Southern blot hybridisation of their genomic DNA with DIG-labelled DNA encoding the DEBS1-TE gene. A clone with an integrated copy of pC-ATX was grown in SSM medium, containing 5 µg/ml of thiostrepton, and allowed to grow for seven days at 28-30'C. After thIs time the broth was filtered to remove mycelia and the pH adjusted to pH=3. The broth was extracted twice with two volumes of ethyl acetate and the combined ethyl acetate extracts were washed with an equal volume of saturated sodium chloride, dried over anhydrous sodium sulphate, and the ethyl acetate was removed under reduced pressure, to give about 500 mg of crude product. The products were characterised by gas chromatography, mass spectrometry and NMR, and were shown to be (2S, 3R, 4S, 5R)-2-methyl-4-ethyl-3,5-dihydroxy-n-hexanoic acid δ-lactone and (2S, 3R, 4S, 5R)-2-methyl-4-ethyl-3,5-dihydroxy-n-heptanoic acid δ-lactone:

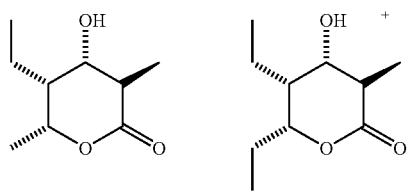

EXAMPLE 56

Construction of *S. erythraea* NRRL 2338/pC-ATX and its Use in Production of 14-Membered Macrolides Approximately 5 µg pC-ATX DNA was used to transform *S. erythraea* NRRL2338 protoplasts to give a strain in which the plasmid is integrated into the chromosome. From several colonies, total DNA was obtained and analysed by Southern hybridisation to confirm that the plasmid has integrated in module 2 of EryAI to give a novel macrolide biosynthetic pathway. Further integrations had occurred to give repeated plasmid sequences. *S. erythraea* NRRL2338/pC-ATX was inoculated into tryptic soy broth containing 5 µg/ml thiostrepton and incubated at 30° C. for three days. 100 ml of this seed culture was used to inoculate 2 litres of sucrose succinate defined medium containing 5 µg/ml thiostrepton in 5×2 litre flasks each containing 500 ml medium with 2 springs to aid dispersion and shaken at 300 rpm. After a further 5 days of growth the cultures were centrifuged and the pH of the supernatant adjusted to pH 9. The supernatant was then extracted three times with an equal volume of ethyl acetate and the solvent removed by evaporation. Products were analysed by HPLC/MS and two macrolide products were identified:

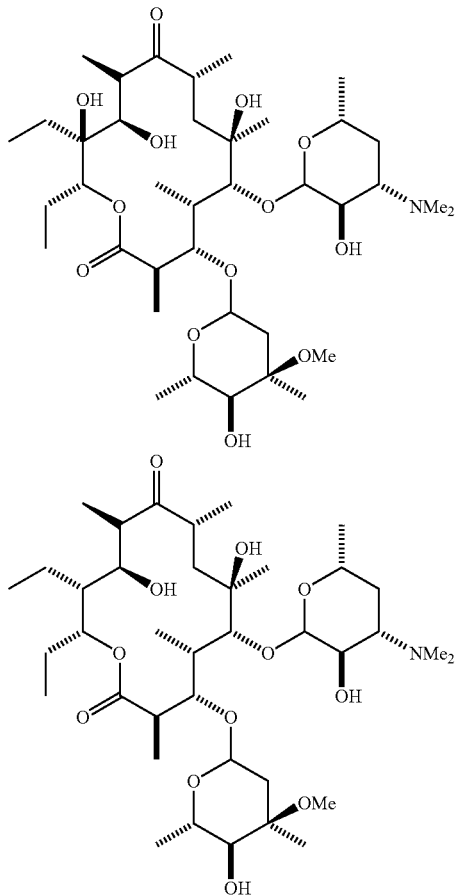

EXAMPLE 57a

Construction of Plasmid pC-AT12

Plasmid pC-AT12 is an SCP2* based plasmid containing a PKS gene comprising the ery loading module, the first and second extension modules of the ery PKS and the ery chain-terminating thioesterase, except that the DNA segment encoding the methylmalonyl-CoA:ACP acyltransferase within the second extension module has been specifically substituted by the DNA encoding the malonyl-CoA:ACP acyltransferase of module 2 of the rap PKS. It was constructed via several intermediate plasmids as follows (FIG. 27).

Construction of Plasmid pMO25.

The approximately 1.0 kbp DNA segment of the eryAI gene of *S. erythraea* extending from nucleotide 6696 to nucleotide 7707 of eryAI (Donadio. S. et al., Science (1991) 252, 675-679) was amplified by PCR employing as primers synthetic oligonucleotides:

```
5' GGCGGGTCCGGAGGTGTTCACCGAGTT 3' (SEQ ID NO: 84)
and
5' ACCTTGGCCAGGGAAGACGAACACTGA 3' (SEQ ID NO: 85),
``` and plasmid pNTEp2 as a template. The PCR product was end-repaired and ligated with plasmid pUC18, which had been linearised by digestion with SmaI and then treated with alkaline phosphatase. The ligation mixture was used to transform E. coli TG1 recO and individual colonies were checked for their plasmid content. The desired plasmid pMO25 (3.6 kbp), in which the StuI site bordering the insert is adjacent to the HindIII site in the polylinker, was identified by its restriction pattern.

Construction of Plasmid pMO26

The approximately 0.6 kbp DNA segment of the eryAI gene of *S. erythraea* extending from nucleotlde 8660 to nucleotide 9258 of eryAI, was amplified by PCR employing as primers the synthetic oligonucleotides:

```
                                        (SEQ ID NO: 86)
5' TCCTAGGCCGGGCCGGACTGGTCGACCTGCCGGGTT 3'
and
                                        (SEQ ID NO: 87)
5' AAACACCGCGACCTGGTCCTCCGAGC 3',
and plasmid
``` pNTEP2 as template. The PCR product was end-repaired and ligated with plasmid pUC18, which had been linearised by digestion with SmaI and then treated with alkaline phosphatase. The ligation mixture was used to transform E. coli TG1 recO and individual colonies were checked for their plasmid content. The desired plasmid pMO26 (3.2 kbp), in which the AvrII site is adjacent to the HindIII site of the polylinker, was identified by its restriction pattern.

Construction of Plasmid pMO27.

Plasmid pMO25 was digested with EcoRI and BalI and the 1.0 kbp insert was ligated with plasmid pMO2 which had been digested with EcoRI and BalI. The ligation mixture was used to transform *E. coli* TG1 recO and individual colonies were checked for their plasmid content. The desired plasmid pMO27 (4.4 kbp) was identified by its restriction pattern.

Construction of Plasmid pMO32.

Plasmid pMO26 was digested with AvrII and HindIII and the 0.6 kbp insert was ligated with plasmid pMO27 which had been digested with AvrII and HindIII. The ligation mixture was used to transform *E. coli* TG1 recO and individual colonies were checked for their plasmid content. The desired plasmid pMO32 (5.1 kbp) was identified by its restriction pattern.

Construction of Plasmid pMO33.

Plasmid pMO32 was digested with BspEI and SexAI and the 2.7 kbp insert was ligated with plasmid pNTEP2 which had been digested with the same two enzymes and purified by gel electrophoresis to remove the 2.8 kbp insert. The ligation mixture was transformed into *E.coli* TG1 recO and individual colonies were checked for their plasmid content. The plasmid pMO33 (12.8 kbp) was identified by its restriction pattern.

EXAMPLE 57b

Construction of Plasmid pC-AT12.

Plasmid pMO33 was digested with NdeI and XbaI and the insert was ligated with plasmid pCJR29, which had been digested with NdeI and XbaI and purified by gel electrophoresis. The ligation mixture was transformnd into *E.coli* TG1 rec0 and individual colonies were checked for their plasmid content. The desired plasmid pC-AT12 was identified by its restriction pattern.

EXAMPLE 58a

Construction of *S.erythraea* JC2/pC-AT12 and Production of TKL Derivatives.

Plasmid pC-AT12 was used to transform *S.erythraea* JC2 protoplasts. Thiostrepton resistant colonies were selected on R2T20 medium containing 10 µg/ml of thiostrepton. Several clones were tested for the presence of pC-AT12 integrated into the chromosome, by Southern blot hybridisation of their genomic DNA with DIG-labelled DNA encoding the DEBS1-TE gene. A clone with an integrated copy of pC-AT12 was grown in SSM medium, containing 5 µg/ml of thiostrepton and allowed to grow for seven days at 28-30° C. After thIs time the broth was filtered to remove mycelia and the pH adjusted to pH=3. The broth was extracted twice with two volumes of ethyl acetate and the combined ethyl acetate extracts were washed with an equal volume of saturated sodium chloride, dried over anhydrous sodium sulphate, and the ethyl acetate wass removed under reduced pressure, to give about 500 mg of crude product. The products were shown to be (3R, 4S, 5R)-4-methyl-3,5-dihydroxy-n-hexanoic acid δ-lactone and (3R, 4S, 5R)-4-methyl-3,5-dihydroxy-n-heptanoic acid b-lactone:

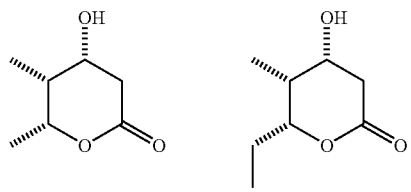

EXAMPLE 58b

Construction of *S. erythraea* NRRL 2338/pC-AT12 and its Use in Production of 14-Membered Macrolides Approximately 5 µg pC-AT12 DNA was used to transform *S. erythraea* NRRL2338 protoplasts to give a strain in which the plasmid is integrated into the chromosome. From several colonies, total DNA was obtained and analysed by Southern hybridisation to confirm that the plasmid has integrated 3' of module 2 of EryAI to give a novel macrolide biosynthetic pathway. Further integrations had occurred to give repeated plasmid sequences. S. erythraea NRRL2338/pC-AT12 was inoculated into tryptic soy broth containing 5 μg/ml thiostrepton and incubated at 30° C. for three days. 100 ml of this seed culture was used to inoculate 2 litres of sucrose succinate defined medium containing 5 μg/ml thiostrepton in 5×2 litre flasks each containing 500 ml medium with 2 springs to aid dispersion and shaken at 300 rpm. After a further 5 days of growth the cultures were centrifuged and the pH of the supernatant adjusted to pH 9. The supernatant was then extracted three times with an equal volume of ethyl acetate and the solvent removed by evaporation. Products were analysed by HPLC/MS and two macrolide products were identified:

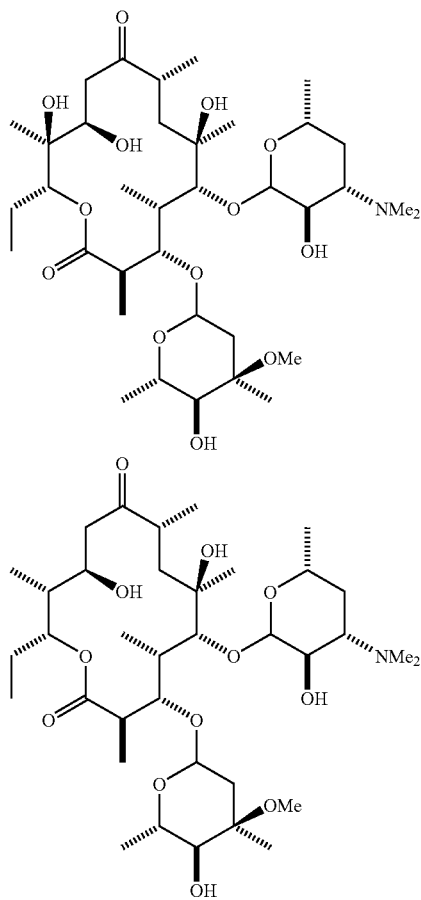

EXAMPLE 59

Construction of Plasmid pCJR49 pCJR49 is a pCJR24-based plasmid containing a mutant DEBS1-TE gene which has no ketoreductase in module 2, and the AT domain in module 2 has been replaced by RAPS AT2 in order to incorporate a malonyl extender instead of a methylmalonyl extender in the second module (FIG. 28).

pMO32 was digested with BspE I and SexA I and the fragment containing the AT from RAP module 2 was cloned into pUC1-0 which had been previously digested with BspE I and SexA I, to yield the plasmid pCJR43.

pCJR43 was digested with Nde I and Xba I and the fragment containing the mutant DEBS1-TE gene was cloned into pCJR24 which had previously been digested with Nde I and Xba I, to yield plasmid pCJR49. pCJR49 was confirmed by restriction enzyme mapping.

EXAMPLE 60

Construction of S. erythraea JC2/pCJR49 and Production of TKL Derivatives i) Approximately 5 μg pCJR49 DNA was used to transform S. erythraea JC2 protoplasts to give a strain in which the plasmid is integrated into the chromosome. From several colonies total DNA is obtained and analysed by Southern hybridisation to confirm that the plasmid has integrated into the eryTE. S. erythraea JC2/pCJR49 is inoculated into tryptic soy broth containing 5 μg/ml thiostrepton and incubated at 30° C. for three days. 100 ml of this seed culture was used to inoculate 2 litres of sucrose succinate defined medium containing 5 μg/ml thiostrepton in 5×2 litre flasks each containing 500 ml medium with 2 springs to aid dispersion and shaken at 300 rpm. After a further 5 days of growth the cultures were centrifuged and the pH of the supernatant was adjusted to pH 3. The supernatant was then extracted three times with an equal volume of ethyl acetate and the solvent removed by evaporation. Products were dissolved in methanol and analysed by GCMS on a Finnegan-MAT GCQ System. This analysis indicated that by comparison to synthetic standards two new lactones were present. These products were (4S,5R)-4-methyl-3-keto-5-hydroxyhexanoic acid δ lactone and (4S,5R)-4-methyl-3-keto-5-hydroxyheptanoic acid δ lactone:

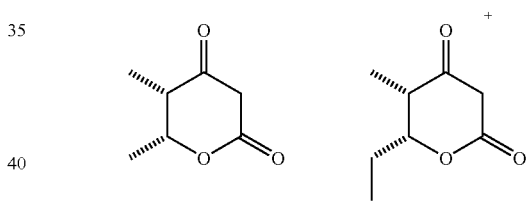

EXAMPLE 61

Construction of S. erythraea NRRL 2338/pCJR49 and its Use for Production of 14-Membered Macrolides 5 μg pCJR49 DNA was used to transform S. erythraea NRRL2338 protoplasts to give a strain in which the plasmid is integrated into the chromosome. From several colonies total DNA is obtained and analysed by Southern hybridisation to confirm that the plasmid has integrated in module 2 of EryAI to give a novel macrolide biosynthetic pathway. Further integrations had occurred to give repeated plasmid sequences. S. erythraea/pCJR49 is inoculated into tryptic soy broth containing 5 μg/ml thiostrepton and incubated at 30° C. for three days. 100 ml of this seed culture was used to inoculate 2 litres of sucrose succinate defined medium containing 5 μg/ml thiostrepton in 5×2 litre flasks each containing 500 ml medium with 2 springs to aid dispersion and shaken at 300 rpm. After a further 5 days of growth the cultures were centrifuged and the pH of the supernatant adjusted to pH 9. The supernatant was then extracted three times with and equal volume of ethyl acetate and the solvent removed by evaporation. Products were analysed by HPLC/MS and two macrolides were identified:

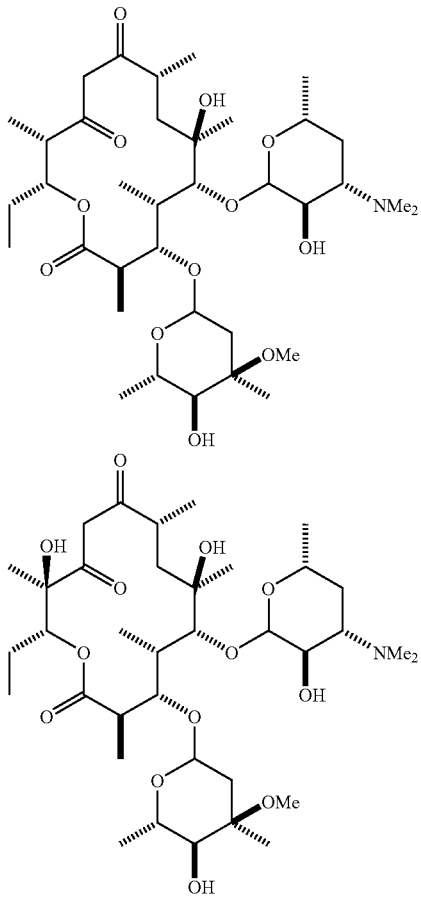

EXAMPLE 62

Construction of Plasmid (FIG. 29A-F)

Plasmid pCART11 is a pRM52-based plasmid containing a PKS gene comprising the avermectin loading module, modules 5 and 6 of the ery PKS, and the ery chain-terminating thioesterase. It was constructed via several intermediate plasmids as follows.

Construction of Plasmid pCAR1

Plasmid pARLD was digested with BamHI and BglII and 1.70 kbp insert was ligated with plasmid pEXD3 which had been digested with BglII. The ligation mixture was used to transform E.Coli TG1 recO and individual colonies were checked for their plasmid content. The desired plasmid pCAR1 was identified by its restriction pattern.

Construction of Plasmid pCAR5

The 250 by DNA segment of the eryAIII gene of S. erythraea extending from nucleotide 4807 to nucleotide 5052 of eryAIII, was amplified by PCR employing as primers the synthetic oligonucleotides:

(SEQ ID NO: 88)
5' TTTGCTAGCGATCGTCGGCATGGCGTGCCGGTT 3'

(SEQ ID NO: 89)
5' CCCACGAGATCTCCAGCATGATCC 3'.

The plasmid pEXD3 was used as a template. The PCR product was end-repaired and ligated with pUC18, which had been linearised by digestion with SmaI and then treated with alkaline phosphatase. The ligation mixture was used to transform E. Coli TG1 recO and individual colonies were checked for their plasmid content. The desired plasmid pCAR5 in which the NheI site is adjacent to the EcoRI site of the polylinker, was identified by its restriction pattern and sequence analysis.

Construction of Plasmid pCAR2

Plasmid pCAR5 was digested with NheI and BglII and 250 bp insert was ligated with plasmid pCAR1 which had been digested with NheI and BglII. The ligation mixture was used to transform E.Coli TG1 recO and individual colonies were checked for their plasmid content. The desired plasmid pCAR2 was identified by its restriction pattern.

Construction of Plasmid pCAR21

Plasmid pARTr was digested with XbaI and the 1.20 kbp tetracyclin gene was ligated with plasmid pCAR2 which had been digested with XbaI. The ligation mixture was used to transform E.Coli TG1 recO and individual colonies were checked for their plasmid content. The desired plasmid pCAR21 was identified by its restriction pattern Construction of Plasmid pCART3

Plasmid pCAR21was digested with PacI and PstI and 13.0 kbp insert was ligated with plasmid pRM52 which had been digested with PacI and NsiI. The ligation mixture was used to transform E.Coli TG1 recO and individual colonies were checked for their plasmid content. The desired plasmid pCART3 was identified by its restriction pattern Construction of Plasmid pIGlet Plasmid pARTr was digested with XbaI and the 1.20 kbp tetracyclin gene was ligated with plasmid pIGI which had been digested with XbaI. The ligation mixture was used to transform E.Coli TG1 recO and individual colonies were checked for their plasmid content. The desired plasmid pIGlet was identified by its restriction pattern.

Construction of Plasmid pCART11

Plasmid pCAR21was digested with NheI and 12.0 kbp insert was ligated with plasmid pIGlet which had been digested NheI. The ligation mixture was used to transform E.Coli TG1 recO and individual colonies, resistent to tetracyclin activity were checked for their plasmid content. The desired plasmid pCART11 was identified by its restriction pattern.

EXAMPLE 63

Construction of S. erythraea NRRL2338/pCART11 and its Use for Production of Triketide Lactones Approximately 5-10 μg of pCART11, isolated from TG1 recO was transformed into S. erythraea NRRL2338 and stable thiostrepton resistant colonies were isolated.

A 5 ml fermentation of S.erythraea NRRL233B/pCART11 was carried out in TSB medium and after two days at 30° C., the mycelium was used to inoculate 50 ml of sucrose-succinate medium containing thiostrepton (50 μg/ml). After growth at 30° C. for four days, the whole broth was extracted twice with an equal volume of ethyl acetate. The solvent was concentrated and the mixture analysed on the GC-MS. The following compounds were identified.

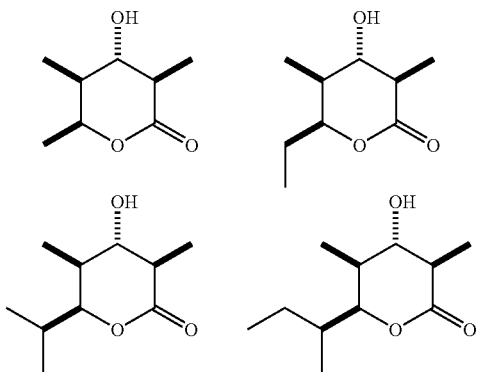

EXAMPLE 64

Construction of Plasmid pARE24

Plasmid pARE24 is a pCJR24-based plasmid containing a PKS gene comprising the ery loading module, modules 5 and 6 of the ery PKS, and the ery chain-terminating thioesterase. It was constructed as follows (FIG. 30).

Construction of Plasmid pARE24

Plasmid pCAR21 was digested with PacI and XbaI and the 13.0 kbp insert was ligated with plasmid pCJR24 which had been digested with Pacd and XbaI. The ligation mixture was used to transform *E.Coli* TG1 recO and individual colonies were checked for their plasmid content. The desired plasmid pARE24 was identified by its restriction pattern.

Construction of *S.erythraea* NRRL2338/pARE24 and its Use for Production of Triketide Lactones Approximately 5-10 μg of pARE24, isolated from TG1 recO was transformed into *S. erythraea* NRRL2338 and stable thiostrepton resistant colonies were isolated.

A 5 ml fermentation of *S.erythraea* NRRL2338/pARE24 was carried out in TSB medium and after two days at 30° C., the mycelium was used to inoculate 50 ml of sucrose-succinate medium containing thiostrepton (50 μg/ml). After growth at 30° C. for four days, the whole broth was extracted twice with an equal volume of ethyl acetate. The solvent was concentrated and the mixture analysed on the GC-MS. The following compounds were identified.

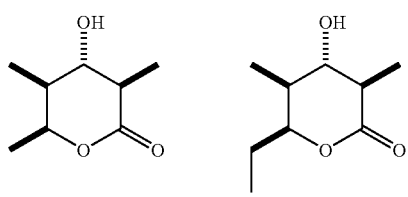

EXAMPLE 65

Construction of Plasmid (FIG. 30) pARA24

Plasmid pARA24 is a pCJR24-based plasmid containing a PKS gene comprising the avermectin loading module, modules 5 and 6 of the ery PKS, and the ery chain-terminating thioesterase. It was constructed as follows.

Construction of Plasmid pARA24

Plasmid pIG1 was digested with PacI and NheI and 1.70 kbp insert was ligated with plasmid pARE24 which had been digested with PacI and NheI. The ligation mixture was used to transform *E.Coli* TG1 recO and individual colonies were checked for their plasmid content. The desired plasmid pARA24 was identified by its restriction pattern.

EXAMPLE 66

Construction of *S.erythraea* NRRL2338/pARA24

Approximately 5-10 μg of pARA24, isolated from TG1 recO was transformed into *S. erythraea* NRRL2338 and stable thiostrepton resistant colonies were isolated.

A 5 ml fermentation of *S.erythraea* NRRL2338/pARA24 was carried out in TSB medium and after two days at 30° C., the mycelium was used to inoculate 50 ml of sucrose-succinate medium containing thiostrepton (50 μg/ml). After growth at 30° C. for four days, the whole broth was extracted twice with an equal volume of ethyl acetate. The solvent was concentrated and the mixture analysed on the GC-MS. The following compounds were identified.

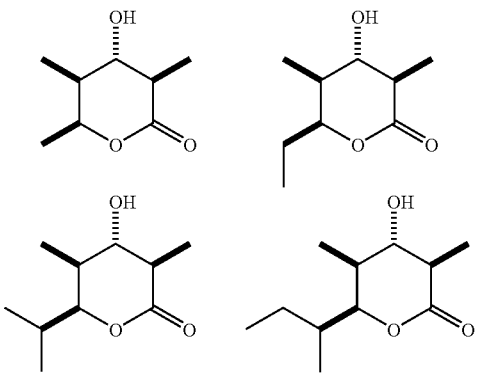

EXAMPLE 67

Construction of Plasmid pARL3

The plasmid pARL3 is a pCJR24-based plasmid containing a PKS gene comprising the ery loading module, modules 5 and 6 of the ery PKS, and the ery thioesterase. The junction between the loading module and the KS5 domain is made at the very N-terminal edge of KS5. It was constructed via several intermediate plasmids as follows (FIG. 31):

Construction of Plasmid pARL1

The 450 by DNA segment of the erAI gene of *S. erythraea* extending from nucleotide 1 to nucleotide 10631 of eryAI, was amplified by PCR employing as primers the synthetic oligonucleotides: (bases in bold letters denote the restriction enzyme sites).

```
    SphI
5' GGCGGCATGCGGCGGTTCCT 3'         (SEQ ID NO: 90)

NheI
5' AAGCTAGCGGTTCGCCGGGCGCCGCTTCGT  (SEQ ID NO: 91)

HpaI
TGGTCCGCGCGCGGGTTAAC 3'
```

The plasmid pARE24 was used as a template. The PCR product was end-repaired and ligated with pUC18, which had been linearised by digestion with SmaI and then treated with alkaline phosphatase. The ligation mixture was used to transform *E.coli* TG1 recO and individual colonies were checked for their plasmid content. The desired plasmid pARL1, in which the NheI site is adjacent to the EcoRI site of the polylinker, was identified by its restriction pattern and sequence analysis.

Construction of Plasmid pARL2

Plasmid pARL1 was digested with NheI and SphI and the 450 bp insert was ligated with plasmid pARE24 which had been digested with NheI and SphI. The ligation mixture was used to transform *E.coli* TG1 recO and individual colonies were checked for their plasmid content. The desired plasmid pARL2 was identified by its restriction pattern.

Construction of Plasmid pARL3

The following complementary synthetic oligonucleotides were synthesised so as when annealed, they would have the necessary pattern at the 5' and 3' ends that is produced by the action of HpaI and NheI respectively

```
                                               (SEQ ID NO: 92)
5'AACCCGCGCGCGGACCAACGAAGCGGCGCCCGGCGAACCG 3'

(SEQ ID NO: 93)
5'CTAGCGGTTCGCCGGGCGCCGCTTCGTTGGTCCGCGCGCGGGTT 3'.
```

The synthetic oligonucleotides were annealed to give double-stranded DNA which was ligated with plasmid pARL2 which had been digested with NheI and HpaI. The ligation mixture was used to transform *E. coli* TG1 recO and individual colonies were checked for their plasmid content. The desired plasmid pARL3 was identified by its restriction pattern.

EXAMPLE 68

Construction of *S.erythraea* JC2-pARL3 and its Use for Production of Triketide Lactones Approximately 5-10 µg of pARL3, isolated from TG1 recO was transformed into *S. erythraea* JC2 and stable thiostrepton resistant colonies were isolated. A 5 ml fermentation of JC2-pARL3 was carried out in TSB medium and after two days at 30° C., the mycelium was used to inoculate 50 ml of sucrose-succinate medium containing thiostrepton (50 µg/ml). After growth at 30° C. for four days, the whole broth was extracted twice with an equal volume of ethyl acetate. The solvent was concentrated and the mixture analysed on the GC-MS. The following compounds were identified:

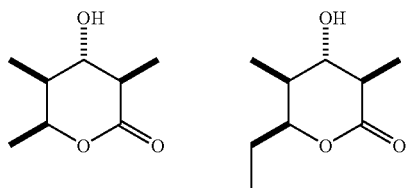

EXAMPLE 69

Construction of *S. erythraea* ERMD1, carrying a hybrid PKS gene in which the avr loading didomain is substituted for the ery loading didomain of *S. erythraea* NRRL 2338

(i) Construction of Plasmid pAVLD

Plasmid pCRabc (Example 9) was linearised with BamHI and ligated to pIJ702 previously digested with BglII. The mixture contained the desired plasmid pAVLD (FIG. 32). The ligation mixture was transformed into *E.coli* TG1 recO and individual colonies were checked for their plasmid content. The desired plasmid pAVLD was identified by its restriction pattern (FIG. 32).

(ii) Construction of *S.erythraea* ERM D1

Approximately 5-10 µg of pAVLD, isolated from *E. coli* TG1recO(pAVLD) was transformed into *S. erythraea* NRRL2338 and stable thiostrepton resistant colonies were isolated. One of these colonies was selected and total DNA was digested with PstI and analysed by Southern hybridisation employing as a probe the insert from plasmid pCRc which contains the fragment of the ery AI gene encoding the ketosynthase domain KS1. The analysis showed positively-hybridizing PstI fragments of 8.5 kbp, 4.8 kbp and 33 kbp, indicating the presence of two tandemly integrated copies of pAVLD (FIG. 33).

EXAMPLE 70

Isolation of Erythromycins Altered at C-13

A 50 ml fermentation of *S. erythraea* ERMD1 was carried out on tap water medium and after 4 days at 30% C the mycelium was harvested and used to inoculate 1.5 litres of sucrose-succinate medium containing thiostrepton (50 g/ml).

After growth at 30% C for 4 days, the whole broth was extracted twice with an equal volume of ethyl acetate.

The combined extracts were concentrated under reduced pressure and subjected twice to preparative thin layer chromatography on silica plates (20×20 cm) eluted with chloroform/methanol/0.88 ammonia 8:2:0.01 (by vol). The products were separated by hplc on a PhaseSep C18 base-deactivated reverse phase column S5odS (octadecylsilica) 6(4.6 mm×250 mm), eluted with methanol/0.5% ammonium acetate (70:30 (vol/vol), at 1 ml.min. Fractions were collected between 7 and 11 minutes from three separate injections, and the pooled fractions were re-injected in ten separate injections. The order of elution from the column was: erythromycin B analogues, followed by erythromycin D analogues and erythromycin A analogues. B and D analogues emerged after 8-10 minutes, erythromycin A analogue 3-4 minutes later. The analogues containing a C-4 (isobutyryl) starter unit are eluted earlier, with the analogues with C-5 (2-methylbutyryl) starter unit emerging several minutes later, although the C-4 late (eryA analogue) and the early C-5 (erythromycins B and D analogue) overlap. High resolution MS gave results for C-4 eryA, eryB and eryD analogues, and for C-5 eryA and eryB analogues, which correspond closely to those calculated:

| Analogue | Calc'd Mass | Measured Mass |
|---|---|---|
| C5-eryA | 762.5004 | 762.5021 |
| C4-eryA | 748.4847 | 748.4820 |
| C5-eryB | 746.4898 | 748.5077 |
| C4-eryB | 732.4898 | 732.4933 |

In these experiments natural erythromycins were present only in low or undetectable amounts, and there were no detectable amounts of eryC analogues. The overall concentration ratio of C-4/C-5 compounds in the fermentation broth, as assessed by ESMS of ethyl acetate extracts of broths, was between 4:1 and 6:1 in favour of C-4 compounds. The ratio of A:B:D analogues is variable, about 15:60:25, but with an increasing proportion of A analogues as the fermentation proceeds. The total yield of erythromycins is about 400 µg/litre.

EXAMPLE 71

Construction and Use of *S. erythraea* NRRL2338/pRMTE
(i) Construction
Approximately 5 µg of plasmid pRMTE (Example 6) isolated from *E. coli* TGI recO (pRMTE) was transformed into protoplasts of *S. erythraea* NRRL2338 and stable thiostrepton resistant colonies were isolated. One of these was selected and designated *S. erythraea* NRRL2338/pRMTE.
(ii) Enhanced Production of Erythromycin A and Erythronolides Using *S. erythraea* NRRL2338/pRMTE
*S. erythraea* NRRL2338/pRMTE was grown in sucrose and succinate medium containing 50 µg/ml thiostrepton at 28-30% C. After 3 days the whole broth was extracted twice with an equal volume of ethyl acetate, the combined ethyl acetate extracts were washed with saturated sodium chloride solution, dried over anhydrous sodium sulphate, and concentrated under reduced pressure.

Examination of the extract by thin layer chromatography on silica plates eluted with isopropyl ether:methanol:ammonium hydroxide 75:35:1 (by volume) showed the presence of several components. Electrospray mass spectrometry of the extracts revealed the presence of a mixture of erythromycin A, erythronolide B (EB) and 6-deoxyerythronolide B (6-DEB), together with minor amounts of (Ac)-6-DEB as its sodium adduct, (Ac)-EB as its Na adduct (411.1), and EB as its Na adduct (424.1), and also TKL (m/e 159.1). The yield of erythromycin A plus erythronolide B was about 500 mg/L of medium, compared to about 50 mg/L produced by *S. erythraea* NRRL2338 fermented under identical conditions. Cells of *S. erythraea* NRRL2338/pRMTE harvested from the fermentation broth after 3 days were disrupted and their protein content was examined by sodium dodecyl sulphate/polyacrylamide gel electrophoresis. Three high molecular weight bands, corresponding to the erythromycin PKS multienzyme subunits DESS1, DEBS2 and DEBS3 were observed, approximately ten times more intense than the same protein band seen from cell extracts of *S. erythraea* NRRL2338 prepared by the same procedure (Caffrey, P. et al. FEBS Letters (1992) 304:225-228).

An identical fermentation of *S. erythraea* NRRL2338/pRMTE was carried out except that the medium was supplemented with 5 mM potassium propionate. After three days the broth was extracted with ethyl acetate as before, and the combined ethyl acetate extracts were dried over anhydrous sodium sulphate, and concentrated. Preparative TLC using the system isopropyl ether:methanol:ammonium hydroxide 75:35:1 (by volume) separated two major components. Analytical TLC showed that the faster running component (Rf 0.8) has the same mobility as authentic 6-DEB; and the slower migrating material was an approximately equal mixture of a component of Rf 0.63, co-migrating with an authentic sample of TKL; and a component of Rf 0.60, with the same mobility as an authentic sample of EB.

Electrospray mass spectrometry (ESMS) on a VG BioQ mass spectrometer operated in positive ion mode showed that the component of Rf 0.75 had m/e 387.4, as required for 6-DEB. ESMS of the mixture of the components with Rf values 0.60 and 0.63 confirmed the presence of TKL and EB.

EXAMPLE 72

Construction and Use of *S. erythraea* TER43/pRMTE
(i) Construction
Approximately 5 µg of plasmid pRMTE was transformed into protoplasts of *S. erythraea* TER43 (Cortes, J. et al., Science (1995) 268:1487-1489) and stable thiostrepton resistant colonies were isolated. One of these was selected and designated *S. erythraea* TER43/pRMTE.
(ii) Enhanced Production of TKL Using *S. erythraea* TER43/pRMTE
*S. erythraea* TER43/pRMTE was inoculated into IL sucrose-succinate medium and allowed to grow for 3 days at 28-30% C. After 3 days, the broth was extracted twice with an equal volume of ethyl acetate, and the combined ethyl acetate extracts were dried over anhydrous sodium sulphate and concentrated. Analysis of the extract by electrospray mass spectrometry (operated in the positive ion mode) showed the presence of TKL (m/e 173.1) and of (Ac)-TKL (m/e 159.1). The combined yield of triketide lactones was 100 mg/L, compared with 10 mg/L obtained by fermentation of *S. erythraea* TER43 under identical conditions. Cells of *S. erythraea* TER43/pRMTE, harvested from the fermentation broth after 3 days, were disrupted and their protein content was examined by sodium dodecyl sulphate/polyacrylamide gel electrophoresis. A high molecular weight band, corresponding to the erythromycin PKS subunit DEBS1 with the attached thioesterase domain (Cortes, J. et al. Science (1995) 268: 1487-1489) was observed, approximately ten times more intense than the same protein band seen from cell extracts of *S. erythraea* prepared by the same procedure.

EXAMPLE 73

Construction and Use of *S. erythraea* NRRL2338/pCJRTE (pCJR30)
(i) Construction
Approximately □5 g of plasmid pCJRTE (pCJR30) is transformed into protoplasts of *S. erythraea* NRRL2338 and stable thiostrepton resistant colonies are isolated.

From several such colonies, total DNA is obtained and analysed by Southern hybridisation, to confirm that the plasmid has integrated specifically into the eryA genes by homologous recombination, so as to place the resident eryA genes under the control of the actI promoter derived from plasmid pCJRTE (pCJR30), while the DEBS1-TE gene borne by the incoming plasmid is placed by the integration event under the control of the chromosomal eryA promoter.
(ii) Enhanced Production of Erythromycins and Their Precursors Using *S. erythraea* NRRL2338/pCJRTE (pCJR30).
*S. erythraea* NRRL2338/pCJRTE (pCJR30) is inoculated into sucrose-succinate medium containing 50 µg/ml thiostrepton and allowed to grow for four days at 30% C. After this time the broth is filtered to remove mycelia and then extracted twice with an equal volume of ethyl acetate.

The combined ethyl acetate extracts are analysed by mass spectrometry and it is found that the mixture contains erythromycin A, accompanied by 6-DEB, (Ac)-DEB, TKL and (Ac)-TKL, in total amounts 100 mg/L, or 5 times the total amount of erythromycins and precursors of erythromycins that are obtained using *S. erythraea* NRRL2338 under the same conditions.

EXAMPLE 74

Construction and Use of *S. erythraea* JC2/pCJRTE (pCJR30)
(ii) Construction
Approximately 5_g of plasmid pCJRTE (pCJR30) is transformed into protoplasts of *S. erythraea* JC2 and stable thiostrepton resistant colonies are isolated. From several such colonies, total DNA is obtained and analysed by Southern hybridisation, to confirm that the plasmid has integrated specifically into the portion of the eryAIII gene that encodes the C-terminal thioesterase/cyclase, by homologous recombination.

(ii) Enhanced Production of Triketide Lactones Using *S. erythraea* JC2/pCJRTE (pCJR30)

*S. erythraea* JC2/pCJRTE (pCJR30) is inoculated into sucrose-succinate medium containing 50_g/ml thiostrepton and allowed to grow for four days at 30% C. After this time the broth is filtered to remove mycelia and then extracted twice with an equal volume of ethyl acetate. The combined ethyl acetate extracts are analysed by mass spectrometry and NMR and it is found that the major product is TKL, and the minor product (Ac)TKL, in total yields (100 mg/L) 10 fold greater than obtained using *S. erythraea* TER43.

EXAMPLE 75

Construction and Use of *S. erythraea* NRRL2338/pIG1

(i) Construction

Approximately 5_g of plasmid pIG1 is transformed into protoplasts of *S. erythraea* NRRL2338 and stable thiostrepton resistant colonies are isolated. From several such colonies, total DNA is obtained and analysed by Southern hybridisation, to confirm that the plasmid has integrated specifically into the portion of the eryAIII gene that encodes the C-terminal thioesterase/cyclase, by homologous recombination.

(ii) Production of 14-Membered Lactones Using *S. erythraea* NRRL/pIG1

*S. erythraea* NRRL/pIG1 is inoculated into tap water medium containing 50_g/ml thiostrepton and allowed to grow for four days at 30% C. After this 20 ml of the mycelium is used to seed 500 ml of sucrose-succinate medium containing 50 µg/ml thiostrepton, in a 2 L flask with a single spring to reduce clumping, shaken at 280 rpm. After between 3.5 and 6 days, the broth is filtered to remove mycelia and then extracted three times with a quarter volume of ethyl acetate. The combined ethyl acetate extracts are dried over anhydrous sodium sulphate and solvent removed by evaporation. Analysis of the product mixture using GC and electrospray MS revealed that of a total of 5-6 mg/L of 14-membered macrolide products, the major component was (s-pent)-erythromycin D (about 1.5 mg/L), with other components present being (s-pent)-erythromycin B and (s-pent)-erythromycin A; (i-but)-erythromycins A, B and D; and small amounts of natural erythromycins A, B and D. The extracts also contained significant amounts (11 mg/l) of TKL's: (s-pent)-TKL (5mg/l), (i-but)-TKL and TKL. (NB s-pent and i-but indicate 1-methylpropyl and isopropyl side-chains, respectively, corresponding to the use of s-2-methylbutyl and i-butanoyl starter substrates.)

EXAMPLE 76

Determination of Antibiotic Activity of Novel Erythromycin A Analogues

A 3 ml overnight culture of *Bacillus subtilis* ATCC 6633 was grown at 30% C in nutrient broth (Difco). 200 ml of nutrient 1.5% agar (difco) at 46% C was seeded with 1 ml of the *B.subtilis* culture and poured immediately into petri dishes (25 ml/plate). After drying the plates in a laminar flow hood for 15 minutes, wells (0.4 mm in diameter) were cut using a cork borer and 20 microlitres of the test compound as a solution in ethanol (5-10 mg/L) was added to each well. The plates were kept at 4% C for 5-7 hours to allow the compound to diffuse, and the plates were then incubated overnight at 30% C. Clear zones of growth inhibition were seen with both (i-but)- and (s-pent)-erythromycin A.

Although the present invention is illustrated by the examples listed above, they should not be regarded as limiting the scope of the invention. The above descriptions illustrate first, how a specific promoter for a Type II PKS gene set, coupled to its specific cognate activator gene, contrary to expectation, may be used to achieve controlled and enhanced expression of Type 1 PKS genes in a heterologous host. Examples of these hosts that are given are *S. erythraea* and *S. avermitilis*, but it will be evident to those skilled in the art that alternative hosts, drawn from a wide range of actinomycetes, will equally well serve as expression hosts. Similarly, although the acti promoter and its cognate activator gene actII-orf4 have been used in these Examples, it will be evident to those skilled in the art that other Type II PKS promoter/activator gene combinations are well-known and characterised which will be equally efficacious in directing the controlled and enhanced expression of Type 1 PKS genes in heterologous cells drawn from a wide range of actinomycetes. Examples of such promoter/activator gene combinations include the promoters of the dnr gene cluster and the dnrI activator gene from the daunorubicin gene cluster of *Streptomyces peucetius:* (Madduri, K. and Hutchinson, C. R. J. Bacteriol (1995) 177:1208-1215) and the promoter of the gene redX and the activator gene redD from the undecylprodigiosin gene cluster of *S. coelicolor* (Takano, E. et al. Mol. Microbiol. (1992) 2: 2797-2804).

Secondly, the above descriptions illustrate for the first time the construction of hybrid Type I PKS genes and their use to obtain novel polyketide products of utility as chiral synthetic intermediates or as bioactive materials such as antibiotics. Hybrid PKS genes have been constructed either by substitution of loading modules, or by substitution of individual domains in extension modules; or by substitution of whole modules. Thus, the replacement of the ery loading module by the avr loading loading module has been described herein to obtain either novel erythromycin A analogues or triketide lactones. It will readily occur to those skilled in the art that other alterations of the ery loading module can be obtained through its replacement with the loading module of other Type I PKS gene sets. Examples of such alterations include replacement with the loading module of the rap PKS; and with the loading module of the FK506-producing PKS. Such alterations will lead to the synthesis of polyketides specifically altered in their starter unit.

It is well-known to those skilled in the art that the avr loading module is capable of accepting a wide range of non-natural carboxylic acids as alternative starter units, when these are included in the fermentation medium. Therefore in the light of the present invention, it is evident that in addition to the synthesis of novel erythromycin A derivatives in which the C-13 substituent is isopropyl or sec-butyl instead of ethyl, which has been shown here, many other novel erythromycin A derivatives can be obtained by feeding of the appropriate non-natural carboxylic acids (or compounds convertible to them by fermentation) to an appropriate strain housing the hybrid PKS, such non-natural carboxylic acids having in general the formula R—COOH, where R is an alpha-branched group, and where the carbon bearing the —COOH group is also attached to at least two other atoms or groups other than hydrogen, with the preferred non-natural carboxylic acids being those described for the production of non-natural avermectins in European Patent EP 214,731, Mar. 18 1987, Pfizer). The resulting novel analogues of erythromycin A can be converted, by procedures well understood in the art, into further novel semi-synthetic derivatives of erythromycin A, of considerable utility in the treatment of bacterial infection, including for example ketolides and azalides. These embodiments of the invention are novel chiral materials of potential utility in the chemical synthesis of valuable bioactive products. The products which are 14-membered macrolides are novel erythromycin A analogues which are highly valuable antibacterial agents having the same microbial targets as do the known erythromycins and the semi-synthetic derivatives of known erythromycins, such as the ketolides disclosed in French patents Nos. 2697523 (May 6, 1994)

Roussel Uclaf; 269724 (May 6, 1994) Roussel Uclaf; and 2702480 (Sep. 16, 1994) Roussel Uclaf.

It will be evident to those skilled in the art that the replacement of the ery loading module by the loading module of the rap PKS will also lead to novel and useful analogues of erythromycin A, in which the natural propionate starter unit is substituted by a cycloalkylcarboxylic acid starter unit. Further examples of the formation of such hybrid Type I PKS include, but are not limited to, the replacement of the rap loading module in *Streptomyces hygroscopicus* by the avr loading module, leading to the formation of non-natural rapamycins; and the replacement of the avr loading module in *Streptomyces avermitilis* by the rap loading module, leading to the formation of further examples of non-natural avermectins. The present invention also encompasses mutants in which more than one of the genetic manipulations described in the examples are combined.

In the light of the present invention, it will also be evident that alterations in the specificity of the loading module of a Type I PKS can alternatively be achieved by the mutation of the genes encoding the natural loading module, and then selection for the desired altered specificity, as practised for example in the technique of in vitro gene shuffling (Stemmer, W. P. Nature (1994) 370:389-391).

The examples listed above also teach the construction and use of a low copy number plasmid vector pCJR101 as a vector for delivery of PKS genes into suitable actinomycete hosts. Plasmid pCJR101 is derived from the plasmid SCP2* (Bibb, M. J. and Hopwood, D. A. J. Gen. Microbiol. (1977) 154:155-166) found in the strain *Streptomyces coelicolor* M110 deposited for example at the Northern Regional Research Laboratory, Peoria, Ill., USA under the accession number NRRL 15041. Plasmid SCP2* has been previously used in the construction of several useful vectors such as pIJ2839 (Ingram, C. et al. J. Bacteriol. (1989) 171:6617-6624); plasmid pHJL197 (Larson, J. L. and Hershberger, C. L. J. Bacteriol. (1983) 157:314-317) and pRM5 (McDaniel, R. et al. Science (1993) 262:1546-1550). It will be evident to those skilled in the art that either these or other SCP2*-based plasmids may be substituted for pCJR101 either directly or after modification of the vector to introduce suitable promoter linked to the PKS genes, as demonstrated by the use of plasmid pRM5 in several Examples described herein. High copy number vectors such as plasmid pGM8 (Muth, G. et al. Mol. Gen. Genet. (1989) 219:341-350) derived from the *Streptomyces ghanaensis* plasmid pGS5 are also suitable as substitutes for pCJR101, as are integrative vectors such as plasmid pSAM2 (Murakami, T. et al. J. Bacteriol. (1989) 171:1459-14??). Those skilled in the art will readily appreciate the versatility of approaches to increasing the rate of biosynthesis of natural or non-natural complex polyketides such as macrolides and polyethers through heterologous use of type II PKS activator genes and their cognate promoters as disclosed here, in numerous derivatives of vectors well known in the art as useful for genetic engineering in actinomycetes.

In the construction of hybrid type I PKS genes, the Examples teach how the structural genes encoding both donor and acceptor PKS components may be spliced together to create functional catalysts capable of bringing about the synthesis of novel polyketides. The present invention shows that in choosing where the junction will be made between the donor and the acceptor DNA it is, surprisingly, not necessary to limit the choice to positions known or predicted to lie between domains in so-called linker regions. Instead it is preferred for junctions to be in the edge regions of domains (particularly KS or AT domains), where the sequences are highly conserved. Further, creation of junctions that lead to conservative changes in amino acid sequence at such junctions in the gene product are tolerated. It is also evident that for the purposes of creating a hybrid, PKS modules may be combined from two or more natural PKS. In the examples given here, donor DNA is spliced into the acceptor DNA at a position variously in the acyl carrier protein (ACP) domain or in the ketosynthase (KS) domain of a module, but the scope of the invention includes hybrid PKS where the junctions between homologous domains are chosen to lie within any of the constituent parts of a type I PKS module. However, it will be found most advantageous to select a position for each junction that lies within a domain, and close to one edge, so that the specificity of the chimaeric module is readily predictable, and so that disturbance of its proper functioning is minimised.

It will be readily appreciated that in the light of the present invention a hybrid PKS can be constructed by selecting pieces of DNA encoding respectively a loading module, a variable number of extension modules up to at least six in number, and a chain-releasing thioesterase domain; and concatenating the DNA, using standard procedures, in the order in which it is intended that the gene products operate. NB: The hybrid PKS with (say) 6 modules may be part of an assembly of synthases leading to a product produced by many more than 6 extension modules. It will also readily occur to those skilled in the art that the module-sized DNA fragments may be constituted in more than way, Thus the present invention includes the construction of functional hybrid PKsS exemplified by the construct containing the following activities in a single polypeptide chain:

AT0-ACP0-KS1-[ATR1-DHR1-ERR1-KRR1-ACPR1-KSR2]-AT2-KR2-ACP2-TE where the activities shown in square brackets are derived from modules 1 and 2 of the rap PKS, and the rest are derived from the loading module, extension modules 1 and 2, and the chain-terminating thioesterase of DEBS1. In such constructs, each ketossynthase domain is kept together with the ACP, AT and reductive domains of the module that precedes it in the naturally occurring PKS from which it was derived, rather than with the activities of its own module. Alternative but equally functional arrangements of the module-sized DNA building blocks for construction of hybrid PKS will readily occur to those skilled in the art.

The invention claimed is:

1. A method for producing a gene assembly encoding a functional hybrid type I polyketide synthase (PKS), said method comprises joining:
   a) a first nucleic acid molecule which encodes at least one domain of a first type I PKS, wherein said first nucleic acid molecule consists of a nucleic acid sequence encoding the loading module and the ketosynthase (KS) domain of the first adjacent extension module of said first type I PKS, wherein said loading module consists of an acyltransferase (AT) domain and an acyl carrier protein (ACP) domain; and
   b) a second nucleic acid molecule which encodes an extension module(s) which lacks the first ketosynthase domain of a second type I PKS;
   thereby forming a gene assembly encoding a functional hybrid type I PKS which produces a polyketide,
   wherein said first type I PKS is heterologous to said second type I PKS.

2. The method of claim 1, wherein the second nucleic acid molecule is joined with the first nucleic acid molecule in a host cell, wherein said first nucleic acid molecule is in the chromosome of said host cell.

3. The method of claim 2, wherein the host cell is selected from the group consisting of *Saccharopolyspora erythraea, Streptomyces coelicolor, Streptomyces avermitilis, Streptomyces griseofuscus, Streptomyces cinnamonensis, Micromonospora griseorubida, Streptomyces hygroscopicus, Streptomyces fradiae, Streptomyces longisporoflavus, Streptomyces lasaliensis, Streptomyces tsukubaensis, Streptomyces griseus, Streptomyces venezuelae, Streptomyces antibioticus, Streptomyces lividans, Streptomyces rimosus* and *Streptomyces albus*.

4. The method of claim 3, wherein the host cell is *Saccharopolyspora erythraea*.

5. The method of claim 1, wherein said first and second nucleic acid molecules are joined at a conserved region.

6. The method of claim 1, wherein the gene assembly encoding the functional hybrid type I PKS encodes at least a loading module and between 1 and 6 extension modules.

7. The method of claim 1, wherein the gene assembly encoding the functional hybrid type I PKS encodes at least a loading module and at least 2 extension modules.

8. The method of claim 1, wherein the loading module and the adjacent KS domain of the first extension module is selected from the group consisting of erythromycin PKS, avermectin PKS, monensin PKS, tetronasin PKS, oleandomycin PKS, amphotericin PKS, and rifamycin PKS.

9. The method of claim 8, wherein said first nucleic acid molecule encodes the avermectin loading module and the adjacent KS domain of the first avermectin extension module.

10. The method of 8, wherein said first nucleic acid molecule encodes the erythromycin loading module and the adjacent KS domain of the first erythromycin extension module.

11. The method of claim 1, wherein the second nucleic acid molecule is selected from the group consisting of extension modules from for erythromycin PKS, avermectin PKS, rapamycin PKS, ascomycin PKS, FK506 PKS, monensin PKS, tetronasin PKS, oleandomycin PKS, amphotericin PKS, and rifamycin PKS.

12. The method of claim 11, wherein said second nucleic acid molecule is from the erythromycin PKS.

13. The method of claim 1, wherein the second nucleic acid molecule additionally encodes a thioesterase domain.

14. The method of claim 1, wherein the first nucleic acid molecule is joined with the second nucleic acid molecule in a host cell, wherein said second nucleic acid molecule is in the chromosome of said host cell.

15. The method of claim 1, wherein said functional hybrid type I PKS produces different polyketides.

16. The method of claim 1, wherein said method is performed in vitro.

17. A method for producing a gene assembly encoding a functional hybrid type I polyketide synthase (PKS), said method comprises replacing, in a gene assembly encoding a first type I PKS, a first nucleic acid molecule encoding only a loading module and the ketosynthase (KS) domain of the first adjacent extension module with a second nucleic acid molecule encoding only a loading module and the KS domain of the first adjacent extension module,
   wherein said second nucleic acid molecule is from a second type I PKS,
   wherein said first type I PKS is heterologous to said second type I PKS,
   wherein said loading modules consist of an acyltransferase (AT) domain and an acyl carrier protein (ACP) domain
   thereby forming a gene assembly encoding a functional hybrid type I PKS which produces a polyketide.

* * * * *

SEQUENCE LISTING

<160> NUMBER OF SEQ ID NOS: 93

<210> SEQ ID NO 1
<211> LENGTH: 56
<212> TYPE: DNA
<213> ORGANISM: Artificial Sequence
<220> FEATURE:
<223> OTHER INFORMATION: Primer -continued

<400> SEQUENCE: 1
acgcguacua guccgattaa ttaaggagga ccatcatggc ggacctgtca aagctc        56

<210> SEQ ID NO 2
<211> LENGTH: 63
<212> TYPE: DNA
<213> ORGANISM: Artificial Sequence
<220> FEATURE:
<223> OTHER INFORMATION: Primer

<400> SEQUENCE: 2
auggagaucu cuccgctagc ggttcgccgg gcgccgcttc gttggtccgc gcgcgggttt    60
ccc                                                                 63

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
actagtccac tgcctctcgg taaaatccag c                                   31

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
cttaagaggg gctccaccgc gttcacggac                                     30

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
acattctcta cgcctaagtg ttcccctccc tgcctc                              36

<210> SEQ ID NO 6
<211> LENGTH: 53
<212> TYPE: DNA
<213> ORGANISM: Artificial Sequence
<220> FEATURE:
<223> OTHER INFORMATION: Primer

<400> SEQUENCE: 6
gtgatgtatg ctcatatgtg tcctccttaa ttaatcgatg cgttcgtccg gtg           53

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
tgaacaccaa gcttgccaga gagcgacgac ttcccc                              36

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
gacagattgc atgcccttcg aggagtgccc gcccgg                    36

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
gacagattct cgagccttcg aggagtgccc gcccgg                    36

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
taaggaggac acatatgca                                       19

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
taattcctcc tgtgtat                                         17

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cccatatggc ggacctgtca aagc                                 24

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
attgcgcgcc ctggcccggg aa                                   22

<210> SEQ ID NO 14
<211> LENGTH: 22
<212> TYPE: DNA
<213> ORGANISM: Artificial Sequence
<220> FEATURE:
<223> OTHER INFORMATION: Primer

```
<400> SEQUENCE: 14
aattcatagt ctagaagctt at                                              22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cgataagctt ctagactatg                                                 20

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
ctcgtcggtg gctttgcg                                                   18

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
cccgggaaaa acgaagacta gtggcgcgga cggccg                               36

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
cacgcgcagc gcggcgga                                                   18

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
cgaaccgcta gcggtcgtcg cgatggcct                                       29

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
gtggcccggc cgtccgcgcc actagtcttc gttttt                               36
```

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
aacagctagc ggttcgtccg ccgctgccgt gcc                             33

<210> SEQ ID NO 22
<211> LENGTH: 48
<212> TYPE: DNA
<213> ORGANISM: Artificial Sequence
<220> FEATURE:
<223> OTHER INFORMATION: Primer

<400> SEQUENCE: 22
aattcacatc accatcacca tcactagtag gaggtctggc catctaga             48

<210> SEQ ID NO 23
<211> LENGTH: 46
<212> TYPE: DNA
<213> ORGANISM: Artificial Sequence
<220> FEATURE:
<223> OTHER INFORMATION: Primer

<400> SEQUENCE: 23
cgcttctaga tggccagacc tcctactagt gatggtgatg gtgatg               46

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
gcagggatat cgcacgttcc tgg                                        23

<210> SEQ ID NO 25
<211> LENGTH: 31
<212> TYPE: DNA
<213> ORGANISM: Artificial Sequence
<220> FEATURE:
<223> OTHER INFORMATION: Primer

<400> SEQUENCE: 25
cgccgagatc tgcgaaggcc tggtcggcgg g                               31

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
atgaattccc tccgcccagc cag                                        23

<210> SEQ ID NO 27
<211> LENGTH: 28
<212> TYPE: DNA
<213> ORGANISM: Artificial Sequence
<220> FEATURE:
<223> OTHER INFORMATION: Primer

```
<400> SEQUENCE: 27
acagatctcg gcttcgactc gctgaccg                                    28

<210> SEQ ID NO 28
<211> LENGTH: 55
<212> TYPE: DNA
<213> ORGANISM: Artificial Sequence
<220> FEATURE:
<223> OTHER INFORMATION: Primer

<400> SEQUENCE: 28
acgcguacua gucagatctg ggcatcaatt cgctgaccgc ggtggaactg cgcaa      55

<210> SEQ ID NO 29
<211> LENGTH: 54
<212> TYPE: DNA
<213> ORGANISM: Artificial Sequence
<220> FEATURE:
<223> OTHER INFORMATION: Primer

<400> SEQUENCE: 29
auggagaucu cucagatctt gaatgcggcg gctgcgggga tggtgctggc gtca       54

<210> SEQ ID NO 30
<211> LENGTH: 45
<212> TYPE: DNA
<213> ORGANISM: Artificial Sequence
<220> FEATURE:
<223> OTHER INFORMATION: Primer

<400> SEQUENCE: 30
gcacccacga cgccaccacc acatatgccc tgcaccctgc cctcc                 45

<210> SEQ ID NO 31
<211> LENGTH: 57
<212> TYPE: DNA
<213> ORGANISM: Artificial Sequence
<220> FEATURE:
<223> OTHER INFORMATION: Primer

<400> SEQUENCE: 31
acgcguacua guccgattaa ttaaggagga ccatcaatgg cggacctgtc aaagctc    57

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32
auggagaucu cuccgctagc gattgtgggt atggcg                           36

<210> SEQ ID NO 33
<211> LENGTH: 47
<212> TYPE: DNA
<213> ORGANISM: Artificial Sequence
<220> FEATURE:
<223> OTHER INFORMATION: Primer

<400> SEQUENCE: 33
acgcguacua guccatgcat ctgcagcacg gcggcctcat caccgga               47
```

<210> SEQ ID NO 34
<211> LENGTH: 41
<212> TYPE: DNA
<213> ORGANISM: Artificial Sequence
<220> FEATURE:
<223> OTHER INFORMATION: Primer

<400> SEQUENCE: 34
acgcguacua guccatgcat tcccggagcg gcgatctgtg g                41

<210> SEQ ID NO 35
<211> LENGTH: 53
<212> TYPE: DNA
<213> ORGANISM: Artificial Sequence
<220> FEATURE:
<223> OTHER INFORMATION: Primer

<400> SEQUENCE: 35
auggagaucu cucccgcggc cgcgctgtca cgcaccagct tcagcagtgc gtc       53

<210> SEQ ID NO 36
<211> LENGTH: 41
<212> TYPE: DNA
<213> ORGANISM: Artificial Sequence
<220> FEATURE:
<223> OTHER INFORMATION: Primer

<400> SEQUENCE: 36
acgcguacua guccgcggcc gcgatcctcg ggcattccag c                41

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37
auggagaucu cuaagcattg gtaactgtc                              29

<210> SEQ ID NO 38
<211> LENGTH: 45
<212> TYPE: DNA
<213> ORGANISM: Artificial Sequence
<220> FEATURE:
<223> OTHER INFORMATION: Primer

<400> SEQUENCE: 38
acgcguacua guatctagac catgcatgtt tgacagctta tcatc             45

<210> SEQ ID NO 39
<211> LENGTH: 45
<212> TYPE: DNA
<213> ORGANISM: Artificial Sequence
<220> FEATURE:
<223> OTHER INFORMATION: Primer

<400> SEQUENCE: 39
auggagaucu cuatctagac catgcatgcc gccggcttcc attca             45

<210> SEQ ID NO 40
<211> LENGTH: 33
<212> TYPE: DNA
<213> ORGANISM: Artificial Sequence
<220> FEATURE:
<223> OTHER INFORMATION: Primer

```
<400> SEQUENCE: 40
gagcagtcgt tccgagatct cggcttcgat tca                              33

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
gggaggagat cagatcccag aagt                                        24

<210> SEQ ID NO 42
<211> LENGTH: 33
<212> TYPE: DNA
<213> ORGANISM: Artificial Sequence
<220> FEATURE:
<223> OTHER INFORMATION: Primer

<400> SEQUENCE: 42
gagggagtcg aaccgagatc tcggaacgcg cgg                              33

<210> SEQ ID NO 43
<211> LENGTH: 31
<212> TYPE: DNA
<213> ORGANISM: Artificial Sequence
<220> FEATURE:
<223> OTHER INFORMATION: Primer

<400> SEQUENCE: 43
gggggatcct ggggtcggcc gggcagggca a                                31

<210> SEQ ID NO 44
<211> LENGTH: 29
<212> TYPE: DNA
<213> ORGANISM: Artificial Sequence
<220> FEATURE:
<223> OTHER INFORMATION: Primer

<400> SEQUENCE: 44
gtctcaagct tcggcatcag cggcaccaa                                   29

<210> SEQ ID NO 45
<211> LENGTH: 28
<212> TYPE: DNA
<213> ORGANISM: Artificial Sequence
<220> FEATURE:
<223> OTHER INFORMATION: Primer

<400> SEQUENCE: 45
cgtgcgatat ccctgctcgg cgagcgca                                    28

<210> SEQ ID NO 46
<211> LENGTH: 32
<212> TYPE: DNA
<213> ORGANISM: Artificial Sequence
<220> FEATURE:
<223> OTHER INFORMATION: Primer

<400> SEQUENCE: 46
catggcctgc aggctgcccg gggaggtcga ct                               32
```

```
<210> SEQ ID NO 47
<211> LENGTH: 35
<212> TYPE: DNA
<213> ORGANISM: Artificial Sequence
<220> FEATURE:
<223> OTHER INFORMATION: Primer

<400> SEQUENCE: 47
cccgaagctt gacacacctg cccggcgcac cccgt                              35

<210> SEQ ID NO 48
<211> LENGTH: 27
<212> TYPE: DNA
<213> ORGANISM: Artificial Sequence
<220> FEATURE:
<223> OTHER INFORMATION: Primer

<400> SEQUENCE: 48
gcgcgccaat tgcgtgcaca tctcgat                                      27

<210> SEQ ID NO 49
<211> LENGTH: 37
<212> TYPE: DNA
<213> ORGANISM: Artificial Sequence
<220> FEATURE:
<223> OTHER INFORMATION: Primer

<400> SEQUENCE: 49
cctgcaggcc atcgcgacga ccgcgaccgg ttcgccg                            37

<210> SEQ ID NO 50
<211> LENGTH: 32
<212> TYPE: DNA
<213> ORGANISM: Artificial Sequence
<220> FEATURE:
<223> OTHER INFORMATION: Primer

<400> SEQUENCE: 50
gatggcctgc aggctgcccg gcggtgtgag ca                                 32

<210> SEQ ID NO 51
<211> LENGTH: 34
<212> TYPE: DNA
<213> ORGANISM: Artificial Sequence
<220> FEATURE:
<223> OTHER INFORMATION: Primer

<400> SEQUENCE: 51
gccgaagctt gagacccccg cccggcgcgg tcgc                               34

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52
tggcttcgct ggcggacacg ctcag                                         25

<210> SEQ ID NO 53
<211> LENGTH: 32
<212> TYPE: DNA
<213> ORGANISM: Artificial Sequence
<220> FEATURE:
<223> OTHER INFORMATION: Primer
```

```
<400> SEQUENCE: 53
cctgcaggcc atgccgacga tcgcgatcgg ct                        32

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
gtcaagcttc ggggtgagcg ggacgaa                              27

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
gcgtccggac gtggctccag ca                                   22

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
ggagtactgc gagggcgtgg gcat                                 24

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
cacctaggac cgcttcccag tcgacc                               26

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58
tacctaggcc gggccggact ggtcgacctg ccgggtt                   37

<210> SEQ ID NO 59
<211> LENGTH: 29
<212> TYPE: DNA
<213> ORGANISM: Artificial Sequence
<220> FEATURE:
<223> OTHER INFORMATION: Primer

<400> SEQUENCE: 59
atcctcaggc tctccgtctc cggttctcc                            29
```

<210> SEQ ID NO 60
<211> LENGTH: 34
<212> TYPE: DNA
<213> ORGANISM: Artificial Sequence
<220> FEATURE:
<223> OTHER INFORMATION: Primer

<400> SEQUENCE: 60
tacctgaggg accggctagc gggtctgccg cgtg 34

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
cttctagact atgaattccc tccgcccagc 30

<210> SEQ ID NO 62
<211> LENGTH: 34
<212> TYPE: DNA
<213> ORGANISM: Artificial Sequence
<220> FEATURE:
<223> OTHER INFORMATION: Primer

<400> SEQUENCE: 62
cgcctaggca ccaccacaac ccgggtactg gacc 34

<210> SEQ ID NO 63
<211> LENGTH: 36
<212> TYPE: DNA
<213> ORGANISM: Artificial Sequence
<220> FEATURE:
<223> OTHER INFORMATION: Primer

<400> SEQUENCE: 63
tagctagccg ggcgctcagg ggctgcgagc cgacct 36

<210> SEQ ID NO 64
<211> LENGTH: 34
<212> TYPE: DNA
<213> ORGANISM: Artificial Sequence
<220> FEATURE:
<223> OTHER INFORMATION: Primer

<400> SEQUENCE: 64
cctaggcacc accacggccc gggtgctgga cctt 34

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
cctcaggctg tcaccggtag aggcggccct 30

<210> SEQ ID NO 66
<211> LENGTH: 32
<212> TYPE: DNA
<213> ORGANISM: Artificial Sequence
<220> FEATURE:
<223> OTHER INFORMATION: Primer

<400> SEQUENCE: 66
atcctaggac cgcttcccag tcgaccgcga ca                          32

<210> SEQ ID NO 67
<211> LENGTH: 28
<212> TYPE: DNA
<213> ORGANISM: Artificial Sequence
<220> FEATURE:
<223> OTHER INFORMATION: Primer

<400> SEQUENCE: 67
gccactagtg tggcgtgggg gctgtggg                               28

<210> SEQ ID NO 68
<211> LENGTH: 30
<212> TYPE: DNA
<213> ORGANISM: Artificial Sequence
<220> FEATURE:
<223> OTHER INFORMATION: Primer

<400> SEQUENCE: 68
tgaattccct ccgcccagcc aggcgtcgat                             30

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
cctggagtac tgcgagggcg tg                                     22

<210> SEQ ID NO 70
<211> LENGTH: 32
<212> TYPE: DNA
<213> ORGANISM: Artificial Sequence
<220> FEATURE:
<223> OTHER INFORMATION: Primer

<400> SEQUENCE: 70
ctgactagtg gcggtgacgt gggcggggga aa                          32

<210> SEQ ID NO 71
<211> LENGTH: 35
<212> TYPE: DNA
<213> ORGANISM: Artificial Sequence
<220> FEATURE:
<223> OTHER INFORMATION: Primer

<400> SEQUENCE: 71
cccctgcagc cggaccgcac caccctcgt gacga                        35

<210> SEQ ID NO 72
<211> LENGTH: 26
<212> TYPE: DNA
<213> ORGANISM: Artificial Sequence
<220> FEATURE:
<223> OTHER INFORMATION: Primer

<400> SEQUENCE: 72
ggcggaacgt cttcccggcg gcacct                                 26

<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
cccctgcagc cagtaccgct ggggctcgaa                                30

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
catgctcgag ctctcctggg aagt                                      24

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75
caaccctggc cagggaagac gaagacgg                                  28

<210> SEQ ID NO 76
<211> LENGTH: 25
<212> TYPE: DNA
<213> ORGANISM: Artificial Sequence
<220> FEATURE:
<223> OTHER INFORMATION: Primer

<400> SEQUENCE: 76
ttccctggcc aggggtcgca gcgtg                                     25

<210> SEQ ID NO 77
<211> LENGTH: 25
<212> TYPE: DNA
<213> ORGANISM: Artificial Sequence
<220> FEATURE:
<223> OTHER INFORMATION: Primer

<400> SEQUENCE: 77
cacctaggac cgcggaccac tcgac                                     25

<210> SEQ ID NO 78
<211> LENGTH: 27
<212> TYPE: DNA
<213> ORGANISM: Artificial Sequence
<220> FEATURE:
<223> OTHER INFORMATION: Primer

<400> SEQUENCE: 78
tggccaggga gtcggtgcac ctaggca                                   27

<210> SEQ ID NO 79
<211> LENGTH: 25
<212> TYPE: DNA
<213> ORGANISM: Artificial Sequence
<220> FEATURE:
<223> OTHER INFORMATION: Primer

```
<400> SEQUENCE: 79
gccgacagcg agtcgacgcc gagtt                                          25

<210> SEQ ID NO 80
<211> LENGTH: 28
<212> TYPE: DNA
<213> ORGANISM: Artificial Sequence
<220> FEATURE:
<223> OTHER INFORMATION: Primer

<400> SEQUENCE: 80
ctggccaggg cgcgcaatgg ccgagcat                                       28

<210> SEQ ID NO 81
<211> LENGTH: 34
<212> TYPE: DNA
<213> ORGANISM: Artificial Sequence
<220> FEATURE:
<223> OTHER INFORMATION: Primer

<400> SEQUENCE: 81
ccctaggagt cgccggcagt ccagcgcggc gccc                                34

<210> SEQ ID NO 82
<211> LENGTH: 34
<212> TYPE: DNA
<213> ORGANISM: Artificial Sequence
<220> FEATURE:
<223> OTHER INFORMATION: Primer

<400> SEQUENCE: 82
aattcataac tagtaggagg tctggccatc taga                                34

<210> SEQ ID NO 83
<211> LENGTH: 34
<212> TYPE: DNA
<213> ORGANISM: Artificial Sequence
<220> FEATURE:
<223> OTHER INFORMATION: Primer

<400> SEQUENCE: 83
tcgaagatct accggtctgg aggatgatca atac                                34

<210> SEQ ID NO 84
<211> LENGTH: 27
<212> TYPE: DNA
<213> ORGANISM: Artificial Sequence
<220> FEATURE:
<223> OTHER INFORMATION: Primer

<400> SEQUENCE: 84
ggcgggtccg gaggtgttca ccgagtt                                        27

<210> SEQ ID NO 85
<211> LENGTH: 27
<212> TYPE: DNA
<213> ORGANISM: Artificial Sequence
<220> FEATURE:
<223> OTHER INFORMATION: Primer

<400> SEQUENCE: 85
accttggcca gggaagacga acactga                                        27
```

<210> SEQ ID NO 86
<211> LENGTH: 36
<212> TYPE: DNA
<213> ORGANISM: Artificial Sequence
<220> FEATURE:
<223> OTHER INFORMATION: Primer

<400> SEQUENCE: 86
tcctaggccg ggccggactg gtcgacctgc cgggtt                              36

<210> SEQ ID NO 87
<211> LENGTH: 26
<212> TYPE: DNA
<213> ORGANISM: Artificial Sequence
<220> FEATURE:
<223> OTHER INFORMATION: Primer

<400> SEQUENCE: 87
aaacaccgcg acctggtcct ccgagc                                         26

<210> SEQ ID NO 88
<211> LENGTH: 33
<212> TYPE: DNA
<213> ORGANISM: Artificial Sequence
<220> FEATURE:
<223> OTHER INFORMATION: Primer

<400> SEQUENCE: 88
tttgctagcg atcgtcggca tggcgtgccg gtt                                 33

<210> SEQ ID NO 89
<211> LENGTH: 24
<212> TYPE: DNA
<213> ORGANISM: Artificial Sequence
<220> FEATURE:
<223> OTHER INFORMATION: Primer

<400> SEQUENCE: 89
cccacgagat ctccagcatg atcc                                           24

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
ggcggcatgc ggcggttcct                                                20

<210> SEQ ID NO 91
<211> LENGTH: 50
<212> TYPE: DNA
<213> ORGANISM: Artificial Sequence
<220> FEATURE:
<223> OTHER INFORMATION: Primer

<400> SEQUENCE: 91
aagctagcgg ttcgccgggc gccgcttcgt tggtccgcgc gcgggttaac               50

<210> SEQ ID NO 92
<211> LENGTH: 40
<212> TYPE: DNA
<213> ORGANISM: Artificial Sequence
<220> FEATURE:
<223> OTHER INFORMATION: Primer -continued

```
<400> SEQUENCE: 92
aacccgcgcg cggaccaacg aagcggcgcc cggcgaaccg                                40

<210> SEQ ID NO 93
<211> LENGTH: 44
<212> TYPE: DNA
<213> ORGANISM: Artificial Sequence
<220> FEATURE:
<223> OTHER INFORMATION: Primer

<400> SEQUENCE: 93
ctagcggttc gccgggcgcc gcttcgttgg tccgcgcgcg ggtt                           44
```